United States Patent
To et al.

(10) Patent No.: US 12,201,348 B2
(45) Date of Patent: Jan. 21, 2025

(54) MEDICAL DEVICE SYSTEMS AND METHODS INCLUDING HELICALLY CONFIGURED OR TWISTED, NON-HELICALLY CONFIGURED ELONGATE MEMBERS

(71) Applicant: KARDIUM INC., Burnaby (CA)

(72) Inventors: Derrick Kevin To, Vancouver (CA); Fernando Luis de Souza Lopes, Delta (CA); Saar Moisa, Vancouver (CA); Ashkan Sardari, North Vancouver (CA); John Andrew Funk, Delta (CA); Peter Josiah Hawes, Burnaby (CA); Calvin Dane Cummings, Surrey (CA)

(73) Assignee: KARDIUM INC., Burnaby (CA)

( * ) Notice: Subject to any disclaimer, the term of this patent is extended or adjusted under 35 U.S.C. 154(b) by 1262 days.

(21) Appl. No.: 16/580,397

(22) Filed: Sep. 24, 2019

(65) Prior Publication Data

US 2020/0015890 A1    Jan. 16, 2020

Related U.S. Application Data

(63) Continuation of application No. PCT/CA2018/000072, filed on Apr. 9, 2018.
(Continued)

(51) Int. Cl.
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/00267* (2013.01);
(Continued)

(58) Field of Classification Search
CPC ....... A61B 5/6858; A61B 5/283; A61B 5/287; A61B 5/29; A61B 2018/00267;
(Continued)

(56) References Cited

U.S. PATENT DOCUMENTS

| 5,309,910 A | 5/1994 | Edwards |
| 9,452,016 B2 | 9/2016 | Moisa |

(Continued)

FOREIGN PATENT DOCUMENTS

| WO | 0051683 A1 | 9/2000 |
| WO | 2015179734 A1 | 11/2015 |

OTHER PUBLICATIONS

International Search Report issued in Intl. Appln. No. PCT/CA2018/000072 mailed Jul. 19, 2018.
(Continued)

*Primary Examiner* — Eun Hwa Kim
*Assistant Examiner* — Christine A Dedoulis
(74) *Attorney, Agent, or Firm* — ROSSI, KIMMS & McDOWELL LLP

(57) ABSTRACT

A medical device system may include transducers and a structure on which the transducers are located. The structure may include at least a first portion of each elongate member of a plurality of elongate members. Each respective set of a plurality of sets of one or more of the transducers may be located on a respective one of the plurality of elongate members. The structure may be selectively moveable between a delivery configuration in which the structure is sized to be percutaneously deliverable to a bodily cavity and a deployed configuration in which the structure is sized too large to be percutaneously deliverable to the bodily cavity. The second portion of each elongate member of the plurality of elongate members may be arranged in a helical configuration or a twisted, non-helical configuration including at
(Continued)

least 360 degrees of rotation when the structure is in the delivery configuration.

37 Claims, 14 Drawing Sheets

Related U.S. Application Data

(60) Provisional application No. 62/484,456, filed on Apr. 12, 2017.

(52) U.S. Cl.
CPC ........... *A61B 2018/00351* (2013.01); *A61B 2018/00577* (2013.01); *A61B 2018/00797* (2013.01); *A61B 2018/00827* (2013.01); *A61B 2018/00892* (2013.01); *A61B 2018/1435* (2013.01)

(58) Field of Classification Search
CPC .... A61B 2018/0016; A61B 2018/1435; A61B 2562/187; A61B 2562/222
See application file for complete search history.

(56) References Cited

U.S. PATENT DOCUMENTS

| | | |
|---|---|---|
| 9,492,227 B2 | 11/2016 | Lopes |
| 10,406,198 B2 | 9/2019 | Hu |
| 2007/0083194 A1 | 4/2007 | Kunis |
| 2014/0039491 A1 | 2/2014 | Bakos |
| 2014/0114307 A1* | 4/2014 | Moisa ............... A61B 5/287 |
| | | 606/41 |
| 2015/0223757 A1 | 8/2015 | Werneth |
| 2015/0250424 A1* | 9/2015 | Govari ............ A61B 18/082 |
| | | 606/41 |

OTHER PUBLICATIONS

Written Opinion issued in Intl. Appln. No. PCT/CA2018/000072 mailed Jul. 19, 2018.
Kottkamp et al. "Global multielectrode contact mapping plus ablation with a single catheter: Preclinical and preliminary experience in humans with atrial fibrillation." Journal of Cardiovascular Electrophysiology. 2017:1-10.
Mounsey. "A novel multielectrode combined mapping and ablation basket catheter: A future player in the atrial fibrillation ablation space?" Journal of Cardiovascular Electrophysiology. 2017:1-2.

\* cited by examiner

MEDICAL DEVICE SYSTEMS AND METHODS INCLUDING HELICALLY CONFIGURED OR TWISTED, NON-HELICALLY CONFIGURED ELONGATE MEMBERS

CROSS-REFERENCE TO RELATED APPLICATION

This application is a continuation of International Application No. PCT/CA2018/000072, filed Apr. 9, 2018, which claims the benefit of U.S. Provisional Application No. 62/484,456, filed Apr. 12, 2017, the entire disclosure of both of these applications is hereby incorporated herein by reference.

TECHNICAL FIELD

Aspects of this disclosure generally are related at least to medical systems including operative elongate members exhibiting various configurations that facilitate delivery thereof to a bodily cavity. Delivery of the operative elongate members may include percutaneous or intravascular delivery thereof.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left and right atria to block various paths taken by the spurious electrical signals. Such lesions were originally created using incisions, but are now typically created by ablating the tissue with various techniques including radio-frequency (RF) energy, microwave energy, laser energy, electroporation and cryogenic techniques. The procedure is performed with a high success rate under the direct vision that is provided in open procedures, but is relatively complex to perform intravascularly or percutaneously because of the difficulty in creating the lesions in the correct locations using catheter-based systems. Difficulties in creating lesions in the correct locations within a bodily cavity using intravascular or percutaneous techniques are often associated with the delivery of various ablative elements to the bodily cavity and the manipulation of the various ablative elements within the bodily cavity. In this regard, the flexibility or the ability of various carrier members to bend in various directions to accurately deliver and position the ablative elements at the desired locations is important.

In this regard, the present inventors recognized that there exists a need in the art for improvement in various members employed to deliver to and position transducers or other sensing or ablative elements in one or more preferred locations within a bodily cavity, such as a heart, in order to successfully perform various diagnostic or treatment procedures.

SUMMARY

At least the above-discussed need is addressed and technical solutions are achieved by various embodiments of the present invention. In some embodiments, device systems and methods executed by such systems exhibit enhanced capabilities for the delivery and placement of one or more transducers provided by one or more elongate members at various preferred locations with respect to various regions of a tissue wall of a bodily cavity, and, in some embodiments, formation of one or more lesions in at least one of the various regions.

In some embodiments, a medical device system may be summarized as including a plurality of transducers positionable in a bodily cavity, and a structure on which the plurality of transducers are located. The structure may include at least a first portion of each elongate member of a plurality of elongate members. The plurality of transducers may include a plurality of sets of one or more of the transducers, each respective set of the plurality of sets of one or more of the transducers located on a respective one of the plurality of elongate members. The structure may be selectively moveable between a delivery configuration in which the structure is sized to be percutaneously deliverable to the bodily cavity, and a deployed configuration in which the structure is sized too large to be percutaneously deliverable to the bodily cavity. In various embodiments, a second portion of each elongate member of the plurality of elongate members is arranged in a helical configuration including at least 360 degrees of rotation when the structure is in the delivery configuration.

In some embodiments, the second portions of a set of at least two elongate members of the plurality of elongate members may be arranged in a collective helical configuration when the structure is in the deployed configuration. In some embodiments, the second portions of a set of at least two elongate members of the plurality of elongate members may be arranged in a collective helical configuration when the structure is in the delivery configuration. In some embodiments, each particular elongate member of the plurality of elongate members includes a length between a proximal portion of the particular elongate member and a distal end of the particular elongate member, and the plurality of sets of one or more of the transducers is located on distal portions of the plurality of elongate members, the distal portions closer, along the lengths of the elongate members, to the distal ends of the elongate members than the second portions of the plurality of elongate members when the structure is in the delivery configuration. In some embodiments, the second portions of the set of at least two elongate members of the plurality of elongate members may extend along a same rotational direction in the collective helical configuration when the structure is in the delivery configuration, the same rotational direction being a same clockwise direction or a same counterclockwise direction.

In some embodiments, each respective set of the plurality of sets of one or more of the transducers is located on the first portion of a respective elongate member of the plurality of elongate members. In some embodiments, the second portions of the plurality of elongate members are arranged in a particular configuration that remains sufficiently small in size to be percutaneously deliverable to the bodily cavity when the structure is moved from the delivery configuration to the deployed configuration.

In some embodiments, each respective set of the plurality of sets of one or more of the transducers is located on the first portion of a respective elongate member of the plurality of elongate members. In some embodiments, the first portions of the plurality of elongate members are arranged in a configuration too large to be percutaneously deliverable to the bodily cavity when the structure is in the deployed configuration. In some embodiments, the second portions of the plurality of elongate members are arranged in a particular configuration that remains sufficiently small in size to be percutaneously deliverable to the bodily cavity when the structure is moved from the delivery configuration to the deployed configuration.

In some embodiments, no transducer is located on the second portion of each elongate member of the plurality of elongate members.

In some embodiments, the at least 360 degrees of rotation is at least 540 degrees of rotation. In some embodiments, the at least 360 degrees of rotation is at least 720 degrees of rotation.

In some embodiments, the medical device system may include a control element coupled to at least one elongate member of the plurality of elongate members to at least in part control a configuration of at least the at least one elongate member, and the plurality of elongate members may wrap around at least a portion of the control element at least when the structure is in the delivery configuration.

In some embodiments, the medical device system may include a control element coupled to at least one elongate member of the plurality of elongate members to at least in part control a configuration thereof, and the second portions of the plurality of elongate members may wrap around at least a portion of the control element at least when the structure is in the delivery configuration. In some embodiments, the second portions of the plurality of elongate members may wrap around at least the portion of the control element when the structure is in the deployed configuration. In some embodiments, the second portions of the plurality of elongate members each wraps around the control element along a same rotational direction at least when the structure is in the delivery configuration, the same rotational direction being a same clockwise direction or a same counterclockwise direction.

In some embodiments, a portion of a first elongate member of the plurality of elongate members may be nested with a portion of a second elongate member of the plurality of elongate members at least when the structure is in the delivery configuration. In some embodiments, the second portion of each of at least a first elongate member of the plurality of elongate members may be nested with the second portion of a second elongate member of the plurality of elongate members at least when the structure is in the delivery configuration.

In some embodiments, for each particular elongate member of the plurality of elongate members, the first portion of the particular elongate member and the second portion of the particular elongate member are provided by a plurality of portions of the particular elongate member arranged between a proximal portion of the particular elongate member and a distal end of the particular elongate member, the plurality of portions of the particular elongate member collectively providing a front surface of the particular elongate member and a back surface of the particular elongate member opposite across a thickness of the particular elongate member from the front surface of the particular elongate member. In some embodiments, at least a portion of the front surface of each particular elongate member of the plurality of elongate members faces outwardly from an interior of the structure when the structure is in the deployed configuration, and at least a particular portion of the front surface of a first elongate member of the plurality of elongate members faces at least a particular portion of the back surface of a second elongate member of the plurality of elongate members when the structure is in the delivery configuration. In some embodiments, at least the particular portion of the front surface of the first elongate member may follow a contour of at least the particular portion of the back surface of the second elongate member. In some embodiments, the particular portion of the front surface of the first elongate member may be provided by the second portion of the first elongate member, and the particular portion of the back surface of the second elongate member may be provided by the second portion of the second elongate member. In some embodiments, at least the particular portion of the front surface of the first elongate member may follow the contour of at least the particular portion of the back surface of the second elongate member throughout the at least 360 degrees of rotation of the helical configuration of the second portion of the second elongate member.

In some embodiments, for each particular elongate member of the plurality of elongate members, the first portion of the particular elongate member and the second portion of the particular elongate member are provided by a plurality of portions of the particular elongate member arranged between a proximal portion of the particular elongate member and a distal end of the particular elongate member, the plurality of portions of the particular elongate member collectively providing a front surface of the particular elongate member and a back surface of the particular elongate member opposite across a thickness of the particular elongate member from the front surface of the particular elongate member. In some embodiments, at least a portion of the front surface of each elongate member of the plurality of elongate members faces outwardly from an interior of the structure when the structure is in the deployed configuration, and at least the second portions of a first set of at least three of the plurality of elongate members may be arranged front surface-toward-back surface in a first stacked arrangement when the structure is in the delivery configuration. In some embodiments, at least the second portions of the first set of at least three of the plurality of elongate members may be arranged front surface-toward-back surface in a second stacked arrangement when the structure is in the deployed configuration. In some embodiments, the first portions of a second set of at least three of the plurality of elongate members may be arranged front surface-toward-back surface in a second stacked arrangement when the structure is in the delivery configuration. In some embodiments, the second portions of a second set of at least three of the plurality of elongate members may be arranged front surface-toward-back surface in a second stacked arrangement when the structure is in the delivery configuration. In some embodiments, each respective set of the plurality of sets of one or more of the transducers is located on the first portion of a respective one of the elongate members. In some embodiments, the second portions of the plurality of elongate members do not include any transducers. In some embodiments, for each particular elongate member of the plurality of elongate members, the particular elongate member may include a flexible circuit structure extending between the proximal portion of the particular elongate member and the distal end of the particular elongate member, the flexible circuit structure including the second portion of the particular elongate member.

In some embodiments, the second portions of the plurality of elongate members do not include any transducers. In some embodiments, the second portions of the plurality of elongate members do not include any electrodes.

In some embodiments, the first portions of the plurality of elongate members may extend like lines of longitude about the structure when the structure is in the deployed configuration. In some embodiments, the first portion of each elongate member of the plurality of elongate members is not arranged in a helical configuration when the structure is in the delivery configuration. In some embodiments, the first portion of each elongate member of the plurality of elongate members is not arranged in a helical configuration when the structure is in the deployed configuration.

In some embodiments, the helical configuration of the second portion of a first elongate member of the plurality of elongate members may be axially offset from the helical configuration of the second portion of at least a second elongate member of the plurality of elongate members when the structure is in the delivery configuration. In some embodiments, the second portion of the first elongate member of the plurality of elongate members may extend along a same rotational direction as the second portion of the second elongate member of the plurality of elongate members when the structure is in the delivery configuration, the same rotational direction being a same clockwise direction or a same counterclockwise direction.

In some embodiments, the medical device system may include a shaft member physically coupled to the plurality of elongate members, a location at which the shaft member is physically coupled to each elongate member of the plurality of elongate members being fixed with respect to a shaft distal end of the shaft member. The shaft member may be configured to percutaneously deliver the structure to the bodily cavity at least in response to translation of at least part of the shaft member, and the shaft member may include a shaft proximal end, the shaft distal end, and an elongated portion extending between the shaft proximal end and the shaft distal end. In some embodiments, the second portion of each elongate member of the plurality of elongate member may be located within the elongated portion of the shaft member.

In some embodiments, the plurality of transducers may include a plurality of electrodes. In some embodiments, each transducer of the plurality of transducers may include a respective electrode.

In some embodiments, wherein, for each particular elongate member of the plurality of elongate members: the second portion of the particular elongate member is between a proximal portion of the particular elongate member and the first portion of the particular elongate member along a length of the particular elongate member, and the first portion of the particular elongate member is between the second portion of the particular elongate member and a distal end of the particular elongate member along the length of the particular elongate member. The particular elongate member may be configured to be percutaneously advanced distal end of the particular elongate member ahead of at least the proximal portion of the particular elongate member when the structure is in the delivery configuration. In some embodiments, a first width of the particular elongate member in the second portion is at least 10% less than a corresponding second width of the particular elongate member in the proximal portion of the particular elongate member. In some embodiments, the first width of the particular elongate member in the second portion is between 20% and 60%, inclusive, less than the corresponding second width of the particular elongate member in the proximal portion of the particular elongate member.

In some embodiments, wherein, for each particular elongate member of the plurality of elongate members: the first portion of the particular elongate member and the second portion of the particular elongate member are provided by a plurality of portions of the particular elongate member arranged between a proximal portion of the particular elongate member and a distal end of the particular elongate member. The plurality of portions of the particular elongate member may collectively provide a front surface of the particular elongate member and a back surface of the particular elongate member opposite across a thickness of the particular elongate member from the front surface of the particular elongate member, and the thickness of the particular elongate member may be perpendicular to a longitudinal axis of the particular elongate member. In some embodiments, wherein, for each particular elongate member of the plurality of elongate members: a first width of the particular elongate member in the second portion of the particular elongate member is at least 10% less, or in some embodiments is between 20% and 60%, inclusive, less than a second width of the particular elongate member in the proximal portion of the particular elongate member, and each of the first width and the second width is perpendicular to the thickness and the longitudinal axis of the particular elongate member. In some embodiments, the first widths of the particular elongate members of the plurality of elongate members are equal or within 5% of a same width. In some embodiments, wherein, for each particular elongate member of the plurality of elongate members: the proximal portion of the particular elongate member is adjacent the second portion of the particular elongate member along the longitudinal axis of the particular elongate member, and, in a state where the longitudinal axis of the particular elongate member resides within a same plane, the longitudinal axis of the particular elongate member bends by a bending angle between the proximal portion of the particular elongate member and the second portion of the particular elongate member, an absolute value of the bending angle being at least 5 degrees, in some embodiments, and being between 10 and 20 degrees, inclusive, in some embodiments. In some embodiments, the bending angle for each elongate member in a first subset of at least two elongate members of the plurality of elongate members is positive, and the bending angle for each elongate member in a second subset of at least two elongate members of the plurality of elongate members is negative, the elongate members in the first subset other than the elongate members in the second subset.

In some embodiments, various systems may include combinations and subsets of the systems summarized above.

In some embodiments, a medical device system may be summarized as including a plurality of transducer sets, each transducer set including one or more transducers positionable in a bodily cavity, and a plurality of elongate members, at least parts of the elongate members collectively forming a structure on which the plurality of transducer sets are located, each elongate member including at least a particular portion on which no transducer selectively operable to transmit energy is located. The structure may be selectively moveable between a delivery configuration in which the structure is sized to be percutaneously deliverable to the bodily cavity and a deployed configuration in which the structure is sized too large to be percutaneously deliverable to the bodily cavity. In some embodiments, each of the particular portions of the plurality of elongate members may include a helical configuration including at least 360 degrees of rotation when the structure is in the delivery configuration.

In some embodiments, each transducer set may be located on at least one portion of a respective one of the plurality of elongate members other than the particular portion of the respective one of the plurality of elongate members. In some embodiments, the particular portions of a set of at least two elongate members of the plurality of elongate members may be arranged in a collective helical configuration when the structure is in the delivery configuration.

In some embodiments, the particular portions of a set of at least two elongate members of the plurality of elongate members may be arranged in a collective helical configuration when the structure is in the deployed configuration.

In some embodiments, the particular portions of the plurality of elongate members may be arranged in a particular configuration that remains sufficiently small in size to be percutaneously deliverable to the bodily cavity when the structure is moved from the delivery configuration to the deployed configuration.

In some embodiments, the at least 360 degrees of rotation is at least 540 degrees of rotation. In some embodiments, the at least 360 degrees of rotation is at least 720 degrees of rotation.

In some embodiments, the medical device system may include a control element coupled to at least one elongate member of the plurality of elongate members to at least in part control a configuration of at least the at least one elongate member and the plurality of elongate members may wrap around at least a portion of the control element at least when the structure is in the delivery configuration.

In some embodiments, the medical device system may include a control element coupled to at least one elongate member of the plurality of elongate members to at least in part control a configuration of at least the at least one elongate member, and the particular portions of the plurality of elongate members may wrap around at least a portion of the control element at least when the structure is in the delivery configuration. In some embodiments, the particular portions of the plurality of elongate members may wrap around at least the portion of the control element when the structure is in the deployed configuration. In some embodiments the particular portions of the plurality of elongate members each may wrap around the control element along a same rotational direction at least when the structure is in the delivery configuration, the same rotational direction being a same clockwise direction or a same counterclockwise direction.

In some embodiments, a portion of a first elongate member of the plurality of elongate members may be nested with a portion of a second elongate member of the plurality of elongate members at least when the structure is in the delivery configuration. In some embodiments, the particular portion of each of at least a first elongate member of the plurality of elongate members may be nested with the particular portion of a second elongate member of the plurality of elongate members at least when the structure is in the delivery configuration.

In some embodiments, for each particular elongate member of the plurality of elongate members, the particular portion of the particular elongate member and the part of the particular elongate member that forms a respective part of the structure are provided by a plurality of portions of the particular elongate member arranged between a proximal portion of the particular elongate member and a distal end of the particular elongate member, the plurality of portions of the particular elongate member collectively providing a front surface of the particular elongate member and a back surface of the particular elongate member opposite across a thickness of the particular elongate member from the front surface of the particular elongate member. In some embodiments, at least a portion of the front surface of each particular elongate member of the plurality of elongate members faces outwardly from an interior of the structure when the structure is in the deployed configuration, and at least a contacting portion of the front surface of a first elongate member of the plurality of elongate members contacts at least a contacting portion of the back surface of a second elongate member of the plurality of elongate members when the structure is in the delivery configuration. In some embodiments, for each particular elongate member of the plurality of elongate members, the particular elongate member may include a flexible circuit structure extending between the proximal portion of the particular elongate member and the distal end of the particular elongate member, the flexible circuit structure including the particular portion of the particular elongate member. In some embodiments, at least the contacting portion of the front surface of the first elongate member may follow a contour of at least the contacting portion of the back surface of the second elongate member. In some embodiments, the contacting portion of the front surface of the first elongate member may be provided by the particular portion of the first elongate member, and the contacting portion of the back surface of the second elongate member may be provided by the particular portion of the second elongate member. In some embodiments, at least the contacting portion of the front surface of the first elongate member may follow the contour of at least the contacting portion of the back surface of the second elongate member throughout the at least 360 degrees of rotation of the helical configuration of the particular portion of the second elongate member.

In some embodiments, for each particular elongate member of the plurality of elongate members, the particular portion of the particular elongate member and the part of the particular elongate member that forms a respective part of the structure may be provided by a plurality of portions of the particular elongate member arranged between a proximal portion of the particular elongate member and a distal end of the particular elongate member, the plurality of portions of the particular elongate member collectively providing a front surface of the particular elongate member and a back surface of the particular elongate member opposite across a thickness of the particular elongate member from the front surface of the particular elongate member. In some embodiments, at least a portion of the front surface of each elongate member of the plurality of elongate members faces outwardly from an interior of the structure when the structure is in the deployed configuration, and at least the particular portions of a first set of at least three of the plurality of elongate members are arranged front surface-toward-back surface in a first stacked arrangement when the structure is in the delivery configuration. In some embodiments, at least the particular portions of the first set of at least three of the plurality of elongate members may be arranged front surface-toward-back surface in a second stacked arrangement when the structure is in the deployed configuration.

In some embodiments, each transducer set may be located on at least one portion of a respective one of the plurality of elongate members other than the particular portion of the respective one of the plurality of elongate members. In some embodiments, each particular elongate member of the plurality of elongate members includes a length between a proximal portion of the particular elongate member and a distal end of the particular elongate member, and the plurality of transducer sets may be located on distal portions of the plurality of elongate members, the distal portions closer, along the lengths of the elongate members, to the distal ends of the elongate members than the particular portions of the plurality of elongate members when the structure is in the delivery configuration. In some embodiments, the at least one portions of the plurality of elongate members may extend like lines of longitude about the structure when the structure is in the deployed configuration. In some embodiments, the at least one portion of each elongate member of the plurality of elongate members is not arranged in a helical configuration when the structure is in the delivery configuration. In some embodiments, the at least one portion of each elongate member of the plurality of elongate members is not arranged in a helical configuration when the structure is in the deployed configuration.

In some embodiments, the particular portions of a set of at least two elongate members of the plurality of elongate members may be arranged in a collective helical configuration when the structure is in the deployed configuration. In some embodiments, the particular portions of the set of at least two elongate members of the plurality of elongate members may extend along a same rotational direction in the collective helical configuration when the structure is in the delivery configuration, the same rotational direction being a same clockwise direction or a same counterclockwise direction.

In some embodiments, the helical configuration of the particular portion of a first elongate member of the plurality of elongate members may be axially offset from the helical configuration of the particular portion of at least a second elongate member of the plurality of elongate members when the structure is in the delivery configuration. In some embodiments, the particular portion of the first elongate member of the plurality of elongate members may extend along a same rotational direction as the particular portion of the second elongate member of the plurality of elongate members when the structure is in the delivery configuration, the same rotational direction being a same clockwise direction or a same counterclockwise direction.

In some embodiments, the medical device system may include a shaft member physically coupled to the plurality of elongate members, and a location at which the shaft member is physically coupled to each elongate member of the plurality of elongate members is fixed with respect to a shaft distal end of the shaft member. In some embodiments, the shaft member is configured to percutaneously deliver the structure to the bodily cavity at least in response to translation of at least part of the shaft member. In some embodiments, the shaft member includes a shaft proximal end, the shaft distal end, and an elongated portion extending between the shaft proximal end and the shaft distal end, and the particular portion of each elongate member of the plurality of elongate members is located within the elongated portion of the shaft member.

In some embodiments, the plurality of transducer sets may include a plurality of electrodes. In some embodiments, each transducer of each transducer set of the plurality of transducer sets may include a respective electrode.

In some embodiments, for each particular elongate member of the plurality of elongate members: the particular portion of the particular elongate member is between, along a length of the particular elongate member, (a) a proximal portion of the particular elongate member and (b) the part of the particular elongate member that forms a respective part of the structure, and the part of the particular elongate member is between the particular portion of the particular elongate member and a distal end of the particular elongate member along the length of the particular elongate member. The particular elongate member may be configured to be percutaneously advanced distal end of the particular elongate member ahead of at least the proximal portion of the particular elongate member when the structure is in the delivery configuration. A first width of the particular elongate member in the particular portion may be at least 10% less, or in some embodiments is between 20% and 60%, inclusive, less than a corresponding second width of the particular elongate member in the proximal portion of the particular elongate member.

In some embodiments, for each particular elongate member of the plurality of elongate members: the part of the particular elongate member, which forms a respective part of the structure, and the particular portion of the particular elongate member are provided by a plurality of portions of the particular elongate member arranged between a proximal portion of the particular elongate member and a distal end of the particular elongate member. The plurality of portions of the particular elongate member may collectively provide a front surface of the particular elongate member and a back surface of the particular elongate member opposite across a thickness of the particular elongate member from the front surface of the particular elongate member. The thickness of the particular elongate member may be perpendicular to a longitudinal axis of the particular elongate member. In some embodiments, for each particular elongate member of the plurality of elongate members: a first width of the particular elongate member in the particular portion of the particular elongate member is at least 10% less, or in some embodiments is between 20% and 60%, inclusive, less than a second width of the particular elongate member in the proximal portion of the particular elongate member. In some embodiments, each of the first width and the second width is perpendicular to the thickness and the longitudinal axis of the particular elongate member. In some embodiments, the first widths of the particular elongate members of the plurality of elongate members are equal or within 5% of a same width.

In some embodiments, for each particular elongate member of the plurality of elongate members: the proximal portion of the particular elongate member is adjacent the particular portion of the particular elongate member along the longitudinal axis of the particular elongate member, and, in a state where the longitudinal axis of the particular elongate member resides within a same plane. In some embodiments, the longitudinal axis of the particular elongate member bends by a bending angle between the proximal portion of the particular elongate member and the particular portion of the particular elongate member. An absolute value of the bending angle may be at least 5 degrees in some embodiments, or may be between 10 and 20 degrees, inclusive in some embodiments. In some embodiments, the bending angle for each elongate member in a first subset of at least two elongate members of the plurality of elongate members bends is positive, and the bending angle for each elongate member in a second subset of at least two elongate members of the plurality of elongate members bends is negative, in some embodiments, the elongate members in the first subset other than the elongate members in the second subset.

In some embodiments, various systems may include combinations and subsets of the systems summarized above.

In some embodiments, a medical device system may be summarized as including a plurality of transducer sets, each transducer set including one or more transducers positionable in a bodily cavity. The medical device system may include a plurality of elongate members, at least parts of the elongate members collectively forming a structure on which the plurality of transducers are located, each elongate member including at least a first portion on which a respective transducer set of the plurality of transducer sets of the transducers is located. The medical device system may include a shaft member physically coupled to the plurality of elongate members. In some embodiments, a location at which the shaft member is physically coupled to each elongate member of the plurality of elongate members is fixed with respect to a shaft distal end of the shaft member to deliver the structure through a bodily opening leading to a bodily cavity at least in response to translation of at least part of the shaft member. In some embodiments, the shaft member includes a shaft proximal end, the shaft distal end, and an elongated portion extending between the shaft proximal end and the shaft distal end. In some embodiments, each of the first portions of the plurality of elongate members may extend outwardly from the shaft distal end of the shaft member, and each elongate member may include a second portion located within the elongated portion of the shaft member, each second portion including a helical configuration.

In some embodiments, each second portion may include a helical configuration including at least 360 degrees of rotation. In some embodiments, each second portion may include a helical configuration including at least 540 degrees of rotation. In some embodiments, each second portion may include a helical configuration including at least 720 degrees of rotation.

In some embodiments, the structure may be selectively moveable between a delivery configuration in which the structure is sized to be percutaneously deliverable to the bodily cavity, and a deployed configuration in which the structure is sized too large to be percutaneously deliverable to the bodily cavity. In some embodiments, the second portions of a set of at least two elongate members of the plurality of elongate members may be arranged in a collective helical configuration when the structure is in the delivery configuration. In some embodiments, the second portions of a set of at least two elongate members of the plurality of elongate members may be arranged in a collective helical configuration when the structure is in the deployed configuration. In some embodiments, the first portions of the plurality of elongate members may be arranged in a configuration too large to be percutaneously deliverable to the bodily cavity when the structure is in the deployed configuration.

In some embodiments, no transducer is located on the second portion of each elongate member of the plurality of elongate members.

In some embodiments, the structure may be selectively moveable between a delivery configuration in which the structure is sized to be percutaneously deliverable to the bodily cavity, and a deployed configuration in which the structure is sized too large to be percutaneously deliverable to the bodily cavity. In some embodiments, the medical device system may include a control element coupled to at least one elongate member of the plurality of elongate members to at least in part control a configuration of at least the at least one elongate member. In some embodiments, the plurality of elongate members may wrap around at least a portion of the control element at least when the structure is in the delivery configuration.

In some embodiments, the structure may be selectively moveable between a delivery configuration in which the structure is sized to be percutaneously deliverable to the bodily cavity, and a deployed configuration in which the structure is sized too large to be percutaneously deliverable to the bodily cavity. In some embodiments, the medical device system may include a control element coupled to at least one elongate member of the plurality of elongate members to at least in part control a configuration of at least the at least one elongate member. In some embodiments, the second portions of the plurality of elongate members may wrap around at least a portion of the control element at least when the structure is in the delivery configuration. In some embodiments, the second portions of the plurality of elongate members may wrap around at least the portion of the control element when the structure is in the deployed configuration. In some embodiments, the second portions of the plurality of elongate members each may wrap around the control element along a same rotational direction at least when the structure is in the delivery configuration, the same rotational direction being a same clockwise direction or a same counterclockwise direction.

In some embodiments, the structure may be selectively moveable between a delivery configuration in which the structure is sized to be percutaneously deliverable to the bodily cavity, and a deployed configuration in which the structure is sized too large to be percutaneously deliverable to the bodily cavity. In some embodiments, the second portion of each of at least a first elongate member of the plurality of elongate members may be nested with the second portion of a second elongate member of the plurality of elongate members at least when the structure is in the delivery configuration.

In some embodiments, the structure may be selectively moveable between a delivery configuration in which the structure is sized to be percutaneously deliverable to the bodily cavity, and a deployed configuration in which the structure is sized too large to be percutaneously deliverable to the bodily cavity. In some embodiments, for each particular elongate member of the plurality of elongate members, the first portion of the particular elongate member and the second portion of the particular elongate member may be provided by a plurality of portions of the particular elongate member arranged between a proximal portion of the particular elongate member and a distal end of the particular elongate member, the plurality of portions of the particular elongate member collectively providing a front surface of the particular elongate member and a back surface of the particular elongate member opposite across a thickness of the particular elongate member from the front surface of the particular elongate member. In some embodiments, at least a portion of the front surface of each particular elongate member of the plurality of elongate members may face outwardly from an interior of the structure when the structure is in the deployed configuration, and at least a particular portion of the front surface of a first elongate member of the plurality of elongate members may face at least a particular portion of the back surface of a second elongate member of the plurality of elongate members when the structure is in the delivery configuration. In some embodiments, for each particular elongate member of the plurality of elongate members, the particular elongate member may include a flexible circuit structure extending between the proximal portion of the particular elongate member and the distal end of the particular elongate member, the flexible circuit structure including the second portion of the particular elongate member. In some embodiments, at least the particular portion of the front surface of the first elongate member may follow a contour of at least the particular portion of the back surface of the second elongate member at least when the structure is in the delivery configuration. In some embodiments, the particular portion of the front surface of the first elongate member may be provided by the second portion of the first elongate member, and the particular portion of the back surface of the second elongate member may be provided by the second portion of the second elongate member. In some embodiments, at least the particular portion of the front surface of the first elongate member may follow the contour of at least the particular portion of the back surface of the second elongate member throughout a helical rotation of the helical configuration of the second portion of the second elongate member.

In some embodiments, the structure may be selectively moveable between a delivery configuration in which the structure is sized to be percutaneously deliverable to the bodily cavity, and a deployed configuration in which the structure is sized too large to be percutaneously deliverable to the bodily cavity. In some embodiments, for each particular elongate member of the plurality of elongate members, the first portion of the particular elongate member and the second portion of the particular elongate member may be provided by a plurality of portions of the particular elongate member arranged between a proximal portion of the particular elongate member and a distal end of the particular elongate member, the plurality of portions of the particular elongate member collectively providing a front surface of the particular elongate member and a back surface of the particular elongate member opposite across a thickness of the particular elongate member from the front surface of the particular elongate member. In some embodiments at least a portion of the front surface of each elongate member of the plurality of elongate members may face outwardly from an interior of the structure when the structure is in the deployed configuration, and at least the second portions of a first set of at least three of the plurality of elongate members may be arranged front surface-toward-back surface in a first stacked arrangement when the structure is in the delivery configuration. In some embodiments, at least the second portions of the first set of at least three of the plurality of elongate members may be arranged front surface-toward-back surface in a second stacked arrangement when the structure is in the deployed configuration. In some embodiments, the first portions of a second set of at least three of the plurality of elongate members may be arranged front surface-toward-back surface in a second stacked arrangement when the structure is in the delivery configuration. In some embodiments, the second portions of a second set of at least three of the plurality of elongate members may be arranged front surface-toward-back surface in a second stacked arrangement when the structure is in the delivery configuration.

In some embodiments, the structure may be selectively moveable between a delivery configuration in which the structure is sized to be percutaneously deliverable to the bodily cavity, and a deployed configuration in which the structure is sized too large to be percutaneously deliverable to the bodily cavity. In some embodiments, the first portions of the plurality of elongate members may extend like lines of longitude about the structure when the structure is in the deployed configuration. In some embodiments, the first portion of each elongate member of the plurality of elongate members is not arranged in a helical configuration when the structure is in the delivery configuration.

In some embodiments, the structure may be selectively moveable between a delivery configuration in which the structure is sized to be percutaneously deliverable to the bodily cavity, and a deployed configuration in which the structure is sized too large to be percutaneously deliverable to the bodily cavity. In some embodiments, the second portions of a set of at least two elongate members of the plurality of elongate members are arranged in a collective helical configuration when the structure is in the delivery configuration. In some embodiments, the first portion of each elongate member of the plurality of elongate members is not arranged in a helical configuration when the structure is in the deployed configuration. In some embodiments, the second portions of the set of at least two elongate members of the plurality of elongate members may extend along a same rotational direction in the collective helical configuration when the structure is in the delivery configuration, the same rotational direction being a same clockwise direction or a same counterclockwise direction.

In some embodiments, the structure may be selectively moveable between a delivery configuration in which the structure is sized to be percutaneously deliverable to the bodily cavity, and a deployed configuration in which the structure is sized too large to be percutaneously deliverable to the bodily cavity. In some embodiments, the helical configuration of the second portion of a first elongate member of the plurality of elongate members may be axially offset from the helical configuration of the second portion of at least a second elongate member of the plurality of elongate members when the structure is in the delivery configuration. In some embodiments, the second portion of the first elongate member of the plurality of elongate members may extend along a same rotational direction as the second portion of the second elongate member of the plurality of elongate members when the structure is in the delivery configuration, the same rotational direction being a same clockwise direction or a same counterclockwise direction.

In some embodiments, the plurality of transducers may include a plurality of electrodes. In some embodiments, each transducer of the plurality of transducers may include a respective electrode.

In some embodiments, wherein, for each particular elongate member of the plurality of elongate members: the second portion of the particular elongate member is between a proximal portion of the particular elongate member and the first portion of the particular elongate member along a length of the particular elongate member, and the first portion of the particular elongate member is between the second portion of the particular elongate member and a distal end of the particular elongate member along the length of the particular elongate member. The particular elongate member may be configured to be percutaneously advanced distal end of the particular elongate member ahead of at least the proximal portion of the particular elongate member when the structure is in the delivery configuration. In some embodiments, a first width of the particular elongate member in the second portion is at least 10% less than a corresponding second width of the particular elongate member in the proximal portion of the particular elongate member. In some embodiments, the first width of the particular elongate member in the second portion is between 20% and 60%, inclusive, less than the corresponding second width of the particular elongate member in the proximal portion of the particular elongate member.

In some embodiments, wherein, for each particular elongate member of the plurality of elongate members: the first portion of the particular elongate member and the second portion of the particular elongate member are provided by a plurality of portions of the particular elongate member arranged between a proximal portion of the particular elongate member and a distal end of the particular elongate member. The plurality of portions of the particular elongate member may collectively provide a front surface of the particular elongate member and a back surface of the particular elongate member opposite across a thickness of the particular elongate member from the front surface of the particular elongate member, and the thickness of the particular elongate member may be perpendicular to a longitudinal axis of the particular elongate member. In some embodiments, wherein, for each particular elongate member of the plurality of elongate members: a first width of the particular elongate member in the second portion of the particular elongate member is at least 10% less, or in some embodiments is between 20% and 60%, inclusive, less than a second width of the particular elongate member in the proximal portion of the particular elongate member, and each of the first width and the second width is perpendicular to the thickness and the longitudinal axis of the particular elongate member. In some embodiments, the first widths of the particular elongate members of the plurality of elongate members are equal or within 5% of a same width. In some embodiments, wherein, for each particular elongate member of the plurality of elongate members: the proximal portion of the particular elongate member is adjacent the second portion of the particular elongate member along the longitudinal axis of the particular elongate member, and, in a state where the longitudinal axis of the particular elongate member resides within a same plane, the longitudinal axis of the particular elongate member bends by a bending angle between the proximal portion of the particular elongate member and the second portion of the particular elongate member, an absolute value of the bending angle being at least 5 degrees, in some embodiments, and being between 10 and 20 degrees, inclusive, in some embodiments. In some embodiments, the bending angle for each elongate member in a first subset of at least two elongate members of the plurality of elongate members is positive, and the bending angle for each elongate member in a second subset of at least two elongate members of the plurality of elongate members is negative, the elongate members in the first subset other than the elongate members in the second subset.

In some embodiments, various systems may include combinations and subsets of the systems summarized above.

In some embodiments, a medical device system may be summarized as including a plurality of transducer sets, each transducer set including one or more transducers positionable in a bodily cavity; a plurality of elongate members, at least parts of the elongate members collectively forming a structure on which the plurality of transducers are located, each elongate member comprising at least a first portion on which a respective transducer set of the plurality of transducer sets of the transducers is located, and a shaft member physically coupled to the plurality of elongate members, a location at which the shaft member is physically coupled to each elongate member of the plurality of elongate members is fixed with respect to a shaft distal end of the shaft member to deliver the structure through a bodily opening leading to a bodily cavity at least in response to translation of at least part of the shaft member, the shaft member including a shaft proximal end, the shaft distal end, and an elongated portion extending between the shaft proximal end and the shaft distal end, wherein each of the first portions of the plurality of elongate members extends outwardly from the shaft distal end of the shaft member, and wherein each elongate member comprises a second portion located within the elongated portion of the shaft member, each second portion comprising a twisted, non-helical configuration including at least 360 degrees of rotation.

In some embodiments, each second portion includes a twisted, non-helical configuration including at least 540 degrees of rotation. In some embodiments, each second portion includes a twisted, non-helical configuration including at least 720 degrees of rotation.

In some embodiments, the shaft member includes a shaft proximal end, the shaft distal end, and a longitudinal axis extending between the shaft proximal end and the shaft distal end. Each second portion may be intersected by the longitudinal axis.

In some embodiments, no transducer is located on the second portion of each elongate member of the plurality of elongate members.

In some embodiments, the plurality of transducers includes a plurality of electrodes.

In some embodiments, each of the plurality of transducers comprises a respective electrode.

In some embodiments, the structure is selectively moveable between: a delivery configuration in which the structure is sized to be percutaneously deliverable to the bodily cavity, and a deployed configuration in which the structure is sized too large to be percutaneously deliverable to the bodily cavity.

In some embodiments, the second portions of a set of at least two elongate members of the plurality of elongate members are arranged in a collective twisted, non-helical configuration when the structure is in the delivery configuration. The second portions of the set of at least two elongate members of the plurality of elongate members may extend along a same rotational direction in the collective twisted, non-helical configuration when the structure is in the delivery configuration, the same rotational direction being a same clockwise direction or a same counterclockwise direction in some embodiments.

In some embodiments, the second portions of a set of at least two elongate members of the plurality of elongate members are arranged in a collective twisted, non-helical configuration when the structure is in the deployed configuration.

In some embodiments, the first portions of the plurality of elongate members are arranged in a configuration too large to be percutaneously deliverable to the bodily cavity when the structure is in the deployed configuration.

In some embodiments, the second portion of each of at least a first elongate member of the plurality of elongate members is nested with the second portion of a second elongate member of the plurality of elongate members at least when the structure is in the delivery configuration.

In some embodiments, wherein, for each particular elongate member of the plurality of elongate members, the first portion of the particular elongate member and the second portion of the particular elongate member are provided by a plurality of portions of the particular elongate member arranged between a proximal portion of the particular elongate member and a distal end of the particular elongate member, the plurality of portions of the particular elongate member collectively providing a front surface of the particular elongate member and a back surface of the particular elongate member opposite across a thickness of the particular elongate member from the front surface of the particular elongate member. At least a portion of the front surface of each particular elongate member of the plurality of elongate members may face outwardly from an interior of the structure when the structure is in the deployed configuration, and at least a particular portion of the front surface of a first elongate member of the plurality of elongate members may face at least a particular portion of the back surface of a second elongate member of the plurality of elongate members when the structure is in the delivery configuration. In some embodiments, wherein, for each particular elongate member of the plurality of elongate members, the particular elongate member includes a flexible circuit structure extending between the proximal portion of the particular elongate member and the distal end of the particular elongate member, the flexible circuit structure including the second portion of the particular elongate member. In some embodiments, at least the particular portion of the front surface of the first elongate member follows a contour of at least the particular portion of the back surface of the second elongate member at least when the structure is in the delivery configuration. In some embodiments, the particular portion of the front surface of the first elongate member is provided by the second portion of the first elongate member, and the particular portion of the back surface of the second elongate member is provided by the second portion of the second elongate member. In some embodiments, at least the particular portion of the front surface of the first elongate member follows the contour of at least the particular portion of the back surface of the second elongate member throughout a rotation of the twisted, non-helical configuration of the second portion of the second elongate member.

In some embodiments, wherein, for each particular elongate member of the plurality of elongate members, the first portion of the particular elongate member and the second portion of the particular elongate member are provided by a plurality of portions of the particular elongate member arranged between a proximal portion of the particular elongate member and a distal end of the particular elongate member, the plurality of portions of the particular elongate member collectively providing a front surface of the particular elongate member and a back surface of the particular elongate member opposite across a thickness of the particular elongate member from the front surface of the particular elongate member. At least a portion of the front surface of each elongate member of the plurality of elongate members may face outwardly from an interior of the structure when the structure is in the deployed configuration, and at least the second portions of a first set of at least three of the plurality of elongate members may be arranged front surface-toward-back surface in a first stacked arrangement when the structure is in the delivery configuration. In some embodiments, at least the second portions of the first set of at least three of the plurality of elongate members are arranged front surface-toward-back surface in a second stacked arrangement when the structure is in the deployed configuration. In some embodiments, the first portions of the first set of at least three of the plurality of elongate members are arranged front surface-toward-back surface in a second stacked arrangement when the structure is in the delivery configuration.

In some embodiments, the first portions of the plurality of elongate members extend like lines of longitude about the structure when the structure is in the deployed configuration.

In some embodiments, the first portion of each elongate member of the plurality of elongate members is not arranged in a twisted, non-helical configuration including at least 360 degrees of rotation when the structure is in the delivery configuration.

In some embodiments, various systems may include combinations and subsets of the systems summarized above.

Various embodiments of the present invention may include systems, devices, or machines that are or include combinations or subsets of any one or more of the systems, devices, or machines and associated features thereof described herein.

Further, all or part of any one or more of the systems, devices, or machines discussed herein or combinations or sub-combinations thereof may implement or execute all or part of any one or more of the processes or methods discussed herein or combinations or sub-combinations thereof.

Any of the features of all or part of any one or more of the methods or processes discussed herein may be combined with any of the other features of all or part of any one or more of the methods and processes discussed herein. In addition, a computer program product may be provided that comprises program code portions for performing some or all of any one or more of the methods or processes and associated features thereof described herein, when the computer program product is executed by a computer or other computing device or device system. Such a computer program product may be stored on one or more computer-readable storage mediums, also referred to as one or more computer-readable data storage mediums.

In some embodiments, each of any of one or more of the computer-readable data storage medium systems (also referred to as processor-accessible memory device systems) described herein is a non-transitory computer-readable (or processor-accessible) data storage medium system (or memory device system) including or consisting of one or more non-transitory computer-readable (or processor-accessible) storage mediums (or memory devices) storing the respective program(s) which may configure a data processing device system to execute some or all of any of one or more of the methods or processes described herein.

Further, any of one or more of the methods or processes and associated features thereof discussed herein may be implemented or executed by all or part of a device system, apparatus, or machine, such as all or a part of any of one or more of the systems, apparatuses, or machines described herein or a combination or sub-combination thereof.

BRIEF DESCRIPTION OF THE DRAWINGS

It is to be understood that the attached drawings are for purposes of illustrating aspects of various embodiments and may include elements that are not to scale.

DETAILED DESCRIPTION

Figure 1:
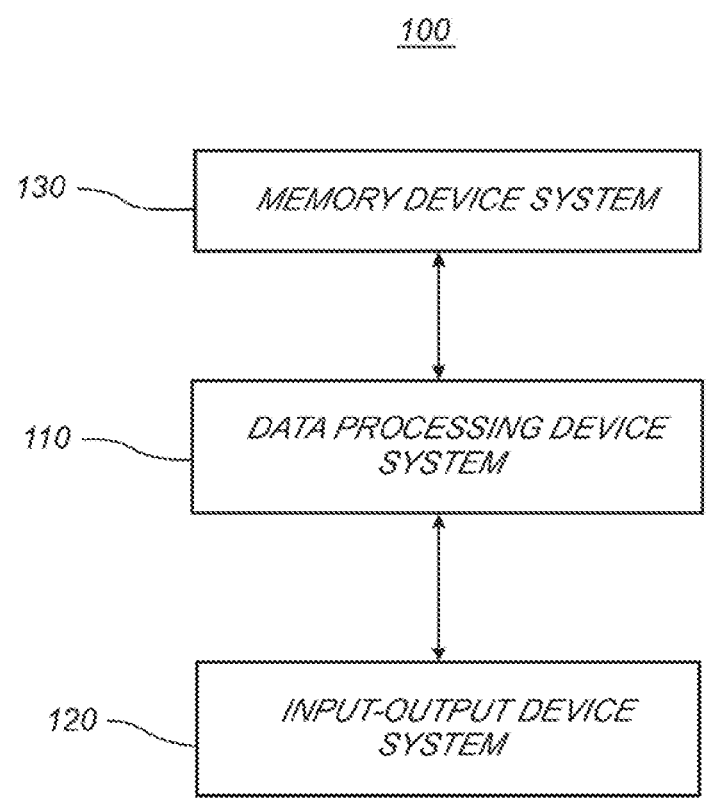
FIG. 1 is a schematic representation of a medical device system according to various example embodiments, where the medical device system may include a data processing device system, an input-output device system, and a memory device system, according to some embodiments.

Some embodiments of the present invention pertain at least to medical systems or medical device systems including elongate members, various portions thereof arranged to form various structures. In some embodiments, such a structure is manipulable to change size, shape or both size and shape thereof. In various embodiments, such a structure is selectively moveable between a delivery configuration, in which the structure is suitably sized to be percutaneously or intravascularly deliverable to a bodily cavity, and a deployed or expanded configuration, in which the structure is sized too large to be percutaneously or intravascularly deliverable to the bodily cavity. In some embodiments, medical device systems include various elongate members, some particular portions (e.g., first particular portions) of each of the elongate members form a structure that is selectively moveable between a first configuration, in which the structure or the some particular portions are suitably sized to be percutaneously or intravascularly deliverable to a bodily cavity, and a second configuration, in which the structure or the some particular portions are sized too large to be percutaneously or intravascularly deliverable to the bodily cavity. In some embodiments, transducer sets (e.g., electrode sets) are located on the first particular portions of at least some of the elongate members. According to some embodiments, at least some of the transducers may be selectively operable to transmit energy (e.g., energy sufficient to ablate tissue).

In some embodiments, the various elongate members include portions (e.g., second particular portions) other than the first particular portions described above. In some embodiments, each of the second particular portions of the various elongate members may be arranged in a helical configuration or a twisted, non-helical configuration at least when the structure is in a state in which the structure is suitably sized to be percutaneously or intravascularly deliverable to a bodily cavity. As discussed in more detail below and according to some embodiments, such a helical configuration or twisted, non-helical configuration improves bending characteristics and flexibility of the elongate members, thereby improving the ease by which the structure can be delivered through tortuous paths through various vessels in a body and by which the structure can be positioned in a bodily cavity. In some embodiments, each helical or twisted, non-helical configuration includes 360 degrees of rotation or more. In some embodiments, each helical or twisted, non-helical configuration includes 540 degrees of rotation or more. In some embodiments, each helical or twisted, non-helical configuration includes 720 degrees of rotation or more. In some embodiments, the second particular portions of the various elongate members are arranged in a collective helical configuration or twisted, non-helical configuration at least when the structure is in a state in which the structure is suitably sized to be percutaneously or intravascularly deliverable to a bodily cavity. In some embodiments, the second particular portions are located within a catheter shaft member to which the structure is physically coupled. As described in further detail below, in various embodiments, the helical configurations or twisted, non-helical configurations that are comprised by the second particular portions of the elongate members allow the structure or at least other particular portions of the elongate members to (a) better negotiate a tortuous path through a bodily opening leading to a bodily cavity or (b) provide enhanced positioning of the structure or various parts of the elongate members within the bodily cavity.

In the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects. In addition, unless otherwise explicitly noted or required by context, the word "subset" is intended to mean a set having the same elements as or fewer elements than the subset's parent or superset.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'based at least on A' includes A as well as the possibility of one or more other additional elements besides A. In the same manner, the phrase, 'based on A' includes A, as well as the possibility of one or more other additional elements besides A. However, the phrase, 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device", the word "machine", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various embodiments that a device or machine or device system resides entirely within a same housing to exclude embodiments where the respective device, machine, or device system resides across different housings. The word "device" may equivalently be referred to as a "device system" in some embodiments.

Further, the phrase "in response to" may be used in this disclosure. For example, this phrase may be used in the following context, where an event A occurs in response to the occurrence of an event B. In this regard, such phrase includes, for example, that at least the occurrence of the event B causes or triggers the event A.

In some embodiments, the term "adjacent", the term "proximate", and the like refer at least to a sufficient closeness between the objects defined as adjacent, proximate, or the like, to allow the objects to interact in a designated way. For example, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", and the like additionally or alternatively refers to objects that do not have another substantially similar object between them. For example, object A and object B could be considered adjacent or proximate if they contact each other (and, thus, it could be considered that no other object is between them), or if they do not contact each other but no other object that is substantially similar to object A, object B, or both objects A and B, depending on the embodiment, is between them. In some embodiments, the term "adjacent", the term "proximate", and the like additionally or alternatively refers to at least a sufficient closeness between the objects defined as adjacent, proximate, and the like, the sufficient closeness being within a range that does not place any one or more of the objects into a different or dissimilar region, or does not change an intended function of any one or more of the objects or of an encompassing object that includes a set of the objects. Different embodiments of the present invention adopt different ones or combinations of the above definitions. Of course, however, the term "adjacent", the term "proximate", and the like are not limited to any of the above example definitions, according to some embodiments. In addition, the term "adjacent" and the term "proximate" do not have the same definition, according to some embodiments.

The phrase "physically coupled" is intended to include, in some embodiments, a coupling between two objects that involves a coupling between the two objects that may restrict some form of movement (e.g., translation or rotation or both translation and rotation) therebetween. In some embodiments, the two objects physically contact each other at least in one state of the physical coupling between the two objects. In some embodiments, the two objects do not directly physically contact each other at least in one state of the physical coupling between the two objects (e.g., a coupler or other coupling member positioned between the two objects to couple them together). The phrase "rotationally coupled" is intended to include, in some embodiments, a coupling between two objects that allows for at least some rotational movement between the two objects. The phrase "translationally coupled" is intended to include, in some embodiments, a coupling between two objects that allows for some form of translational movement between the two objects. The phrases "fixedly coupled", "permanently coupled", and the like, are intended to include, in some embodiments, a secure coupling between two objects that, in some embodiments, does not involve or include a mechanism configured to release the coupling of the two objects. The phrases "removably coupled", "detachably coupled", and the like, are intended to include, in some embodiments, a coupling between two objects that, in some embodiments, allows such coupling to be repeatedly disengaged and re-engaged without damaging the coupling (if a distinct coupling mechanism exists, e.g., in contrast to an interference fit that relies on friction), without damaging either or both of the objects, or without damaging the coupling (if a distinct coupling mechanism exists) and without damaging either or both of the objects. The phrase "operatively coupled" is intended to include, for example, a coupling between two objects that transmits force, energy, information, or other influence at least from one of the two objects to the other of the two objects. An operative coupling does not exclude the possibility of a physical or fixed coupling in addition to the operative coupling. Unless otherwise explicitly noted or required by context, for any connection or coupling, direct or indirect, between components, devices, or other physical objects described herein, different embodiments include different ones of the above-described coupling types for such components, devices, or other physical objects. For example, unless otherwise explicitly noted or required by context, if a first physical object is shown in the figures or described in this text as being connected or coupled, directly or indirectly, to a second physical object; some embodiments will have the first physical object fixedly coupled to the second physical object; other embodiments will have the first physical object rotationally coupled to the second physical object; other embodiments will have the first physical object translationally coupled to the second physical object; other embodiments will have the first physical object permanently coupled to the second physical object; other embodiments will have the first physical object removably or detachably coupled to the second physical object; other embodiments will have the first physical object not fixedly or permanently coupled to the second physical object while having the first physical object physically coupled to the second physical object; other embodiments will have the first physical object not physically coupled or fixedly coupled to the second physical object, but will have the first physical object operatively coupled to the second physical object; etc.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In some embodiments, the word "fluid" may include fluid that is not inherent to the bodily cavity, such as saline or other fluid that might be artificially introduced into the bodily cavity. In some embodiments, the word "fluid" may include a fluid that may be artificially introduced into the bodily cavity without the fluid coming into direct contact with tissue or a naturally occurring bodily fluid (e.g., a fluid employed in various cryogenic ablation procedures). In the case of cardiac applications, fluid such as blood will flow into and out of various intra-cardiac cavities (e.g., a left atrium or right atrium).

The phrase "bodily opening" as used in this disclosure should be understood to include a naturally occurring bodily opening or channel or lumen; a bodily opening or channel or lumen formed by an instrument or tool using techniques that may include, but are not limited to, mechanical, thermal, electrical, chemical, and exposure or illumination techniques; a bodily opening or channel or lumen formed by trauma to a body; or various combinations of one or more of the above or other bodily openings. Various elements having respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body. The bodily cavity may be a cavity provided in a bodily organ (e.g., an intra-cardiac cavity or chamber of a heart). A bodily opening may be provided as a passageway to a bodily cavity in some embodiments. A bodily cavity may be provided by a bodily opening in some embodiments.

The word "tissue" may be used in this disclosure, and tissue may include non-fluidic tissue and fluidic tissue. Non-fluidic tissue generally (or predominantly) has solid-like properties, such as tissue that forms a surface of a body or a surface within a bodily cavity, a surface of an anatomical feature or a surface of a feature associated with a bodily opening positioned in fluid communication with the bodily cavity. Non-fluidic tissue may include part or all of a tissue wall or membrane that defines a surface of the bodily cavity. In this regard, the tissue may form an interior surface of the cavity that at least partially surrounds a fluid within the cavity. In the case of cardiac applications, non-fluidic tissue may include tissue used to form an interior surface of an intra-cardiac cavity such as a left atrium or right atrium. Fluidic tissue, on the other hand, generally (or predominantly) has fluid-like properties (as compared to solid-like properties). An example of fluidic tissue is blood. In this regard, it should be noted that fluidic tissue may have some solid-like component(s) (e.g., fluidic tissue may include solid-like components), and non-fluidic tissue may have some fluid-like component(s) (e.g., non-fluidic tissue may include fluidic tissue within it). Unless otherwise explicitly noted or required by context, the word "tissue" should include non-fluidic tissue and fluidic tissue. However, some contexts where the word "tissue" would not include fluidic tissue are when tissue ablation is discussed, and ablation of fluidic tissue could be undesired, as discussed below. In various embodiments, non-fluidic tissue does not include excised tissue.

The word "ablation" as used in this disclosure should be understood to include any disruption to certain properties of tissue. Most commonly, the disruption is to the electrical conductivity of tissue and may be achieved by heating, which may be generated with resistive or radio-frequency (RF) techniques for example. Other properties of tissue, such as mechanical or chemical, and other means of disruption, such as optical or the use of cryogenic fluids are included when the term "ablation" is used. In some embodiments, electroporation techniques are included when the term "ablation" is used. In some embodiments, ablative power levels may be within the range of 3 W to 5 W (as compared, e.g., to a non-tissue-ablative power level range of 50 mW to 60 mW that may be used for typical impedance determinations). In some embodiments, ratios of employed ablative power levels to employed non-tissue-ablative power levels (e.g., used for typical impedance determinations) may be: at least equal to or greater than 50:1 in various embodiments; at least greater than 60:1 in some embodiments; at least greater than 80:1 in other various embodiments; and at least greater than 100:1 in yet other embodiments. In some embodiments, systems are configured to perform ablation of non-fluidic tissue while avoiding the delivery of excessive energy to fluidic tissue because energy that is sufficient to ablate non-fluidic tissue may also impact fluidic tissue in some circumstances. For example, energy that is sufficient to ablate non-fluidic tissue, in some circumstances, may cause blood (an example of fluidic tissue) to coagulate. In these and other embodiments where ablative energy transferred to fluidic tissue is not desired, it should be understood that any statement or reference to the 'ablation of tissue' or the like in these contexts is intended to refer to ablation of non-fluidic tissue, as opposed to ablation of fluidic tissue.

The term "transducer" as used in this disclosure should be interpreted broadly as any device capable, for example, of distinguishing between fluid and non-fluidic tissue, sensing temperature, creating heat, ablating tissue and measuring electrical activity of a tissue surface, stimulating tissue or any combination thereof. A transducer may convert input energy of one form into output energy of another form. Without limitation, a transducer may include an electrode, and references to a "transducer" herein may be replaced with "electrode" according to some embodiments. Without limitation, a transducer may include an electrode or a sensing device, or both an electrode and a sensing device. An electrode, in some embodiments, may be configured at least as a sensing device. Because a transducer may include an electrode according to various embodiments, any reference herein to a transducer may also imply a reference to an electrode, or vice versa. A transducer may be constructed from several parts, which may be discrete components or may be integrally formed. In some embodiments, an ablative element configured to apply energy sufficient for tissue ablation may be provided at least in part by a transducer.

The phrase "derivative thereof" and the like is or may be used herein at times in the context of a derivative of data or information merely to emphasize the possibility that such data or information may be modified or subject to one or more operations. For example, if a device generates first data for display, the process of converting the generated first data into a format capable of being displayed may alter the first data. This altered form of the first data may be considered a derivative of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information or data herein is intended to include these and like changes, regardless of whether or not the phrase "derivative thereof" or the like is used in reference to the information or data, unless otherwise required by context. As indicated above, usage of the phrase "or a derivative thereof" or the like merely emphasizes the possibility of such changes. Accordingly, the addition of or deletion of the phrase "or a derivative thereof" or the like should have no impact on the interpretation of the respective data or information. For example, the above-discussed color-coded bar chart may be considered a derivative of the respective first data or may be considered the respective first data itself.

The term "program" in this disclosure should be interpreted as a set of instructions or modules that may be executed by one or more components in a system, such as a controller system or data processing device system, in order to cause the system to perform one or more operations. The set of instructions or modules may be stored by any kind of memory device, such as those described subsequently with respect to the memory device system 130, 330, or both, shown in FIGS. 1, 3A, and 3B, respectively. In addition, this disclosure may describe or similarly describe that the instructions or modules of a program are configured to cause the performance of an action. The phrase "configured to" in this context is intended to include at least (a) instructions or modules that are presently in a form executable by one or more data processing devices to cause performance of the action (e.g., in the case where the instructions or modules are in a compiled and unencrypted form ready for execution), and (b) instructions or modules that are presently in a form not executable by the one or more data processing devices, but could be translated into a particular form executable by the one or more data processing devices to cause performance of the action (e.g., in the case where the instructions or modules are encrypted in a non-executable manner, but through performance of a decryption process, would be translated into a form ready for execution). Such descriptions should be deemed to be equivalent to describing that the instructions or modules are configured to cause the performance of the action. The word "module" may be defined as a set of instructions. The word "program" and the word "module" may each be interpreted to include multiple sub-programs or multiple sub-modules, respectively. In this regard, reference to a program or a module may be considered to refer to multiple programs or multiple modules.

Further, it is understood that information or data may be operated upon, manipulated, or converted into different forms as it moves through various devices or workflows. In this regard, unless otherwise explicitly noted or required by context, it is intended that any reference herein to information or data includes modifications to that information or data. For example, "data X" may be encrypted for transmission, and a reference to "data X" is intended to include both its encrypted and unencrypted forms, unless otherwise required or indicated by context. For another example, "image information Y" may undergo a noise filtering process, and a reference to "image information Y" is intended to include both the pre-processed form and the noise-filtered form, unless otherwise required or indicated by context. In other words, both the pre-processed form and the noise-filtered form are considered to be "image information Y", unless otherwise required or indicated by context. In order to stress this point, the phrase "or a derivative thereof" or the like may be used herein. Continuing the preceding example, the phrase "image information Y or a derivative thereof" refers to both the pre-processed form and the noise-filtered form of "image information Y", unless otherwise required or indicated by context, with the noise-filtered form potentially being considered a derivative of "image information Y". However, non-usage of the phrase "or a derivative thereof" or the like nonetheless includes derivatives or modifications of information or data just as usage of such a phrase does, as such a phrase, when used, is merely used for emphasis.

The term "helical" in this disclosure should be interpreted as having the form of a helix, in some embodiments, or, in some embodiments, a progressive winding around a three-dimensional shape like, for example, a wire wound around a cylinder in some embodiments, or a cone in some embodiments, or some other shape in other embodiments, in a corkscrew-like or screw thread-like manner. Unlike spiral or volute forms confined to a single plane, the term "helical" in this disclosure should be interpreted as exhibiting the rotational characteristic of a helix, where the rotation occurs about an axis (e.g., a longitudinal axis) of a three dimensional shape as the rotation extends along the axis, like the example of a wire winding progressively around a cylinder and the cylinder's longitudinal axis. In this regard, the axis may be referred to as the rotational axis of the helical object. In addition, the term "helical" in this disclosure should be interpreted as exhibiting the rotational characteristic of a helix, where the rotation is spaced from the axis (e.g., the longitudinal axis) of the three dimensional shape around which the rotation winds. In this regard, in some embodiments, it is considered that a longitudinal axis of a three dimensional shape about which the rotation occurs is located at a center of each successive cross-section of the three dimensional shape along the longitudinal direction of the three dimensional shape. Accordingly, the longitudinal axis may be considered to be the rotational axis (or axis of rotation) of the helical object and may be considered to bend with the three dimensional shape, for example, in the case of a long, narrow tube that bends, where the longitudinal axis of the long, narrow tube bends with the bending of the long, narrow tube.

The phrase, "twisted, non-helical" and similar phrases used in this disclosure should be interpreted as a twisting that intersects its rotational axis (or axis of rotation). In other words, a "twisted, non-helical" rotation occurs about a rotational axis, but intersects the rotational axis, whereas a helical rotation occurs about a rotational axis, but is spaced from and does not intersect the rotational axis. As with the above discussion regarding the rotational axis of a helical object possibly bending in some embodiments, the rotational axis of a twisted, non-helical configuration may also bend in some embodiments.

FIG. 1 schematically illustrates at least part of a medical device system 100 according to some embodiments. In some embodiments, the medical device system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as those in the system 100, methods of various embodiments that may be employed by various aspects described in this disclosure. Each of the phrases "data processing device", "data processor", "processor", and "computer" and the like is intended to include any data processing device, such as a central processing unit ("CPU"), a desktop computer, a laptop computer, a mainframe computer, a tablet computer such as an iPad (Trademark Apple Inc., Cupertino Calif.), a personal digital assistant, a cellular phone, a smartphone, or any other device for processing data, managing data, or handling data, whether implemented with electrical, magnetic, optical, biological components, or otherwise.

The memory device system 130 includes one or more processor-accessible memory devices configured to store information, including the information needed to execute the methods associated with various embodiments. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" and the like is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include or be a processor-accessible (or computer-readable) data storage medium. In some embodiments, each of the phrases "processor-accessible memory" and "processor-accessible memory device" is intended to include or be a non-transitory processor-accessible (or computer-readable) data storage medium. In some embodiments, the processor-accessible memory device system 130 may be considered to include or be a non-transitory processor-accessible (or computer-readable) data storage medium system. And, in some embodiments, the memory device system 130 may be considered to include or be a non-transitory processor-accessible (or computer-readable) storage medium system or data storage medium system including or consisting of one or more non-transitory processor-accessible (or computer-readable) storage or data storage mediums.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing device system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 may be implemented by a single application-specific integrated circuit (ASIC) in some embodiments.

The input-output device system 120 may include a mouse, a keyboard, a touch screen, another computer, or any device or combination of devices from which a desired selection, desired information, desired instructions, or any other desired data is input to the data processing device system 110. The input-output device system 120 may include a user-activatable control system that is responsive to a user action, such as actions from a care provider such as a physician or technician. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion of a medical system, transducer-based device system, or an electrode-based device system described herein. The phrase "transducer-based device system" is intended to include one or more physical devices or systems that include various transducers. Similarly, the phrase "electrode-based device system" is intended to include one or more physical devices or systems that include various electrodes. In this regard, the phrases "transducer-based device system" and "electrode-based device system" may be used interchangeably in accordance with various embodiments. Similarly, the phrases "transducer-based device" and "electrode-based device" may be used interchangeably in accordance with various embodiments.

The input-output device system 120 also may include an image-generating device system, a display device system, a speaker device system, a processor-accessible memory device system, or any device or combination of devices to which information, instructions, or any other data is output from the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system may include various other devices or systems described in various embodiments.

Figure 2A:
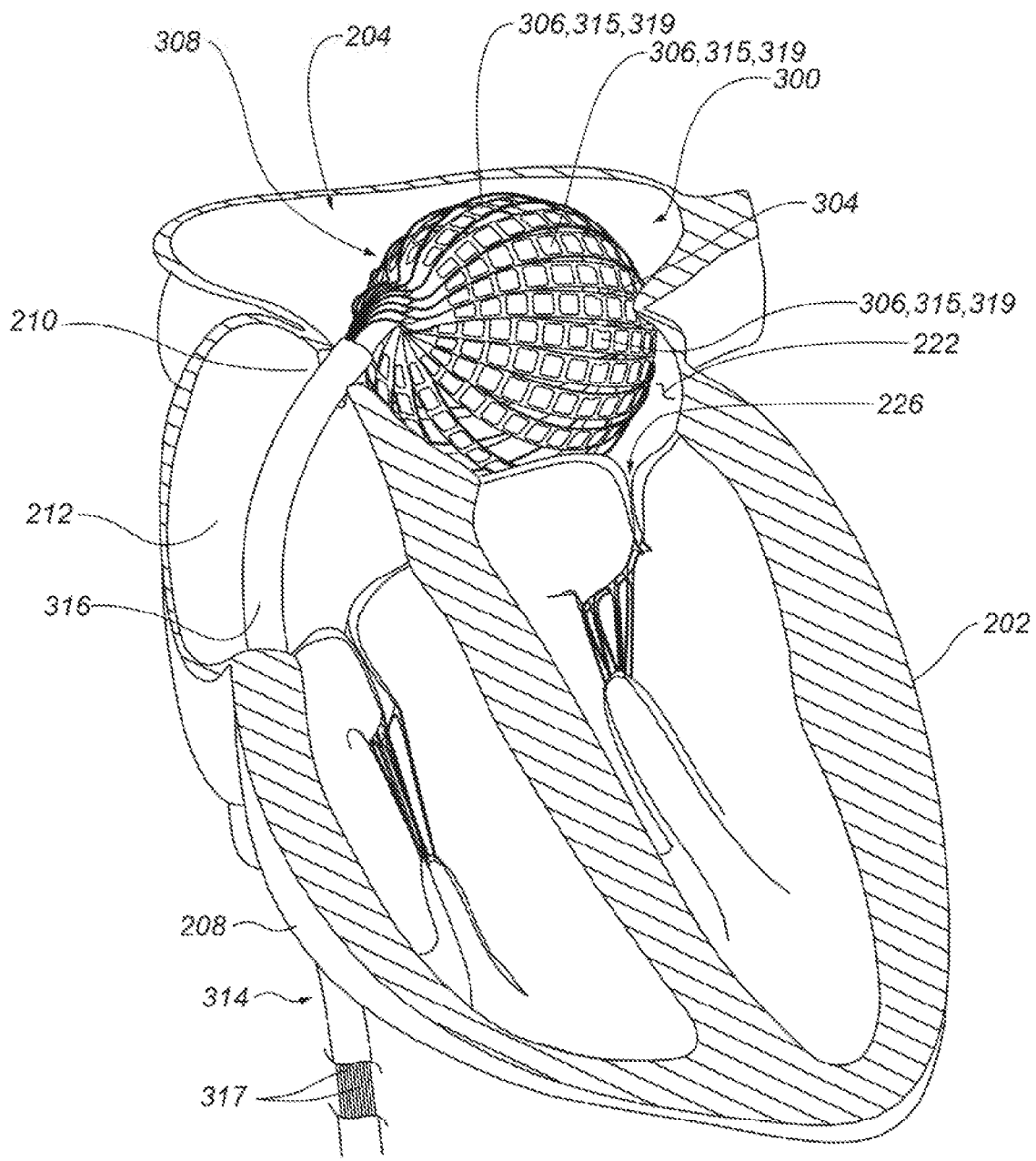
FIG. 2A is a cutaway diagram of a heart showing an electrode-based device system percutaneously placed in a left atrium of the heart in one particular orientation according to various example embodiments, the electrode-based device system optionally being part of the input-output device system of FIG. 1, according to some embodiments.

FIG. 2A shows an electrode-based device system 300, which may be all or part of a medical system or medical device system, and which may be included in the input-output device system 120 of FIG. 1, according to some embodiments. Because, as described in more detail below with respect to FIG. 4, electrodes may be part of transducers, according to some embodiments, the system 300 may also be considered a transducer-based device system in some embodiments.

Such a system 300 may be beneficial for, among other things, investigating or treating a bodily organ, for example, a heart 202, according to some example embodiments. The electrode-based device system 300 may include a frame or structure 308 that may be percutaneously or intravascularly inserted into a portion of the heart 202, such as an intracardiac cavity like left atrium 204. In some embodiments, the structure 308 is formed at least by a plurality of elongate members 304 (two called out in FIG. 2A) which provide the transducers 306. Although the embodiments associated with FIGS. 2A, 2B, 3A, 3B, and 3C show embodiments of systems 300 with ten elongate members 304, different embodiments may have different numbers of elongate members 304. For example, embodiments associated with FIGS. 3G, 3H, 3K, and 3L show embodiments of system 300 with eight elongate members 304.

Returning to the example of FIG. 2A, the electrode-based device system 300 includes catheter 314 inserted via the inferior vena cava 208 and penetrating through a bodily opening in transatrial septum 210 from right atrium 212. In other embodiments, other paths may be taken.

Catheter 314 may include an elongated flexible rod or shaft member 316 appropriately sized to be deliverable percutaneously or intravascularly. According to various embodiments, the shaft member 316 may be employable or configured to percutaneously or intravascularly deliver the structure 308 through a bodily opening (e.g., the bodily opening in transatrial septum 210) leading to a bodily cavity (e.g., left atrium 204 of the heart 202) at least in response to translation of at least part of the shaft member 316. The shaft member 316 may include a shaft proximal end 316a (not shown in FIG. 2A, but shown, for example, in FIG. 3A. The shaft member 316 may also include a shaft distal end 316b (shown, for example, in FIG. 3A), with the structure 308 physically coupled to the shaft member 316 at least proximate the shaft distal end 316b. In addition, the shaft member 316 may include an elongated portion 316c (shown, for example, in FIG. 3A) extending between the shaft proximal end 316a and the shaft distal end 316b. According to some embodiments, the shaft member 316 includes a length extending from the proximal end 316a to the distal end 316b, the length of the shaft member 316 sufficient to position the proximal end 316a outside a body comprising the bodily cavity during a state in which the structure 308 is positioned in the bodily cavity.

In various embodiments, the shaft member 316 is physically coupled to the structure 308 at a location fixed with respect to the shaft distal end 316b. In various embodiments, the physically coupling between the shaft member 316 and the structure 308 allows for a movement (e.g., a translation) of the structure 308 in response to a movement (e.g., a translation) of at least part of the shaft member 316. In some embodiments, the structure 308 is physically coupled to shaft member 316 at a location that does not vary with respect to the shaft distal end 316b in response to a movement (e.g., a translation) of at least part of the shaft member 316. In some embodiments, the shaft member 316 is fixedly coupled to the structure 308. For example, as described in more detail below with respect to FIGS. 3G and 3H, the shaft member 316 may terminate with a collar 316b1 (not shown in FIGS. 3A, 3B, but shown in FIGS. 3G and 3H) at the shaft distal end 316b. In this regard, the collar 316b1 or other securing mechanism may physically or fixedly couple the shaft member 316 to the plurality of elongate members 304 forming the structure 308, according to some embodiments. Also in this regard, the shaft member 316 may be physically coupled to the plurality of elongate members 304, such that a respective location at which the shaft member 316 is physically coupled (e.g., at the collar 316b1) to each elongate member 304 is fixed with respect to the shaft distal end 316b of the shaft member 316, according to some embodiments.

Various portions of catheter 314 may be steerable. Catheter 314 may include one or more lumens. The lumen(s) may carry one or more communications or power paths, or both. For example, the lumens(s) may carry one or more electrical conductors or control leads 317. Electrical conductors 317 provide electrical connections for system 300 that are accessible externally from a patient in which the electrode-based device system 300 is inserted, according to some embodiments. In some embodiments, the electrical conductors 317 form part of various elongate members (e.g., elongate members 304 described below). In some embodiments, the electrical conductors 317 include, or form part of, various flexible circuit structures (e.g., as described in FIG. 4, below).

In some embodiments, the electrical conductors 317 may provide electrical connections to transducers 306 (three called out in FIG. 2A) that respectively may include one or more electrodes, and optionally one or more other devices, (e.g., both discussed with respect to FIG. 4, below) configured to, among other things, provide stimulation (e.g., electrical stimulation that may include pinging or pacing) to tissue within a bodily cavity (e.g., left atrium 204), ablate tissue in a desired pattern within the bodily cavity, sense characteristics of tissue (e.g., electrophysiological activity, convective cooling, permittivity, force, temperature, impedance, thickness, or a combination thereof) within the bodily cavity, or a combination thereof or sense various other animate or non-animate physical characteristics.

The sensing of characteristics may, among other things, be configured to distinguish between fluid, such as fluidic tissue (e.g., blood), and non-fluidic tissue forming an interior surface of a bodily cavity (e.g., left atrium 204); may be configured to map the cavity, for example, using positions of openings or ports into and out of the cavity; may be configured to determine a position or orientation (e.g., pose), or both of a portion of the device system 300 in the bodily cavity; may be configured to indicate whether an ablation has been successful; or a combination thereof.

Electrode-based device system 300 may include the frame or structure 308 on which the plurality of transducers 306 are located and which may assume an unexpanded or delivery configuration (e.g., FIGS. 3A, 3G, and 3H, discussed below) for delivery to left atrium 204. Structure 308 may be deployed or expanded (e.g., shown in a deployed or expanded configuration in FIG. 2A, as well as at least FIGS. 2B, 3B, and 3C, which are discussed below) upon delivery to left atrium 204. In this regard, in some embodiments, the electrode-based device system 300 or the structure 308 thereof is selectively moveable between a delivery or unexpanded configuration (e.g., FIGS. 3A, 3G, and 3H, discussed below) and a deployed or expanded configuration (e.g., FIG. 2A, as well as at least FIGS. 2B, 3B, and 3C discussed below). U.S. Pat. No. 9,452,016, issued Sep. 27, 2016, includes disclosures regarding various actuators, control lines, and other mechanisms by which a transducer or electrode-based device may be selectively moveable between a delivery or unexpanded configuration and a deployed or expanded configuration, and U.S. Pat. No. 9,452,016, issued Sep. 27, 2016 is hereby incorporated herein by reference in its entirety. In the delivery or unexpanded configuration, a portion (e.g., the structure 308) of the device system 300 is sized to be percutaneously or intravascularly deliverable to a bodily cavity, e.g., via passage thereof through a bodily opening leading to the bodily cavity, according to some embodiments. In some embodiments where a first particular portion of each elongate member 304 is included in the structure 308, the first portions of the elongate members 304 are sized to be percutaneously or intravascularly deliverable to the bodily cavity when the structure 308 is in the delivery or unexpanded configuration. In the deployed or expanded configuration, a portion (e.g., the structure 308 or first particular portions 309a of elongate members 304 discussed below) of the device system 300 is sized too large to be percutaneously or intravascularly deliverable to the bodily cavity and to allow passage thereof through the bodily opening leading to the bodily cavity. In some embodiments where a first particular portion 309a of each elongate member 304 is included in the structure 308, the first portions of the elongate members 304 are sized too large to be percutaneously or intravascularly deliverable to the bodily cavity and to allow passage thereof through the bodily opening leading to the bodily cavity.

An example of an expanded or deployed configuration is when the portion of the electrode-based device system (e.g., the structure 308) is in its intended-deployed-operational state inside the bodily cavity. Another example of the expanded or deployed configuration is when the portion of the electrode-based device system 300 is being changed from the delivery configuration to the intended-deployed-operational state to a point where the portion of the device system now has a size too large for passage through the bodily opening leading to the bodily cavity. In some embodiments, the portion of the electrode-based device system 300 has a size or dimension when the structure 308 is in the expanded or deployed configuration that is larger than the corresponding size or dimension of the portion of the electrode-based device system 300 in the delivery configuration. Further, in some embodiments, when the portion (e.g., the structure 308) is in the expanded or deployed configuration in the left atrium 204, various ones of a plurality of transducers 306 may be positionable proximate the interior surface formed by non-fluidic tissue 222 of left atrium 204. In some embodiments, when the portion (e.g., the structure 308) is in the expanded or deployed configuration in the left atrium 204, various ones of plurality of transducers 306 may be positionable such that a physical portion of each of the various ones of the transducers 306 is configured to contact the interior surface formed by non-fluidic tissue 222 of left atrium 204. In some embodiments, at least some of the transducers 306 are configured to sense a physical characteristic of a fluid (i.e., blood), non-fluidic tissue 222 (i.e., cardiac wall tissue), or both, that may be used to determine a position of a particular anatomical feature (e.g., a cardiac port provided by a pulmonary vein or a cardiac valve). In some embodiments, at least some of the transducers 306 are configured to sense a physical characteristic (e.g., an electric or magnetic field created by various locator or navigation systems) to determine a position or orientation (i.e., pose), or both, of a portion of a device system 300 within, or with respect to left atrium 204. For example, transducers 306 may be configured to determine a location of pulmonary vein ostia (not shown) or a mitral valve 226, or both. In some embodiments, at least some of the transducers 306 may be controlled to selectively ablate portions of the non-fluidic tissue 222. For example, some of the transducers 306 may be controlled to ablate a pattern or path around various ones of the bodily openings, ports or pulmonary vein ostia, for instance, to reduce or eliminate the occurrence of atrial fibrillation. Each of various ones of the transducers 306 may include an electrode in various embodiments, as described below with respect to FIG. 4, for example.

Figure 3A:
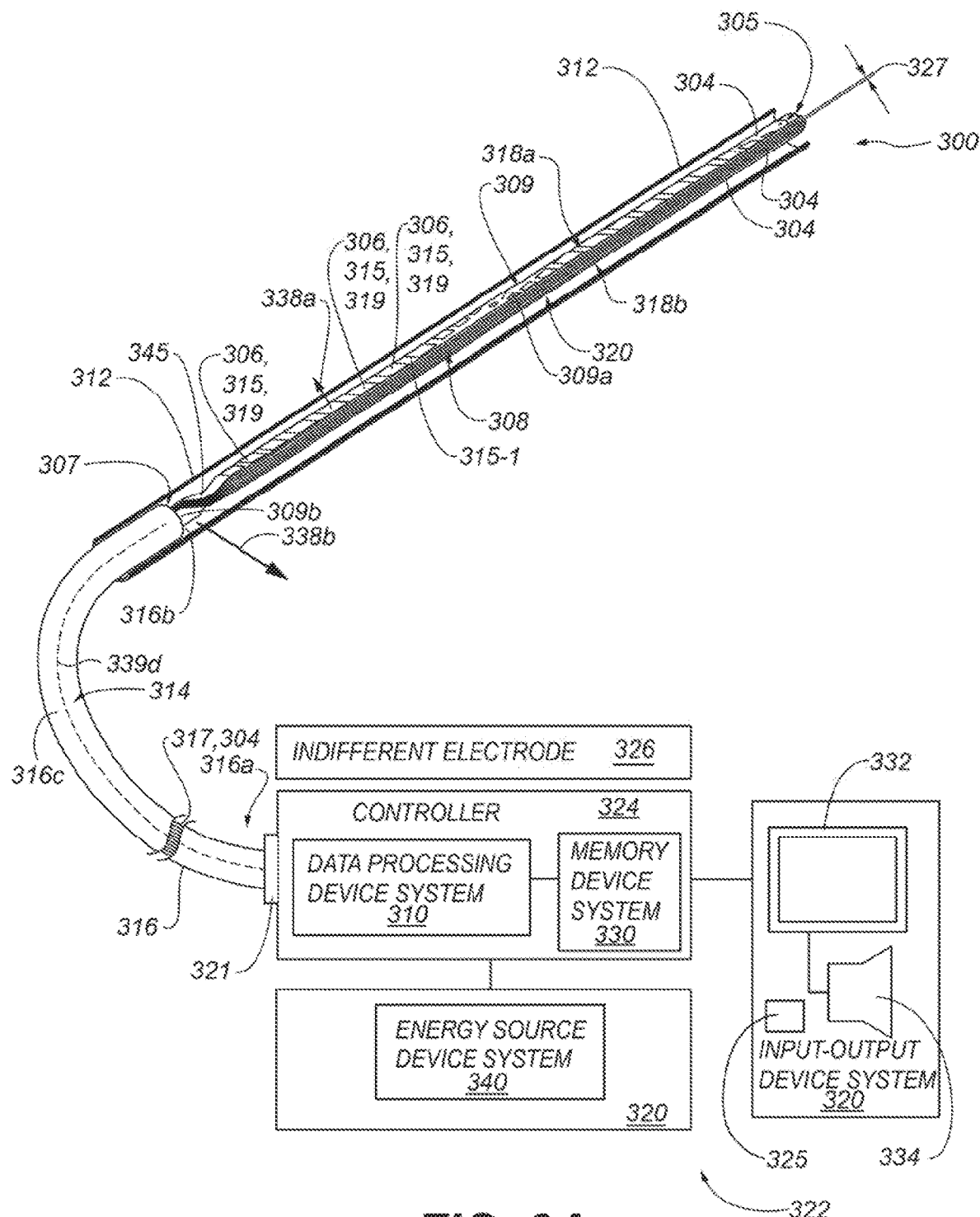
FIG. 3A is a partial schematic view of a medical device system, which may represent one or more implementations of the medical device system of FIG. 1 in which an expandable structure of an electrode-based device system is in a delivery or unexpanded configuration, according to various example embodiments.
Figure 3B:
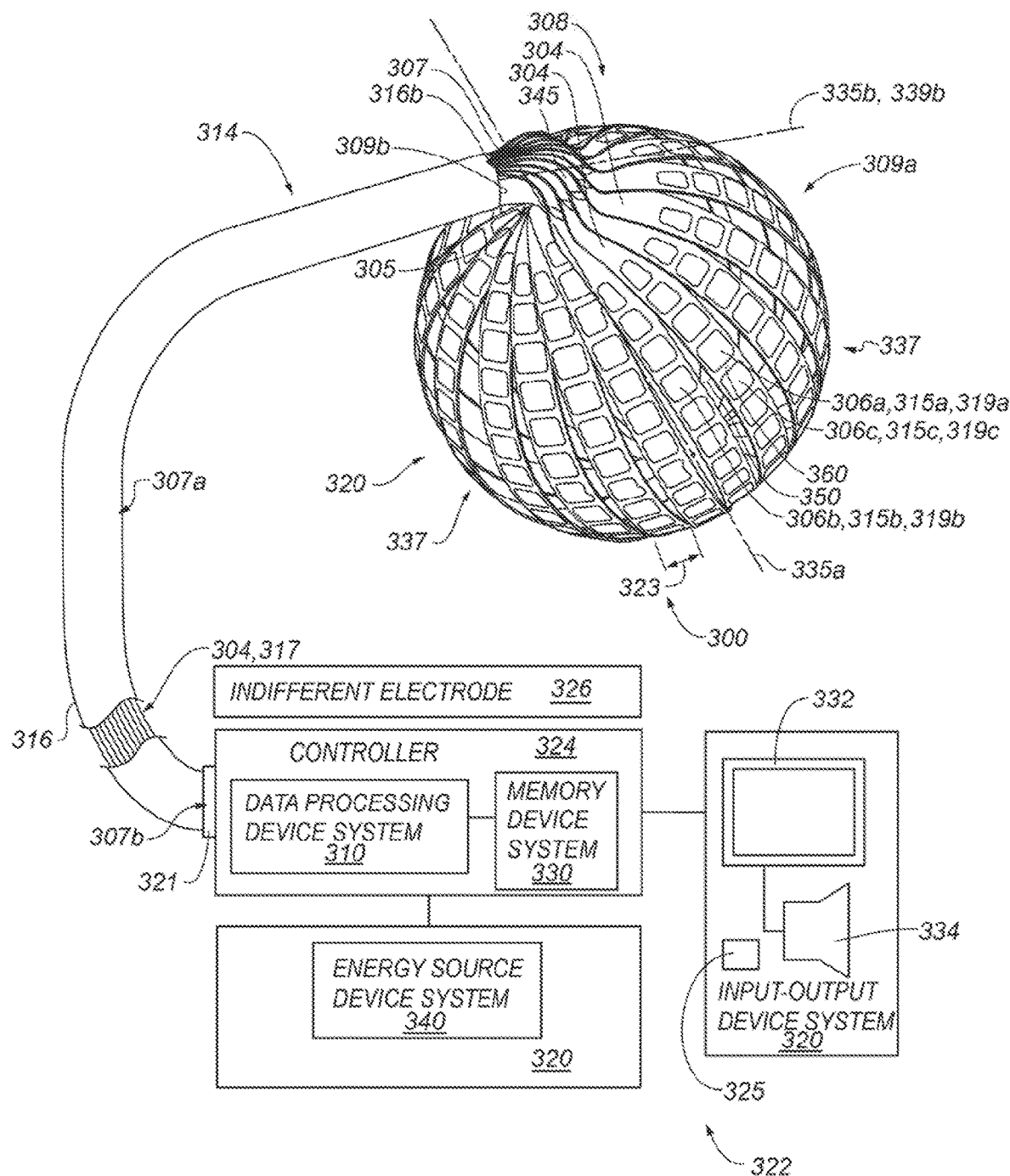
FIG. 3B is a partial schematic view of the medical device system of FIG. 3A with the expandable structure shown in a deployed or expanded configuration, according to some embodiments.

Each of FIGS. 3A and 3B is a partial schematic representation of a medical device system, which may represent one or more implementations of the medical device system 100 of FIG. 1, according to some embodiments. The medical system of each of these figures may include the electrode-based device system 300, which itself may include several hundred transducers 306 or electrodes 315 (only a few called out in the figures), but need not include that many. FIG. 3A illustrates the electrode-based device system 300 in a delivery or unexpanded configuration, according to various example embodiments, and FIGS. 3B and 3C illustrate the electrode-based device system 300 in a deployed or expanded configuration, according to some embodiments.

In this regard, the electrode-based device system 300 may include a plurality of elongate members 304 (only a few called out in the figures) and a plurality of transducers 306 or electrodes 315 (only a few called out in the figures). In some embodiments, the transducers 306 or electrodes 315 have the configuration of the transducers 306 or electrodes 315 in FIG. 2A. In some embodiments, the transducers 306 or electrodes 315 are formed as part of, coupled to, or are located on, at least some of the elongate members 304. In this regard, in some embodiments, each elongate member 304 has located thereon a respective set of one or more of the transducers 306. Accordingly, the transducers 306 located on a single elongate member 304 may be considered a set of transducers in some embodiments. In this regard, it may be considered that a plurality of sets of one or more transducers 306 exists, with, in some embodiments, each transducer set being located on a respective elongate member 304. As discussed in more detail below with respect to FIG. 4, the transducers 306 may include electrodes 315, such that each transducer 306 includes a respective electrode 315 according to some embodiments. In some embodiments, the transducers 306 or electrodes 315 are operable to be energized (e.g., via an energy source device system 340, discussed below) to interact with tissue within the bodily cavity.

Figure 3C:
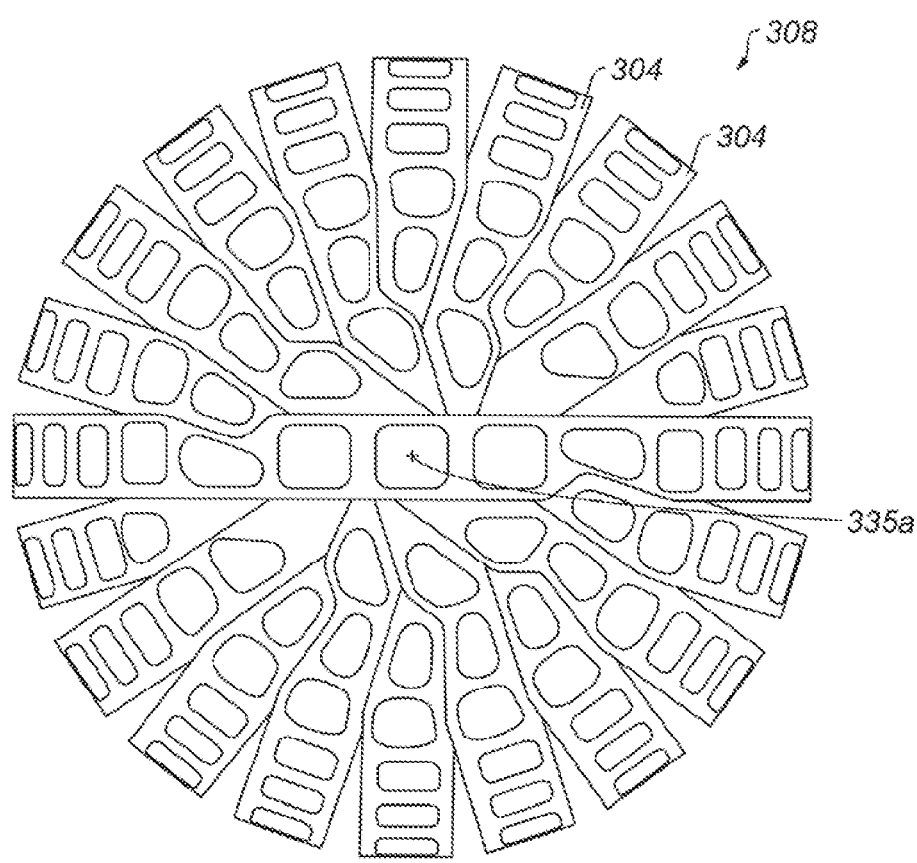
FIG. 3C illustrates a portion of the medical device system of FIG. 3A as viewed from a different viewing angle, according to some embodiments.

In some embodiments, the elongate members 304 are arranged as, or form at least part of, the frame or structure 308 that is selectively moveable between an unexpanded or delivery configuration (e.g., as shown in FIG. 3A) and an expanded or deployed configuration (e.g., as shown in FIGS. 3B and 3C) that may be used to position or distribute particular portions of elongate members 304 at various locations within a bodily cavity (e.g., locations away from a tissue surface within the bodily cavity, locations against a tissue surface, or locations at least proximate the tissue surface).

In some embodiments, the structure 308 has a size in the unexpanded or delivery configuration suitable to allow the structure 308 to be percutaneously or intravascularly deliverable at least partially through a bodily opening (e.g., via catheter sheath 312, shown in FIG. 3A, but not in the other figures for purposes of clarity) to the bodily cavity. In some embodiments, structure 308 has a size when the structure 308 is in the expanded or deployed configuration too large to allow the structure to be intravascularly or percutaneously deliverable through a bodily opening (e.g., via catheter sheath 312) to the bodily cavity.

The elongate members 304 may form part of or include a flexible circuit structure (i.e., also known as a flexible printed circuit board (PCB) circuit). The elongate members 304 may include a plurality of different material layers. Each of the elongate members 304 may include a plurality of different material layers. The structure 308 may include a shape memory material, for instance Nitinol. The structure 308 may include a metallic material, for instance stainless steel, or non-metallic material, for instance polyimide, or the structure 308 may include both a metallic and a non-metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern. For clarity, not all of the elongate members shown in the deployed or expanded configuration shown in FIG. 3B are shown in the structure 308 in the delivery configuration shown in FIG. 3A.

One or more transducers of the plurality of transducers 306 is or are positionable within a bodily cavity, for example, by positioning of the structure 308. For instance, in some embodiments, various ones of the transducers 306 are able to be positioned in a bodily cavity by movement into, within, or into and within the bodily cavity, with or without a change in a configuration of the plurality of transducers 306 (e.g., a change in a configuration of the structure 308 causes a change in configuration of the transducers 306 in some embodiments). In some embodiments, the plurality of transducers 306 is arrangeable to form a two- or three-dimensional distribution, grid or array capable of mapping, ablating or stimulating or otherwise interacting with an inside surface of a bodily cavity or lumen without requiring mechanical scanning.

As shown for example in FIG. 3A, the plurality of transducers 306 is arranged in a distribution receivable in a bodily cavity (not shown in FIG. 3A). As shown for example, in FIG. 3A, the plurality of transducers 306 is arranged in a distribution suitable for delivery to a bodily cavity, according to some embodiments. Also as shown for example in FIG. 3A, the structure 308, when in the delivery configuration, arranges at least part of each respective elongate member of the plurality of elongate members 304 to be advanced with a distal end (also referred to as the second end) 305 of the respective elongate member 304 ahead of a proximal portion 307 of the respective elongate member 304 toward the bodily cavity, according to some embodiments. In some embodiments, the proximal portion 307 or portions thereof (e.g., 307a, 307b, or both) is or are at least part of proximal portion 309c, proximal portion 309d, or both (discussed in more detail below with respect to e.g., at least FIG. 3D and afterwards). In some embodiments, proximal portion 307 is located within shaft member 316 (e.g., within a lumen in shaft member 316). In some embodiments, the proximal portion 307 may be considered an external proximal portion, because it exists just external of the shaft member 316 (for example as described below), according to some embodiments.

FIG. 3B shows another proximal portion 307a of each respective elongate member 304 located within the shaft member 316 just proximal a point or location where the helical configuration or twisted, non-helical configuration discussed below (e.g., with respect to FIGS. 3D, 3E, 3F, 3G, 3H, 3I, 3J, 3K, and 3L) begins turning within the shaft member 316. (All or one or more sections of the shaft member 316 have been removed in at least FIGS. 2A, 2B, 3A, 3B, 3D, 3E, 3F, 3G, 3H, 3I, and 3J to show what is occurring within the shaft member 316 at the removed portions.) Accordingly, the proximal portion 307a may be considered a pre-helix or pre-twist intermediate internal proximal portion of each respective elongate member 304. Also shown in FIG. 3B is yet another proximal portion 307b of each respective elongate member 304 located at a proximal end of each respective elongate member 304 where each respective elongate member 304 terminates, e.g., at the connector 321, at the controller 324, or at the data processing device system 310, according to various embodiments. Accordingly, the proximal portion 307b of each respective elongate member 304 may be considered a respective proximal end of the respective elongate member 304. (Although the arrows 307a, 307b point near an exterior of the shaft member in FIG. 3B, such arrows are intended to refer to an interior where the elongate members reside according to some embodiments.) In some embodiments, the proximal portion (e.g. 307a, 307b) of each respective elongate member 304 includes portions of various ones of conductors 317.

In some embodiments, as shown, for example, in FIG. 3A, each of the plurality of elongate members 304 is arranged to be percutaneously or intravascularly deliverable distal end first or distal end ahead of various ones of the proximal portions 307 to the bodily cavity when the structure is in the delivery configuration. In some embodiments, at least some of the elongate members 304 are arranged to be percutaneously or intravascularly deliverable with a portion thereof other than the distal end delivered first to the bodily cavity when the structure is in the delivery configuration.

Figure 4:
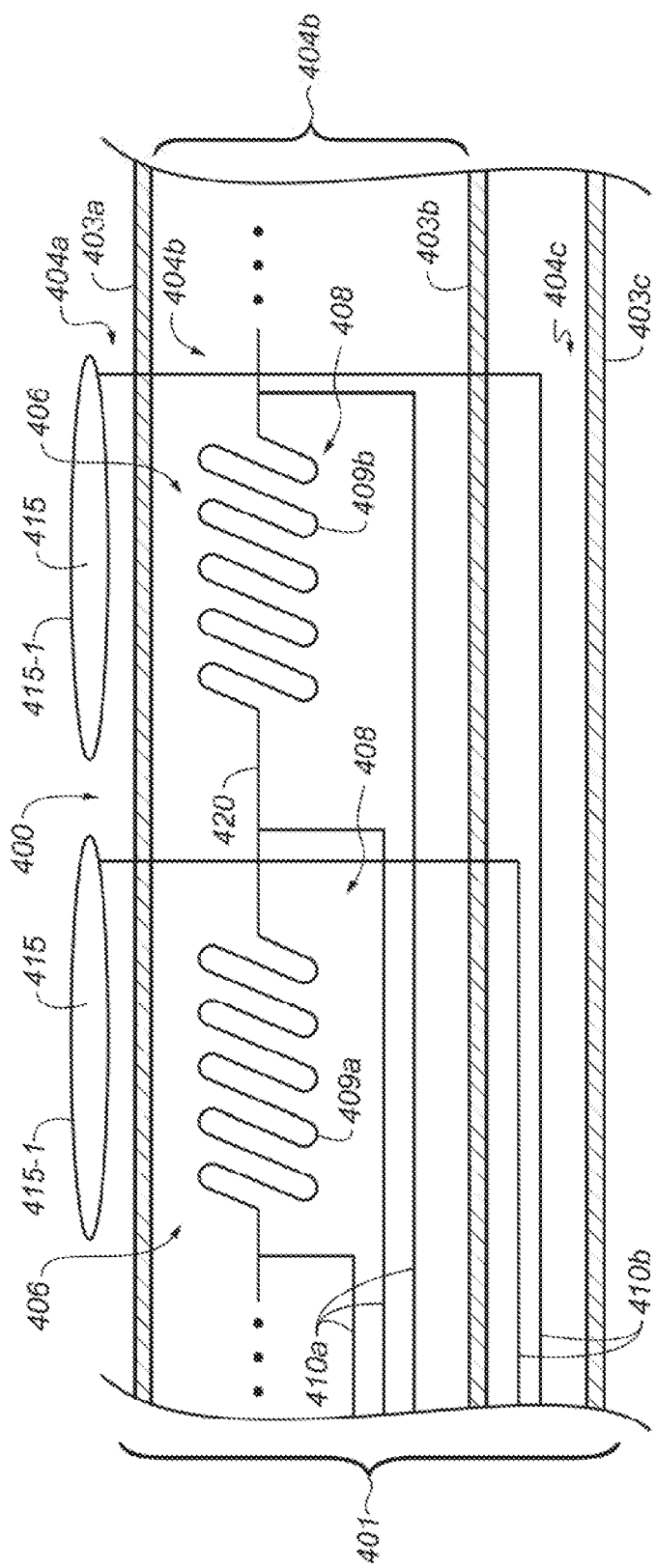
FIG. 4 is a schematic representation of an electrode-based device that includes a flexible circuit structure, according to various example embodiments.

FIG. 4 is a schematic side elevation view of at least a portion of an electrode-based device system 400 that includes a flexible circuit structure 401 that is employed to provide a plurality of transducers 406 (two called out) according to various example embodiments. The portion of the electrode-based device system 400 may form part of each of one or more or all elongate members 304, according to some embodiments. In some embodiments, the transducers 406 correspond to the transducers 306. In some embodiments, at least a particular portion of the flexible circuit structure 401 may form part of a structure (e.g., structure 308) that is selectively moveable between a delivery configuration sized for percutaneous or intravascular delivery and an expanded or deployed configuration sized too large for percutaneous or intravascular delivery. In some embodiments, at least a particular portion of the flexible circuit structure 401 may be located on, or form at least part of, a structural component (e.g., elongate member 304) of an electrode-based device system (e.g., electrode-based device system 300). In some embodiments, at least part of the flexible circuit structure 401 may provide each particular portion of an elongate member. For each respective elongate member 304, the flexible circuit structure 401 may include or may form at least part of a respective portion (e.g., the respective portion 309a (discussed in more detail below), the respective portion 309b (discussed in more detail below), the respective portion 309c (discussed in more detail below), or a combination of two or all of such portions or other portions described herein) of the respective elongate member 304. For example, in some embodiments, the flexible circuit structure 401 may begin at a connection with data processing device system 310 and extend at least to and include the transducers 306 of the respective elongate member 304. For another example, in some embodiments, conductors may be connected at one end to the data processing device system 310 and extend through some proximal portion of the shaft member 316 and be connected at the other end to the flexible circuit structure 401 at some intermediate internal proximal portion (e.g., 307a or other portion within the shaft member 316) where the flexible circuit structure 401 and its respective elongate member 304 begin. In some embodiments, for each respective elongate member 304, a multi-layer structure (e.g., flexible circuit structure 401) may include or may form at least part of a respective portion (e.g., the respective portion 309a (discussed in more detail below), the respective portion 309b (discussed in more detail below), the respective portion 309c (discussed in more detail below), or a combination of two or all of such portions or other portions described herein) of the respective elongate member 304. According to some embodiments, for each respective elongate member 304, the flexible circuit structure 401 may extend or exist from a proximal end of the respective elongate member 304 to a distal end of the respective elongate member 304. According to some embodiments, for each respective elongate member 304, the flexible circuit structure 401 may proximally begin at a proximal end of the respective elongate member 304 and end at a distal end of the respective elongate member 304. In some embodiments, for each particular elongate member 304, the particular elongate member 304 includes the flexible circuit structure 401 extending between the proximal end of the particular elongate member 304 and the distal end of the particular elongate member 304. In some embodiments, for each particular elongate member 304, the particular elongate member 304 includes the flexible circuit structure 401 extending between the proximal portion 307, the proximal portion 307a, or the proximal portion 307b, and the distal end 305 of the particular elongate member 304.

In some embodiments, for each particular elongate member 304, the particular elongate member 304 includes a flexible circuit structure 401 that includes a plurality of separately formed portions, each of the portions physically and electrically coupled together to form flexible circuit structure 401 extending between the proximal end of the particular elongate member 304 and the distal end of the particular elongate member 304. The use of physically and electrically coupled, but separately formed portions may be motivated for different reasons including limitations in flexible printed circuit manufacturing techniques in forming a single flexible circuit structure 401 having sufficient length to extend between the proximal end of the particular elongate member 304 and the distal end of the particular elongate member 304.

In some embodiments, at least a particular portion of the flexible circuit structure 401 may form, provide, or be connected to at least part of one or more conductors (e.g., conductors 317, one or more of which may be connected to leads 410a, 410b in FIG. 4, discussed in more detail below) arranged to provide a power or communications path to various ones of the transducers 406). It is noted that conductors provided by the flexible circuit structure 401 need not be confined to portions of flexible circuit structure 401 forming part of, or positioned at least proximate the structure (e.g., structure 308), but rather may be configured to extend over a substantial portion of a path extending from various ones of the transducers 306 located within a bodily cavity to a location outside a body that comprises the bodily cavity. Such configuration may provide enhanced reliability from a reduced number of required connectors as well as reducing various economic costs associated with the system.

The flexible circuit structure 401 may be formed by various techniques including flexible printed circuit techniques. In some embodiments, the flexible circuit structure 401 includes various layers including flexible layers 403 (three called out in FIG. 4 as reference symbols 403a, 403b, and 403c). In some embodiments, each of the flexible layers 403 includes an electrical insulator material (e.g., polyimide). One or more of the flexible layers 403 may include a different material than another of the flexible layers 403. In some embodiments, the flexible circuit structure 401 includes various electrically conductive layers 404 (three called out in FIG. 4 as reference symbols 404a, 404b, and 404c). The electrically conductive layers 404 may be interleaved with the flexible layers 403. In some embodiments, each of the electrically conductive layers 404 is patterned to form various electrically conductive elements. For example, electrically conductive layer 404a may be patterned to form a respective electrode 415 included as part of each of the transducers 406. Electrodes 415 may have respective electrode edges 415-1 that form a periphery of an electrically conductive surface or surface portion associated with the respective electrode 415.

In some embodiments, the respective electrically conductive surface or surface portion of one or more of the electrodes 415 (or 315) is configured to transmit energy to adjacent or contacting tissue at a level sufficient for ablation of the tissue. Other energy levels may be transmitted to, for example, provide stimulation (e.g., electrical stimulation that may include pinging or pacing) to tissue within a bodily cavity (e.g., left atrium 204), sense characteristics of tissue (e.g., electrophysiological activity, convective cooling, permittivity, force, temperature, impedance, thickness, or a combination thereof) within the bodily cavity, or a combination thereof.

Electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive element 409 (two called out as 409a and 409b) having a predetermined electrical resistance. In some embodiments, each resistive element 409 includes a metal having relatively high electrical conductivity characteristics (e.g., copper). In some embodiments, the resistive element 409 has a serpentine form. The serpentine form has the advantage of providing an increase in the overall resistance of resistive element 409 by increasing its overall length while maintaining a compact spatial arrangement. In some embodiments, each resistive element 409 is connected to an adjacent resistive element 409 by a conductive element 420 (only one instance of conductive element 420 is shown in FIG. 4 for clarity).

In some embodiments, electrically conductive layer 404c is patterned to provide portions of various leads 410b arranged to provide an electrical communication path to electrodes 415. In some embodiments, leads 410b are arranged to pass though vias (accounted for in FIG. 4, e.g., by the upward (with respect to the proper orientation of FIG. 4) movement of the leads 410b) in flexible layers 403a and 403b to connect with electrodes 415. In various embodiments, electrically conductive layer 404b, electrically conductive layer 404c, or both electrically conductive layer 404b and electrically conductive layer 404c have sufficient length to allow various ones of leads 410a and 410b (or other leads) to extend at least outside the body when the transducers 406 are positioned at desired locations within a bodily cavity comprised by the body. In various embodiments, electrically conductive layer 404b, electrically conductive layer 404c, or both electrically conductive layer 404b and electrically conductive layer 404c have sufficient length to allow at least various ones of leads 410a and 410b (or other leads) to extend across all the particular portions of an elongate member.

Although FIG. 4 shows flexible layer 403c as being a bottom-most layer, some embodiments may include one or more additional layers underneath flexible layer 403c, such as one or more structural layers, such as a stainless steel or composite layer. These one or more structural layers, in some embodiments, are part of the flexible circuit structure 401 and may be part of, e.g., elongate member 304. In addition, although FIG. 4 shows only three flexible layers 403a-403c and only three electrically conductive layers 404a-404c, it should be noted that other numbers of flexible layers, other numbers of electrically conductive layers, or both, may be included. It should be noted that the various structures of the flexible circuit system, such as the electrode 415 and resistive element 409, for example, may include different metals or conductive materials according to some embodiments.

It is noted that various elements such as electrodes 415 and resistive elements 409 are schematically represented in various orientations that are convenient for the sake of clarity in FIG. 4, and that at least some of these orientations may be different from one another. It is also noted that various elements are not shown to scale. For example, according to some embodiments, while layers 403a, 403b and 403c may be considered to be depicted by side elevation views of the layers on FIG. 4, electrodes 415 and resistive elements 409 may be considered to be depicted by perspective or plan views of the particular layers they are formed from. It is understood that these different orientations are provided to facilitate the discussion of these various elements and do not impose a limitation on the spatial or structural arrangements.

In some embodiments, the flexible circuit structure 401 may include at least one electrically nonconductive flexible layer 403 (electrically nonconductive substrate), at least one electrically conductive flexible circuit layer 404 coupled, directly or indirectly, to the at least one electrically nonconductive flexible layer 403. In some embodiments, the electrically conductive flexible circuit layer 404 may include conductive patterns including the plurality of resistive elements 409.

In some embodiments, the flexible circuit structure 401 is electrically connected to a voltage or current measurement system (e.g., provided at least in part by (a) input-output device system 120, 320, (b) data processing device system 110, 310, or both (a) and (b), by the plurality of measurement leads 410a. In some embodiments, respective pairs of measurement leads 410a are arranged to sense voltage or current across each resistive element 409. In some embodiments, at least some of the measurement leads 410a are electrically connected to a respective conductive element 420. In some embodiments, voltage measurement leads 410a are arranged to allow for a sampling of electrical voltage between each resistive element 409. These arrangements allow for the electrical resistance of each resistive element 409 to be accurately determined. The ability to accurately determine the electrical resistance of each resistive element 409 may be motivated by various reasons including determining temperature values at locations at least proximate the resistive element 409 based at least on changes in the resistance caused by convective cooling effects (e.g., as provided by blood flow).

In some embodiments, electrodes 415 are employed to selectively deliver RF energy to various tissue structures within a bodily cavity (not shown) (e.g., a tissue cavity such as an intra-cardiac cavity). The energy delivered to the tissue structures may be sufficient for ablating portions of the tissue structures. In various embodiments, the tissue structures are typically formed from non-fluidic tissue and the energy sufficient for ablating portions of the tissue structures is typically referred to as sufficient for tissue ablation. It is noted that energy sufficient for non-fluidic-tissue ablation may include energy levels sufficient to disrupt or alter fluidic tissue (e.g., blood) that may, for example, be located proximate the tissue structure. In many cases, the application of non-fluidic-tissue-ablative energy (i.e., energy that is sufficient to ablate non-fluidic tissue) to fluidic tissue, such as blood, is undesired when the energy is sufficient to disrupt or adversely impact a property of the fluidic tissue. For example, the application of non-fluidic-tissue-ablative energy to blood may be undesired when the energy is sufficient to cause various parts of the blood to coagulate in a process typically referred to as thermal coagulation. In this regard, some embodiments facilitate detection of conditions where an electrode configured to deliver non-fluidic-tissue-ablative energy may be in a configuration where it is not able to properly transmit such energy. In some embodiments, a detection of such a condition results in an error notification being transmitted or otherwise presented to a user or, in some embodiments, a restriction of that electrode from transmitting at least a portion of the non-fluidic-tissue-ablative energy. In some embodiments, a detection of such a condition results in an error notification being transmitted or otherwise presented to a user or, in some embodiments, a restriction of that electrode from being selected by a user action (e.g., a user selection of that electrode from a number of selectable electrodes to perform a particular function, such as transmitting at least a portion of the non-fluidic-tissue-ablative energy).

The energy delivered to the tissue may be delivered to cause monopolar tissue ablation, bipolar tissue ablation, or blended monopolar-bipolar tissue ablation by way of non-limiting example. In some embodiments, each electrode 415 is employed to sense an electrical potential in the tissue proximate the electrode 415. In some embodiments, each electrode 415 is employed in the generation of an intra-cardiac electrogram. In some embodiments, each resistive element 409 is positioned adjacent a respective one of the electrodes 415. In some embodiments, each of the resistive elements 409 is positioned in a stacked or layered array with a respective one of the electrodes 415 to form a respective one of the transducers 406. In some embodiments, the resistive elements 409 are connected in series to allow electrical current to pass through all of the resistive elements 409. In some embodiments, leads 410*a* are arranged to allow for a sampling of electrical voltage across each resistive element 409. This arrangement allows for the electrical resistance of each resistive element 409 to be accurately determined. The ability to accurately determine the electrical resistance of each resistive element 409 may be motivated by various reasons including determining temperature values at locations at least proximate the resistive element 409 based at least on changes in the resistance caused by convective cooling effects (e.g., as provided by blood flow). In various embodiments, some of the transducers 406 are controlled to provide one or more electrical signals to tissue (e.g., non-fluidic tissue associated with a tissue wall or fluidic tissue such as blood) and information or a derivative thereof is determined in response to the provided signals, the information or the derivative thereof indicating a result of an interaction between the one or more signals and the tissue. In various ones of these embodiments, the one or more signals may include one or more energy levels insufficient for tissue ablation.

In some embodiments in which the electrode-based device system 300 is deployed in a bodily cavity (e.g., when the electrode-based device system 300 takes the form of a catheter device system arranged to be percutaneously or intravascularly delivered to a bodily cavity), it may be desirable to perform various mapping procedures in the bodily cavity. For example, when the bodily cavity is an intra-cardiac cavity, a desired mapping procedure may include mapping electrophysiological activity in the intra-cardiac cavity. Other desired mapping procedures may include mapping of various anatomical features within a bodily cavity. An example of the mapping performed by devices according to various embodiments may include locating the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as a left atrium.

In some example embodiments, the mapping is based at least on locating bodily openings by differentiating between fluid and non-fluidic tissue (e.g., tissue defining a surface of a bodily cavity). There are many ways to differentiate non-fluidic tissue from a fluid such as blood or to differentiate tissue from a bodily opening in case a fluid is not present. Four approaches may include by way of non-limiting example, and, depending upon the particular approach(es) chosen, the configuration of transducers 406 in FIG. 4 may be implemented accordingly:

1. The use of convective cooling of heated transducer elements by fluid. An arrangement of slightly heated transducer elements that is positioned adjacent the tissue that forms the interior surface(s) of a bodily cavity and across the ports of the bodily cavity will be cooler at the areas which are spanning the ports carrying the flow of fluid.
2. The use of tissue impedance measurements. A set of transducers positioned adjacently to tissue that forms the interior surface(s) of a bodily cavity and across the ports of the bodily cavity may be responsive to electrical tissue impedance. Typically, heart tissue will have higher associated tissue impedance values than the impedance values associated with blood.
3. The use of a differing change in dielectric constant as a function of frequency between blood and tissue. A set of transducers positioned around the tissue that forms the interior surface(s) of the atrium and across the ports of the atrium monitors the ratio of the dielectric constant from 1 kHz to 100 kHz. Such may be used to determine which of those transducers is not proximate tissue, which is indicative of the locations of the ports.
4. The use of transducers that sense force (i.e., force sensors). A set of force detection transducers positioned around the tissue that forms the interior surface(s) of a bodily cavity and across the bodily openings or ports of the bodily cavity may be used to determine which of the transducers are not engaged with the tissue, which may be indicative of the locations of the ports.

Various ones of the above approaches may be used, at least in part, to determine proximity of a transducer to non-fluidic tissue or to fluidic tissue in some embodiments. Various ones of the above approaches may be used, at least in part, to determine contact between a transducer and non-fluidic tissue or contact between a transducer and fluidic tissue in some embodiments. Various ones of the above approaches may be used, at least in part, to determine an amount of an electrically conductive surface portion of an electrode that contacts non-fluidic tissue or contacts fluidic tissue in some embodiments. Various ones of the above approaches may be used, at least in part, to determine an amount of an electrically conductive surface portion of an electrode that is available to contact non-fluidic tissue or available to contact fluidic tissue in some embodiments.

Referring again to the medical device systems of FIGS. 3A and 3B, according to some embodiments, electrode-based device system 300 communicates with, receives power from or is controlled by a transducer-activation system 322, which may include a controller 324 and an energy source device system 340. In some embodiments, the controller 324 includes a data processing device system 310 and a memory device system 330 that stores data and instructions that are executable by the data processing device system 310 to process information received from other components of the medical device system of FIGS. 3A and 3B or to control operation of components of the medical device system of FIGS. 3A and 3B, for example by activating various selected transducers 306 to ablate tissue, sense tissue characteristics, et cetera. In this regard, the data processing device system 310 may correspond to at least part of the data processing device system 110 in FIG. 1, according to some embodiments, and the memory device system 330 may correspond to at least part of the memory device system 130 in FIG. 1, according to some embodiments. The energy source device system 340, in some embodiments, is part of an input-output device system 320, which may correspond to at least part of the input-output device system 120 in FIG. 1. Although only a single controller 324 is illustrated, it should be noted that such controller 324 may be implemented by a plurality of controllers. In some embodiments, the electrode-based device system 300 is considered to be part of the input-output device system 320. The input-output device system 320 may also include a display device system 332, a speaker device system 334, or any other device such as those described above with respect to the input-output device system 120.

In some embodiments, particular portions (e.g., 309, where 309a, 309b are shown in FIGS. 3A and 3B, and 309c is shown in at least FIGS. 3G and 3H) of the elongate members 304 may include or form at least a portion or an extension of control leads 317 that reside, at least in part (e.g., portion 309c), in the shaft member 316 and, at least in part, in the flexible catheter 314. For example, the leads 410a, 410b in FIG. 4 may be or form a portion or an extension of control leads 317 in some embodiments. The control leads may be connected to the controller 324 at a connector 321 or other interface with the transducer-activation system 322 and provide communication pathways between at least the transducers 306 and the controller 324, according to some embodiments. In some embodiments in which particular portions of the elongate members 304 may include, or form a portion or an extension of, control leads 317, various particular portions of the elongate members 304 may be provided by flexible circuit structures (e.g., 401). In some embodiments, the elongate members 304 may terminate at connector 321 or other interface with the transducer-activation system 322, e.g., at the controller 324 or data processing device system 310, and provide communication pathways between at least the transducers 306 and the controller 324. In some embodiments, in which particular portions of the elongate members 304 may include or form a portion or an extension of control leads 317, the elongate members may terminate at or in a housing physically coupled to shaft member 316, such as a housing of controller 324 or other housing (e.g. a housing provided as part of handle portion as described in U.S. Pat. No. 9,452,016, issued Sep. 27, 2016, which is hereby incorporated herein by reference in its entirety.

As discussed with respect to FIG. 4, each of various ones of the transducers 306, 406 includes an electrode 315, 415, according to some embodiments. In these various embodiments, each of at least some of the electrodes 315, 415 may include a respective energy transmission surface (e.g., energy transmission surface 319 in FIG. 3A) configured to transfer, transmit, or deliver energy, for example, to tissue. In some embodiments, at least some of the respective energy transmission surfaces 319 are configured to receive energy, for example, from tissue. Each of the energy transmission surfaces may be bound by a respective electrode edge 315-1 (e.g., FIG. 3A), 415-1 (e.g., FIG. 4).

In various embodiments, each of the electrodes 315 includes an electrically conductive surface portion (e.g., energy transmission surface 319) that, in some embodiments, has an electrical conductivity that is typically greater than that of fluidic and non-fluidic tissue. In some embodiments, the entirety of the electrically conductive surface portion is configured to contact or is configured to be available or exposed for contact with a contiguous portion of a non-fluidic tissue surface (e.g., a tissue surface that defines a tissue wall). Complete contact between the entirety of the electrically conductive surface portion and the non-fluidic tissue may be motivated for different reasons. For example, various desired characteristics required in a lesion formed in a tissue wall in a tissue ablation procedure may be dependent on the degree of intimate contact established between the electrically conductive surface portion of the electrode 315 and the tissue wall. For example, intimate contact may be required to form a lesion having sufficient transmurality to act as an effective electrophysiological activity block (e.g., a block capable of forming a barrier to spurious electrical signals causing fibrillation in an atrium). In some cases, complete contact between the entirety of the electrically conductive surface portion and the non-fluidic tissue may be desired to reduce the time required to form a lesion to a desired tissue depth under the influence of a given ablation energy level. In some cases, complete contact between the entirety of the electrically conductive surface portion of the electrode 315 and the non-fluidic tissue may be desired to reduce transmission of ablative energy to a surrounding fluidic tissue. In some cases, complete contact between the entirety of the electrically conductive surface portion of the electrode 315 and the non-fluidic tissue may be desired to reduce or eliminate exposure of the electrically conductive surface portion of the electrode 315 to surrounding fluidic tissue when the electrically conductive surface portion of the electrode 315 is positioned in contact with non-fluidic tissue. In some embodiments, the entirety of the portion of the electrically conductive surface of the electrode 315 that is configured to contact or is configured to be available or exposed (e.g., without some obstruction preventing at least some of the ability) to contact a tissue wall surface includes all of the electrically conductive surface. For example, this may occur when the electrically conductive surface has a generally planar form (e.g., a generally planar conductive surface provided by an electrode formed by flexible circuit fabrication techniques (e.g., electrode 415)). In some embodiments, the entirety of the portion of the electrically conductive surface of the electrode that is configured to contact or is configured to be available or exposed to contact a tissue wall surface includes some, but not all, of the electrically conductive surface. For example, this may occur when the electrode has a generally three-dimensional surface (e.g., a surface having a cylindrical, hemi-spherical or other three-dimensional form) with only a portion less than the entirety of the three-dimensional surface configured to contact or configured to be available or exposed for contact with a tissue surface wall.

In some embodiments, input-output device system 320 may include a sensing device system 325 configured to detect various characteristics or conditions including, but not limited to, at least one of tissue characteristics (e.g., electrical characteristics such as tissue impedance, tissue type, tissue thickness) and thermal characteristics such as temperature. Various other particular conditions may be detected by sensing device system 325 according to various embodiments. It is noted that in some embodiments, sensing device system 325 includes various sensing devices or transducers configured to sense or detect a particular condition while positioned within a bodily cavity. In some embodiments, at least part of the sensing device system 325 may be provided by electrode-based device system 300 (e.g., various ones of transducers 306). In some embodiments, sensing device system 325 includes various sensing devices or transducers configured to sense or detect a particular condition while positioned outside a given bodily cavity or even outside a body that includes the bodily cavity. In some embodiments, the sensing device system 325 may include an ultrasound device system or a fluoroscopy device system or portions thereof by way of non-limiting example.

The energy source device system 340 may, for example, be connected to various selected transducers 306 or their respective electrodes 315 to provide energy in the form of electrical current or energy (e.g., RF energy) to the various selected transducers 306 or their respective electrodes 315 to cause ablation of tissue. In this regard, although FIGS. 3A and 3B show a communicative connection between the energy source device system 340 and the controller 324 (and its data processing device system 310), the energy source device system 340 may also be connected to the transducers 306 or their respective electrodes 315 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 or their respective electrodes 315 (e.g., via one or more communication lines through catheter 314, shaft member 316 or catheter sheath 312) that does not pass through the controller 324. In this regard, the energy source device system 340 may provide results of its delivering energy to, receiving energy from, or both delivering energy to and receiving energy from one or more of the transducers 306 or the respective electrodes 315 to the controller 324 (and its data processing device system 310) via the communicative connection between the energy source device system 340 and the controller 324.

The energy source device system 340 may, for example, provide energy in the form of electrical current to various selected transducers 306 or their respective electrodes 315. Determination of a temperature characteristic, an electrical characteristic, or both, at a respective location at least proximate each of the various transducers 306 or their respective electrodes 315 may be made under the influence of energy or current provided by the energy source device system 340 in various embodiments. Energy provided to an electrode 315 by the energy source device system 340 may in turn be transmittable by the electrodes 315 to adjacent tissue (e.g., tissue forming a tissue wall surface). In various embodiments, the transmittable energy is sufficient for tissue ablation. In some embodiments, the energy is insufficient for tissue ablation. The energy source device system 340 may include various electrical current sources or electrical power sources. In some embodiments, an indifferent electrode 326 is provided to receive at least a portion of the energy transmitted by at least some of the transducers 306 or their respective electrodes 315. Consequently, although not shown in FIGS. 3A and 3B, the indifferent electrode may be communicatively connected to the energy source device system 340 via one or more communication lines in some embodiments. The indifferent electrode 326 is typically configured to be positioned outside of a bodily cavity and may be positioned on an exterior body surface and, in some embodiments, although shown separately in FIGS. 3A and 3B, is considered part of and communicatively connected to the energy source device system 340.

Structure 308 may be delivered and retrieved at least in part via a catheter member, for example, a catheter sheath 312 (shown in FIG. 3A). It is noted according to some embodiments that structure 308 is typically deliverable or retrievable (e.g., in an unexpanded or delivery configuration) through a lumen of catheter sheath 312 by way of translation of at least part of the shaft member 316 through the lumen of the catheter sheath 312. In this regard, it may be understood that the structure 308 and the associated elongate members 304 are not coupled to catheter sheath 312 at a location that is fixed with respect to a reference location on the catheter sheath 312 (e.g., a distal end of the catheter sheath) since the structure 308 and associated elongate members 304 are free to translate through the catheter sheath 312.

In some embodiments, the structure 308 provides expansion and contraction capabilities for a portion of a medical device (e.g., an arrangement, distribution or array of transducers 306). The transducers 306 may form part of, be positioned or located on, mounted or otherwise carried on the structure 308 and the structure 308 may be configurable to be appropriately sized to slide within catheter sheath 312 in order to be deployed percutaneously or intravascularly. FIG. 3A shows one embodiment of such a structure 308, where particular portions of the elongate members 304 (e.g., first portions or (e.g., also referred to as) first particular portions 309a that may be included in and collectively form structure 308), in some embodiments, are stacked in a stacked arrangement (which may provide an example of what is sometimes referred to herein as a second stacked arrangement) in the delivery or unexpanded configuration to facilitate fitting within the flexible catheter sheath 312 or to facilitate percutaneous or intravascular delivery of structure 308 to a bodily cavity. FIG. 3B shows an embodiment of structure 308 in an expanded or deployed configuration in which structure 308 has or an arrangement of first particular portions 309a of elongate members 304 have enlarged or expanded to a size unsuitable to facilitate fitting with the catheter sheath 312 or unsuitable to facilitate percutaneous or intravascular delivery of structure 308 to a bodily cavity.

In some embodiments, each of the elongate members 304 includes a respective distal or second end 305 (only one called out in each of FIGS. 3A and 3B), a respective proximal or first end (e.g., 307, only one called out in each of FIGS. 3A and 3B), and a plurality of particular portions 309 positioned or arranged between the proximal end (e.g., 307) and the distal end 305. Various particular portions 309 are described in greater detail below. In some embodiments, each particular elongate member 304 includes a length extending along the elongate member 304 from the respective distal or second end 305 to the respective proximal or first end (e.g., 307) of the particular elongate member 304. In some embodiments, at least one particular portion 309 of each respective elongate member 304 may be located at a location where the structure 308 is coupled to the distal portion (e.g., a portion at least adjacent distal end 316b) of the shaft member 316. In some embodiments, at least a first particular portion 309 (e.g., first particular portion 309a bearing transducers 306) of each elongate member 304 extends outwardly from the shaft distal end 316b of the shaft member 316. In some embodiments, at least a first particular portion 309 (e.g., first particular portion 309a including transducers 306) of each elongate member 304 extends outwardly from the shaft distal end 316b of the shaft member 316, while concurrently, other particular portions 309 (e.g., second portions or second particular portions 309c) of the elongate member reside or are located within the elongated portion 316c of the shaft member 316 (e.g., as described in more detail below). In some embodiments, at least a second particular portion (e.g., second particular portion 309c) of each elongate member resides or is located within the elongated portion 316c of the shaft member 316 (e.g., as described in more detail below).

The plurality of portions 309 of each particular elongate member 304 provide at least the respective portions 309a (e.g., FIGS. 3A, 3B, 3G, 3H, 3K, 3L), 309b (e.g., FIGS. 3A, 3B, 3G, 3H, 3K, 3L), 309c (e.g., FIGS. 3G, 3H, 3K, 3L), and other portions described herein, according to some embodiments. In some embodiments, the plurality of portions 309 of each particular elongate member 304 collectively provide a first or front surface or side 318a of the particular elongate member 304, the first or front surface or side 318a positionable to face away from an interior of the bodily cavity toward an interior tissue surface within the bodily cavity (e.g., FIGS. 2A, 2B). In some embodiments, the plurality of portions 309 of each particular elongate member 304 collectively provide a second or back surface or side 318b opposite across a thickness 327 of the particular elongate member 304 from the front surface or side 318a of the particular elongate member 304. In some embodiments, at least a portion of the front surface or side 318a of each particular elongate member 304 faces outwardly from an interior of the structure 308 when the structure 308 is in the deployed or expanded configuration (e.g., as shown in FIGS. 2A, 2B, 3B, 3C). A width 323 (e.g., FIG. 3B) of each respective elongate member 304 is perpendicular to and longer than the thickness 327 and perpendicular to the length of the respective elongate member 304, according to some embodiments. In the expanded or deployed configuration, it may be considered, according to some embodiments, that the width 323 of a respective elongate member 304 at a particular location along the elongate member 304 is perpendicular to a tangent of the length of the respective elongate member 304 at the particular location, since the respective elongate member 304 may exhibit curvature.

Figure 2B:
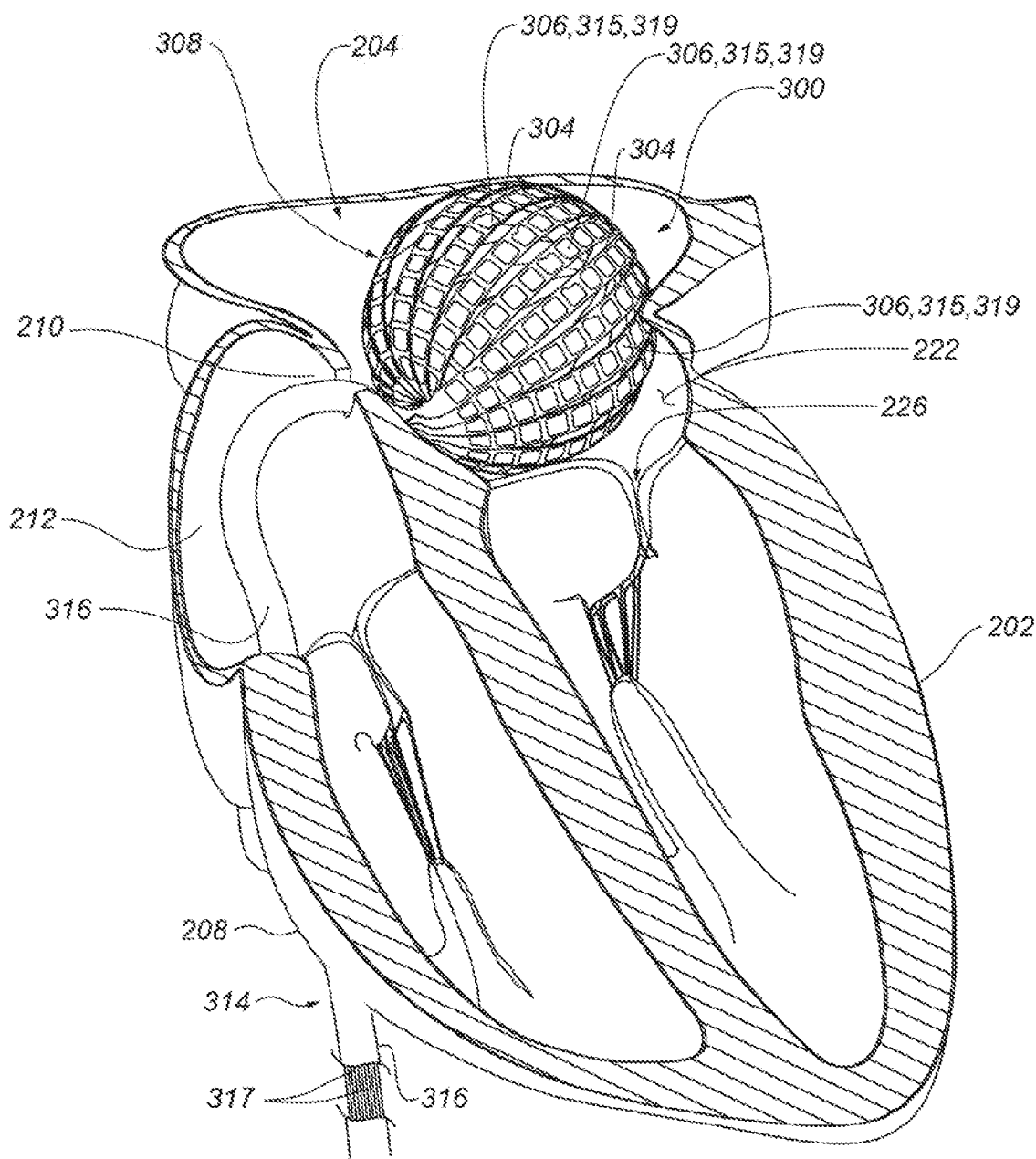
FIG. 2B is a cutaway diagram of a heart showing the electrode-based device system of FIG. 2A percutaneously placed in a left atrium of the heart in a different particular orientation according to various example embodiments.

In some embodiments, at least part of the front surface 318a of each elongate member 304 is an outward-facing surface portion, each outward-facing surface portion positionable to face away from an interior of the bodily cavity and an interior of the structure 308 toward a tissue surface of a wall of the bodily cavity in a state in which the structure 308 is positioned in the bodily cavity in an expanded or deployed configuration (e.g., FIGS. 2A, 2B). Similarly, in some embodiments, all or part of the back surface 318b of each elongate member 304 is an inward-facing surface portion opposite the respective outward-facing surface portion, each inward-facing surface portion positionable to face toward an interior of the bodily cavity and an interior of the structure 308 in the state in which the structure 308 is positioned in the bodily cavity in an expanded or deployed configuration (e.g., FIGS. 2A, 2B).

In some embodiments, all or part of the front surface 318a of each elongate member 304 is an outward-facing surface portion, each outward-facing surface portion positionable to face outwardly or away from an interior of the structure 308 when the structure 308 is an expanded or deployed configuration (e.g., FIGS. 2A, 2B, 3B, 3C). Similarly, in some embodiments, all or part of the back surface 318b of each elongate member 304 is an inward-facing surface portion opposite the respective outward-facing surface portion, each inward-facing surface portion positionable to face toward an interior of the structure 308 when the structure 308 is in an expanded or deployed configuration. In various embodiments, the various particular portions 309 of each particular elongate member 304 of the particular elongate member 304 collectively provide the front surface 318a, the back surface 318b, or both the front surface 318a and the back surface 318b of the particular elongate member 304.

In some embodiments, each elongate member 304 includes a non-helical twisted portion 345 (only one called out in each of FIGS. 3A and 3B) at a location proximate at least the respective first particular portion 309a or at least proximate shaft distal end 316b of shaft member 316. The non-helical twisted portions 345 are located outside of the shaft member 316, beyond the shaft distal end 316b, when the structure 308 is in the expanded or deployed configuration (e.g., FIGS. 2A, 2B, 3B, 3C) and also when the structure 308 is in the unexpanded or delivery configuration (e.g., FIG. 3A). According to some embodiments, various particular portions (e.g., first particular portions 309a) of the elongate members 304 in the expanded or deployed configuration (e.g., FIGS. 2A, 2B, 3B, 3C) are fanned as compared to their corresponding positions in the unexpanded or delivery configuration (e.g., FIG. 3A). In some embodiments, various portions of the elongate members 304, such as non-helical twisted portions 345, may assist in or facilitate fanning of the elongate members 304 when the structure 308 moves from the delivery configuration (e.g., FIG. 3A) to the expanded or deployed configuration (e.g., FIGS. 2A, 2B, 3B, 3C). In various embodiments, each twisted portion 345 assumes a twisted and non-helical configuration that includes only about a quarter turn of rotation (approximately 90 degrees in some embodiments, less than 110 degrees in some embodiments, or less than 90 degrees in some embodiments). This relatively small amount of twist in portions 345 allows the first particular portions 309a to be oriented with their front surfaces 318a facing outwardly from an interior of the structure 308 when the structure 308 is in the expanded or deployed configuration. Alternatively or additionally, the relatively small amount of twist in portions 345 may facilitate a movement of the first particular portions 309a during a movement from the unexpanded or delivery configuration to the expanded or deployed configuration by allowing the portions 309b to be oriented in a favorable orientation to provide at least part of the fanning action. That is, while first particular portions 309a may be too stiff to adequately bend in the direction of fanning (e.g., across their width 323) in some embodiments, portions 309b are oriented by the non-helical twisted portion 345 in their preferred bending orientation (e.g., across their thickness 327) to at least in part provide the required fanning action, according to some embodiments. It is noted that portions 309b may be pre-formed to bend outwardly when portions 309b are advanced outwardly from the confines of the catheter sheath 312 to provide some degree of autonomous fanning capability to the first particular portions 309a, for example, as described in U.S. Pat. No. 9,492,227, issued Nov. 15, 2016, which is hereby incorporated herein by reference in its entirety. According to various embodiments, each of the non-helical twisted portions 345 may twist along a same rotational direction when structure 308 is in the unexpanded or delivery configuration, the same rotational direction being a same clockwise direction or a same counterclockwise direction. In various embodiments, the non-helical twisted portions 345 of the elongate members 304 are arranged in a collective non-helical twisted configuration when the structure 308 is in the unexpanded or delivery configuration.

In some embodiments, at least various ones of the elongate members 304 may include various particular portions in which a twist or twisted region is absent or substantially absent when the structure 308 is at least in the delivery configuration shown, for example, in FIG. 3A. In other words, while a non-helical twisting portion 345 may exist at an external location beyond shaft distal end 316b of shaft member 316 (e.g., to assist deployment of the structure 308 from the delivery or unexpanded configuration (e.g., FIG. 3A) to the expanded or deployed configuration (e.g., at least FIG. 3B)), other particular portions 309 (e.g., first particular portion 309a) may be free or substantially free of any twist, according to some embodiments. In some embodiments, at least one portion 309 (e.g., first particular portion 309a) of each elongate member 304 is not arranged in a twisted configuration at least (a) when the structure 308 is in the unexpanded or delivery configuration, (b) when the structure 308 is in the expanded or deployed configuration, or both (a) and (b), as shown, e.g., in at least FIGS. 3A and 3B. Each of the phrases "substantially absent" and "substantially free" in this context means less than 15 degrees of twist in some embodiments, or less than ten degrees, five degrees, or two degrees in other embodiments. It should be noted that each of the terms "absent" and "free" in this context means less than two degrees or less than one degree, according to some embodiments.

As shown in FIG. 3A, according to some embodiments, particular portions (e.g., first particular portions 309a) of the elongate members 304 are arranged successively with respect to one another in a stacked arrangement (which may provide an example of what is sometimes referred to herein as a second stacked arrangement) when the structure 308 is in an unexpanded or delivery configuration. In various embodiments, the arrangement of the portions of the elongate members 304 in the stacked arrangement is an orderly one with each of the elongate members 304 arranged successively with respect to one another along a first direction (e.g., a stacking direction) represented by arrow 338a. It is understood that the first direction need not be a vertical or "up-down" direction but can also include other orientations. For instance, in some embodiments, various portions of elongate members 304, which are successively adjacent one another along the first direction 338a, may be stepped with respect to one another in one or more other directions. Thus, the set of elongate members 304 may be arranged in a non-stepped stacked arrangement fitting in a rectangular parallelepiped or may be arranged in a stepped stacked arrangement, for instance, fitting in a non-rectangular parallelepiped. As shown in FIG. 3A, according to some embodiments, particular portions (e.g., first particular portions 309a) of at least a set (which may provide an example of what is sometimes referred to herein as a second set) of at least three of the plurality of elongate members 304 are arranged front surface (e.g., 318a)-toward-back surface (e.g., 318b) in a stacked arrangement (which may provide an example of what is sometimes referred to herein as a second stacked arrangement) when the structure 308 is in a delivery or unexpanded configuration. According to some embodiments, each of the elongate members 304 is a strip-like member. According to some embodiments, each of the elongate members 304 is a planar member. Planar members may include at least one surface that is flat or generally flat, according to some embodiments. It is noted, according to some embodiments, that a planar member need not be flat (i.e., in two orthogonal directions) in all states or configurations. For example, a member including at least a flattened surface may be sufficiently flexible to impart some amount of curvature to the member and its flattened surface. Such a member is still considered to be, according to various embodiments, a planar member, since the flexibility of the member allows it to be bent into form in which the flattened surface may conform at least generally to a plane. According to some embodiments, each of the elongate members 304 is a non-planar member. For example, according to some embodiments, a non-planar member includes a member that does not include at least one flattened or planar surface or a member which does not have flexibility to be elastically manipulated (e.g., by bending) to include at least one flattened or planar surface.

In various embodiments, various portions of the elongate members 304 are successively arranged in an arrayed or stacked arrangement sized to be delivered through a lumen of catheter sheath 312, with each elongate member 304 positioned in the arrayed or stacked arrangement, such that the first surface 318a of the elongate member 304 is toward the second surface 318b of a first additional elongate member 304 in the arrayed or stacked arrangement, or the second surface 318b of the elongate member 304 is toward the first surface 318a of a second additional elongate member 304 in the arrayed or stacked arrangement, or both. For example, one of the outermost elongate members 304 in the arrayed or stacked arrangement is positioned in the arrayed or stacked arrangement such that its first surface 318a is toward the second surface 318b of another elongate member 304. Another of the outermost elongate member 304 is positioned in the arrayed or stacked arrangement such that its second surface 318b is toward the first surface 318a of another elongate member 304. An inboard elongate member 304 in the arrayed or stacked arrangement is positioned such that its first surface 318a is positioned toward the second surface 318b (not called out) of another elongate member 304 and the second surface 318b of inboard elongate member 304 is toward the first surface 318a of yet another elongate member 304. In some example embodiments, the first and the second surfaces 318a, 318b of the elongate members 304 are interleaved in the arrayed or stacked arrangement.

In various embodiments, each of the elongate members 304 has at least one surface that has a common characteristic with, or corresponds to, at least one surface of each of the other elongate members 304, and the elongate members 304 are arranged in an arrayed arrangement or stacked arrangement such that respective portions of the at least one surfaces of the elongate members 304 are successively arranged along the first direction of the stacked arrangement. In this respect, it is noted that the stacked arrangement does not require that the individual elongate members 304 actually rest on one another. In many instances of the stacked arrangement, the elongate members 304 or portions thereof may be separated from successively adjacent elongate members 304, or portions thereof for instance by space, such as in an embodiment of an interleaved arrangement. In some of these various embodiments, each at least one surface is a first surface, at least part thereof positionable adjacent, or proximate a tissue surface in the bodily cavity when the structure 308 is in the expanded or deployed configuration within the bodily cavity. In some of these various embodiments, each of at least the one surface is a first surface with a portion thereof that is positionable to face or contact a tissue surface in the bodily cavity when the structure 308 is in an expanded or deployed configuration within a bodily cavity. In some of these various embodiments, each at least one surface is a first surface that includes, or supports (i.e., directly or indirectly) one or more transducer elements. In some of these various embodiments, each at least one surface includes a first surface that includes, or supports (i.e., directly or indirectly) one or more transducer elements (e.g., an electrode) that are positionable adjacent a tissue surface in the bodily cavity when the structure 308 is in an expanded or deployed configuration within the bodily cavity. In some of these various embodiments, each at least one surface includes a first surface that includes, or supports (i.e., directly or indirectly) at least part of a flexible circuit structure. In some of these various embodiments, each at least one surface is a second surface with a portion thereof that is positionable to face away from a tissue surface in the bodily cavity when the structure 308 is in an expanded or deployed configuration within the bodily cavity. In some of these various embodiments, a respective portion of each at least one surface is arranged to face outwardly away from an interior or interior space of the structure 308 when the structure 308 is in an expanded or deployed configuration.

In some embodiments, various portions of the elongate members 304 are arranged successively adjacent one another when the structure 308 is in an unexpanded or delivery configuration. In some embodiments, various particular portions of the elongate members 304 face (and, in some embodiments, contact) each other when the structure 308 is in an unexpanded or delivery configuration. For example, a particular portion (e.g., a facing or contacting portion) of the front surface 318a of a first elongate member 304 may face (and, in some embodiments, contact) a particular portion (e.g., a facing or contacting portion) of the back surface 318b of a second elongate member 304 when the structure 308 is in an unexpanded or delivery configuration. In some embodiments, the respective portions (e.g., facing or contacting portions) of the first elongate member 304 and the second elongate member 304 are provided at least in part by respective ones of the first particular portions 309a of the first and the second elongate members 304. In some embodiments, at least the facing or contacting portion of the front surface 318a of the first elongate member 304 follows a contour of at least the facing or contacting portion of the back surface 318b of the second elongate member 304 when the structure is in an unexpanded or delivery configuration. For example, in the unexpanded or delivery configuration shown in FIG. 3A according to some embodiments, the first particular portions 309a of the elongate members 304 face (and, in some embodiments contact) each other in a front surface-toward-back surface manner and the contour of the front surface 318a of at least one of the elongate members 304 follows the contour of the back surface 318b of another of the elongate members 304.

In some embodiments, the respective facing or contacting portions of the first elongate member 304 and the second elongate member 304 are arranged front surface-toward-back surface as part of stacked arrangement when the structure 308 is in an unexpanded or delivery configuration. Depending on the degree of compacting of the elongate members in the stacked arrangement, partial or full separations or gaps can be present between two elongate members 304 of various ones of the successive pairs of elongate members 304 in the stacked arrangement (e.g., when the structure 308 is in an unexpanded or delivery configuration). Substantially uniform or non-uniform separations or varying sized separations between the two elongate members 304 of each successive pair of the elongate members 304 in the stacked arrangement can be present. In some example embodiments, various other elements may be disposed between two elongate members 304 of various ones of the successive pairs of the elongate members 304 in the stacked arrangement. For example, various transducer elements may be positioned between two elongate members 304 of various ones of the successive pairs of the elongate members 304 in the stacked arrangement. Various particular portions (e.g., first particular portions 309a) of the elongate members 304 can be linearly arrayed along the first direction (i.e., as represented by arrow 338a) in the stacked arrangement. In some embodiments, various particular portions (e.g., first particular portions 309a) of at least three elongate members 304 are linearly arrayed along a first direction (e.g., as represented by arrow 338a) in an arrayed arrangement when the structure is in the unexpanded or delivery configuration. In some embodiments, various particular portions (e.g., first particular portions 309a) of at least three elongate members 304 are successively arranged with respect to one another along a first direction (e.g., as represented by arrow 338a) in a stacked arrangement when the structure is in the unexpanded or delivery configuration. In some embodiments, various particular portions (e.g., first particular portions 309a) of at least three elongate members 304 are arranged front surface-toward-back surface in a stacked arrangement when the structure is in the unexpanded or delivery configuration.

Various particular portions of elongate members 304 (e.g., first particular portions 309a) may be substantially planar in form with or without some degree of curvature (e.g., curvature imparted by bending) (a) when the structure 308 is in the unexpanded or delivery configuration, (b) when the structure 308 is in the expanded or deployed configuration, or both (a) and (b). At least one of surfaces 318a and 318b need not be a flat surface. For example, at least one of surfaces 318a and 318b may include a convex or concave surface portion (e.g., across width 323) according to some embodiments. In embodiments where the electrodes 315 are considered part of their respective elongate members, the energy transmission surfaces 319 of such electrodes 315 may respectively represent an elevated surface portion of the respective front surface 318a of the respective elongate member 304, which is an example of a non-flat surface. However, in some embodiments, the energy transmission surfaces 319 may be flush (e.g., flush to the touch) with other surface portions of the respective elongate member 304, at least in some embodiments where the respective front surface 318a of the respective elongate member 304 is flat. In some example embodiments, various portions of the elongate members 304 have a shape that allows them to be successively stacked in a stacked arrangement. Stacked arrangements advantageously allow elongate members 304 to be arranged in a substantially spatially efficient manner to allow for delivery through bodily openings or catheter sheaths, thereby enabling reduced cross-sectional dimensions.

Advantageously, stacked portions of elongate members 304 allow for reduced bending stiffness about a bending axis arranged perpendicularly to the first or stacking direction of the portions of the elongate members 304 in stacked arrangement, especially when the portions of the elongate members are allowed to slide relatively with respect to one another during the bending. A reduced bending stiffness can facilitate the delivery of the stacked arrangement through catheter sheath 312 especially when catheter sheath 312 extends along a tortuous path to a bodily cavity.

The elongate members 304 may be constructed from various materials including, but not limited to, various metal and non-metal compositions, composite materials such as carbon fiber, or flexible PCB substrates. In some embodiments, each elongate member 304 includes a flexible printed structure (for example, as described with respect to FIG. 4). The elongate members 304 can include one or more material layers. The elongate members 304 may form an integral component of the transducer elements 306. The elongate members 304 may also include a support for a secondary assembly that carries the sensing and ablation transducer elements. An example of this is a stainless steel or Nitinol structure used to support transducer elements made with a flexible PCB circuit structure. In some embodiments, at least some of the elongate members 304 include resilient metallic portions. Suitable metallic materials may include stainless steel or Nitinol by way of non-limiting example. In some embodiments, structure 308 may alternatively or additionally include various members, components or assemblies other than the elongate members 304. For example, in some embodiments, the elongate members 304 may be supported on, located on, or provided on other structures including selectively expandable balloons. In some embodiments, the elongate members 304 include or take the form of flexible circuit structures (e.g., 401) which may be supported on, located on, or provided on other structures including selectively expandable balloons.

The transducers 306 may be arranged in various distributions or arrangements in various embodiments. In some embodiments, a set of one or more of the transducers 306 is located on structure 308. In some embodiments, structure 308 includes a particular portion (e.g., first particular portion 309a) of each particular elongate member 304 of the plurality of elongate members 304. According to some embodiments, at least parts (e.g., first particular portions 309a) of the elongate members 304 collectively form the structure 308. In some embodiments, a respective set of one or more of the transducers 306 is located on at least one portion (e.g., first particular portion 309a) of a respective one of the elongate members 304 of the plurality of elongate members. For example, in FIG. 3B, a set of one or more of the transducers 306 is shown located on the first particular portion 309a of each elongate member 304, which, in some embodiments, forms part of structure 308. In some embodiments, each particular elongate member 304 of the plurality of elongate members 304 comprises a length from a proximal end of the particular elongate member to the distal end 305 of the particular elongate member 304, and a plurality of sets of one or more of transducers 306 are located on distal portions (e.g., portions 309a) of the plurality of elongate members 304, each respective distal portion closer to, along the length of the respective elongate member 304, the respective distal end 305 of the respective elongate member 304 than at least some other particular portion of the respective elongate member (e.g., the respective non-helical twisted portion 345, the respective particular portion 309b, and the respective second particular portion 309c described in further detail below). In some embodiments, each particular elongate member 304 of the plurality of elongate members 304 comprises a length from the proximal portion 307, 307a, or 307b of the particular elongate member 304 to the distal end 305 of the particular elongate member 304, and a plurality of sets of one or more of transducers 306 are located on distal portions (e.g., portions 309a) of the plurality of elongate members 304, each respective distal portion closer to, along the length of the respective elongate member 304, the respective distal end 305 of the respective elongate member 304 than at least some other particular portion of the respective elongate member 304 (e.g., the respective non-helical twisted portion 345, the respective particular portion 309b, and the respective second particular portion 309c described in further detail below). In some embodiments, each respective distal portion is distinct from or does not include the respective distal end 305.

In some embodiments, various ones of the transducers 306 are spaced apart from one another in a spaced apart distribution as shown, for example, in at least FIGS. 3A and 3B at least when the structure 308 is in an expanded or deployed configuration. In some embodiments, various regions of space are located between various pairs of the transducers 306. For example, in FIG. 3B the transducer-based device system 300 includes at least a first transducer 306a, a second transducer 306b, and a third transducer 306c (all collectively referred to as examples of transducers 306). In some embodiments, each of the first, the second, and the third transducers 306a, 306b, and 306c are adjacent transducers in the spaced apart distribution. In some embodiments, the first and the second transducers 306a, 306b are located on different elongate members 304 (e.g., on the respective first portions 309a of the different elongate members 304) while the second and the third transducers 306b, 306c are located on a same elongate member 304 (e.g., on the first portion of 309a of the same elongate member 304). In some embodiments, a first region of space 350 is between the first and the second transducers 306a, 306b. In some embodiments, the first region of space 350 is not associated with any physical portion of structure 308. In some embodiments, a second region of space 360 associated with a physical portion of transducer-based device system 300 (e.g., a portion of an elongate member 304, such as at least part of the respective first portion 309a) is located between the second and the third transducers 306b, 306c. In some embodiments, each of the first and the second regions of space 350, 360 does not include a transducer or electrode thereof of electrode-based device system 300. In some embodiments, each of the first and the second regions of space 350, 360 does not include any transducer or electrode.

In various example embodiments, structures other than those shown in the accompanying figures may be employed to support or carry transducers of a transducer-based device such as a transducer-based catheter. For example, basket catheters or balloon catheters may be used to distribute the transducers in a two-dimensional or three-dimensional array.

In various example embodiments, the energy transmission surface 319 of each electrode 315 is provided by an electrically conductive surface. In some embodiments, each of the electrodes 315 is located on various surfaces of an elongate member 304 (e.g., front surfaces 318a or back surfaces 318b). In this regard, in some embodiments, each of one or more electrodes 315 is provided at least in part on the first side or front surface 318a, the second side or back surface 318b, or both the first side 318a and the second side 318b of a respective elongate member 304. In some embodiments, each of one or more electrodes 315 is located on one, but not both of the front surface 318a and back surface 318b of a respective elongate member 304. For example, various electrodes 315 may be located only on the respective front surfaces 318a of each of the various ones of the elongate members 304. Three of the electrodes 315 are identified as electrodes 315a, 315b, and 315c in FIG. 3B. Three of the energy transmission surfaces 319 are identified as 319a, 319b, and 319c in FIG. 3B. In various embodiments, it is intended or designed to have the entirety of each of various ones of the energy transmission surfaces 319 be available or exposed (e.g., without some obstruction preventing at least some of the ability) to contact non-fluid tissue at least when structure 308 is positioned in a bodily cavity in the expanded configuration. In various embodiments, it is intended or designed to have no portion of each of at least one of the energy transmission surfaces 319 contact fluidic tissue when the at least one of the energy transmission surfaces 319 contacts a contiguous portion of a non-fluidic tissue surface (e.g., a tissue surface that defines a tissue wall).

In some embodiments, like those shown in FIG. 3B, the respective first particular portions 309a of various ones of the elongate members 304 are angularly arranged with respect to one another about a first axis 335a when structure 308 is in the expanded or deployed configuration. In some embodiments, the first axis 335a is oblique with respect to an extension direction of a second axis 335b (e.g., in FIG. 3B) in which the shaft member 316 extends at the distal end 316b. In this regard, the second axis 335b may be collinear with the longitudinal axis 339d of the shaft member 316 at the distal end 316b of the shaft member 316. The second axis 335b (or longitudinal axis 339d when collinear with the second axis 335b) may extend through a center (e.g., centroid or geometric center) of a cross-section of the shaft member 316 at or adjacent the distal end 316b of the shaft member 316. It is understood that that shaft member 316 is a flexible member in some embodiments. Accordingly, the longitudinal axis 339d of shaft member 316 need not be straight within various portions of shaft member 316, but rather may follow a bend associated with these various portions of shaft member 316. Nonetheless, the longitudinal axis 339b extends outwardly in a straight-line path from the proximal and distal ends 316a, 316b of shaft member 316 (for example, as shown in FIG. 3B).

The terms "radially arranged" and "angularly arranged" may be used interchangeably, to refer to an arrangement that is the same or similar to lines of longitude distributed at least partially (e.g., hemispherically) about an axis (e.g., polar or other axis) of a body (e.g., body of revolution), which may, or may not, be spherical.

As shown in FIG. 3C, in some embodiments, at least one of the elongate members 304 crosses another of the elongate members 304 (for example, in an X configuration) (only two elongate members 304 called out in FIG. 3C for clarity) at a location proximate a first axis 335a (extending into and out of the page of FIG. 3C and illustrated with an "+" in FIG. 3C). In some embodiments, various ones of the elongate members 304 are fanned about first axis 335a. In some embodiments, first axis 335a passes through a plurality of spaced apart locations along the respective length of each of at least some of the elongate members 304 when structure 308 is in the expanded or deployed configuration. In various embodiments, first axis 335a may pass through two or more spaced apart locations along the respective length of each of at least one of the elongate members 304.

In some embodiments, each of the at least some of the plurality of elongate members 304 includes a curved portion 337 (two called out in FIG. 3B) arranged to extend along at least a portion of a respective curved path that intersects the first axis 335a at each of a respective at least two spaced apart locations along first axis 335a when the structure 308 is in an expanded or deployed configuration. In various embodiments, a curved portion 337 of an elongate member 304 may extend entirely along, or at least part way along a respective curved path that intersects the first axis 335a at each of a respective at least two spaced apart locations along first axis 335a when the structure 308 is in an expanded or deployed configuration. In some embodiments, each of the elongate members 304 includes a curved portion 337 including a curvature configured to cause the curved portion 337 to extend along at least a portion of a curved path, the curvature configured to cause the curved path to intersect the first axis 335a at each of a respective at least two spaced apart locations along the first axis 335a when structure 308 is in an expanded or deployed configuration. In some embodiments, the curved path is defined to include an imagined extension of the curved portion 337 along the curved portion's extension direction while maintaining the curved portion's curvature (e.g., radius of curvature or change in radius of curvature) at a location where the curved portion 337 ends and the imagined extension begins. In some embodiments, each curved portion 337 may extend entirely along, or at least part way along, the respective curved path to physically intersect at least one of the respective at least two spaced apart locations along the first axis 335a. In some particular embodiments, no physical portion of a given elongate member 304 of an employed structure intersects some of the at least two spaced apart locations along the first axis 335a intersected by the respective curved path associated with the curved portion 337 of the given elongate member 304. In various embodiments, the curved path is an arcuate path. In various embodiments, at least the portion of the curved path extended along by curved portion 337 is arcuate. In some embodiments, at least a first elongate member 304 crosses a second elongate member 304 (e.g., in an X configuration) at each of at least one of the respective at least two spaced apart locations along the first axis 335a intersected by at least the portion of the respective curved path extended along by the curved portion 337 of the second elongate member 304 when the structure 308 is in the expanded or deployed configuration. In some embodiments, at least a first elongate member 304 crosses a second elongate member 304 at each of the respective at least two spaced apart locations along the first axis 335a intersected by at least the portion of the respective curved path extended along by the curved portion 337 of the second elongate member 304 when the structure 308 is in an expanded or deployed configuration. In various embodiments, each respective curved portion 337 is arranged to extend along at least a portion of a respective curved path that intersects the first axis 335a at each of a respective at least two spaced apart locations along first axis 335a when the structure 308 is in an expanded or deployed configuration.

In various embodiments, various particular portions of all of the plurality of elongate members 304 are circumferentially arranged about first axis 335a when the structure 308 is in an expanded or deployed configuration. For example, when the structure 308 is the expanded or deployed configuration, at least respective parts of the elongate members 304 (e.g., at least the first particular portion 309a or the curved portion 337) are circumferentially arranged about the first axis 335a, in the same or similar manner as lines of longitude about an axis of a body, which body may, or may not, be spherical. In some embodiments, at least one portion (e.g., the first particular portion 309a or the curved portion 337) of each of the elongate members 304 extends like a line of longitude about the structure 308 when the structure is in the deployed or expanded configuration. In some embodiments, at least one portion (e.g., at least the first particular portion 309a or the curved portion 337) of each elongate member 304 is not arranged in a helical configuration when the structure 308 is in an expanded or deployed configuration. It is noted in various embodiments that various particular portions of the elongate members may include configurations in each of the delivery and the deployed configurations that differ from one another on aspects other than differences in size. Other aspects can include inherent differences in structure. For example, according to some embodiments, the first particular portions 309a of the elongate members 304 are arranged like lines of longitude in the expanded or deployed configuration shown in FIG. 3B and are arranged in a stacked configuration in an unexpanded or delivery configuration shown in FIG. 3A. Without limitation, other arrangements of some of the various particular portions of the elongate members 304 are possible in various embodiments. In some embodiments, at least one portion (e.g., first particular portion 309*a*) of each elongate member 304 is not arranged in a helical configuration when the structure 308 is in an unexpanded or delivery configuration. In some embodiments, at least one portion (e.g., first particular portion 309*a*) of each elongate member 304 is not arranged in a helical configuration when the structure 308 is in an expanded or deployed configuration.

In some embodiments, each of the elongate members 304 includes a respective portion (e.g., at least part of first particular portion 309*a* or at least part of curved portion 337) radially spaced from the first axis 335*a* when the structure 308 is in an expanded or deployed configuration, the respective portions of the elongate members 304 circumferentially arranged about the first axis 335*a* when the structure is in the expanded configuration. Similarly, in various embodiments, at least some of the electrodes 315 are radially spaced about or from a first axis 335*a* when structure 308 is in an expanded or deployed configuration. In various embodiments, at least some of the electrodes 315 are circumferentially arranged about first axis 335*a* when structure 308 is in the deployed configuration. For example, various ones of the electrodes 315 are circumferentially arranged about first axis 335*a* in the expanded or deployed configuration in at least some of the embodiments associated with various ones of at least FIG. 3B. It is understood that although electrodes 315 are referred to in these described embodiments, the same analysis applies to the corresponding transducers 306 in some embodiments. In various embodiments, the electrodes 315 are arranged such that the first axis 335*a* passes through, or alternatively does not pass through a particular electrode (e.g., a central electrode). The presence or non-presence of such a particular electrode may be dependent on various factors including a required size of the device and particular anatomy characteristics into which the device is deployed. For example, different bodily cavities have different sizes and shapes and, therefore, different sizes and shapes of various parts of the transducer-based device system 300 (e.g., structure 308) may be appropriate to match the different sizes and shapes of the bodily cavities, according to some embodiments. Different bodily cavities may have different anatomical features or different positionings of various anatomical features. Accordingly, in some embodiments, it may be beneficial to have an arrangement of transducers or electrodes in which an electrode intersected by first axis 335*a* exists. In other applications, it may be beneficial to have an arrangement of transducers or electrodes in which an electrode intersected by first axis 335*a* does not exist.

It may be noted that distances between adjacent ones of the elongate members 304 shown in at least FIG. 3B vary as elongate members 304 extend toward first axis 335*a* when structure 308 is in the deployed configuration. In some cases, the varying distances between adjacent elongate members 304 in an expanded or deployed configuration may give rise to shape, size or dimensional constraints for the electrodes 315 located on the elongate members 304. In some cases, the overlapping portions of various ones of the elongate members 304 in the deployed configuration may give rise to shape, size or dimensional constraints for the electrodes 315 located on the portions of the various ones of the elongate members 304. For example, it may be desirable to reduce a surface area of an electrode adjacent an overlap region on an overlapped elongate member to accommodate the reduced exposed surface area of the overlapped elongate member in the region adjacent the overlap region.

In various embodiments, the respective shape of various electrically conductive surfaces (e.g., energy transmission surfaces 319) of various ones of the electrodes 315 vary among the electrodes 315. In various embodiments, the respective shape of various electrically conductive surfaces (e.g., energy transmission surfaces 319) of various ones of the electrodes 315 vary among the electrodes 315 in accordance with their proximity to first axis 335*a*. In various embodiments, one or more dimensions or sizes of various electrically conductive surfaces (e.g., energy transmission surfaces 319) of at least some of the electrodes 315 vary among the electrodes 315. In various embodiments, one or more dimensional sizes of various electrically conductive surfaces (e.g., energy transmission surfaces 319) of at least some of the electrodes 315 vary in accordance with their proximity to first axis 335*a*. The shape or size variances associated with various ones of the electrodes 315 may be motivated for various reasons. For example, in various embodiments, the shapes or sizes of various ones of the electrodes 315 may be controlled in response to various ones of the aforementioned size or dimensional constraints.

Referring back to FIGS. 2A and 2B, it is noted that structure 308 may be required to be positioned in, or to be positionable in, a bodily cavity (e.g., left atrium 204) in different positions or orientations. The required variances in position, orientation, or both position and orientation may be motivated for different reasons. For example, different regions of the bodily cavity may need to be diagnosed or treated based on typical and non-typical anatomical variations as well as variances in the anatomical regions that are susceptible to a particular disease or diseases, or are afflicted by a particular disease or diseases. In various embodiments, the ability to position the structure 308 at multiple different locations or in multiple different orientations may be dependent on the ability of shaft member 316 to bend, or be bent, in multiple different directions. For example, a comparison of FIGS. 2A and 2B shows different degrees of bending in shaft member 316 required to position structure 308 into two different sets of positions and orientations. In some embodiments, different degrees of bending in shaft member 316 are required during percutaneous or intravascular delivery of at least part of catheter 314 especially through bodily opening providing a tortuous path. In some embodiments, it is desired that shaft member 316 include at least one bendable portion that is bendable in each of at least two intersecting planes (e.g., two orthogonal planes) to position structure 308 in different positions and orientations. The at least one bendable portion of the shaft member 316 may, in some embodiments, be actively bendable in each of the at least two intersecting planes. For example, in some embodiments, catheter 314 may itself include various controls coupled to the at least one bendable portion via various control elements to bend the at least one portion in response to activation of at least some of the control elements. By way of non-limiting example, catheter 314 may include various actuators, each coupled to a respective set of control lines to bend the at least one bendable portion in at least one of the at least two intersecting planes. By way of non-limiting example, catheter 314 may include various actuators, each coupled to a respective set of control lines located internally within the catheter 314 (e.g., within a lumen in shaft member 316) to bend the at least one bendable portion in at least one of the at least two intersecting planes. In some embodiments, at least one bendable portion of the shaft member 316 may, in some embodiments, be passively bendable in each of the at least two intersecting planes. For example, the at least one bendable portion is sufficiently compliant to bend in response to externally applied force or forces to catheter 314 (e.g., external forces applied to an outer or external surface of shaft member 316).

In various embodiments, the ability to position the structure 308 at multiple different locations or in multiple different orientations may be dependent on the ability of various particular portions of each of at least some of the elongate members 304 to bend, or be bent, in multiple different directions. In various embodiments, the ability to position the structure 308 at multiple different locations or in multiple different orientations may be dependent on the ability of various particular portions of each of at least some of the elongate members 304 to bend, or be bent, in each of the at least two intersecting planes (e.g., two orthogonal planes).

In some cases, various arrangements of particular portions of the elongate members 304 may hinder or otherwise restrict the ability of various parts of the elongate members 304 from bending in multiples directions (e.g., bending in each of the at least two intersecting planes). For example, in a manner similar to the stacked arrangement of the first particular portions 309a, the second particular portions 309c may also be stacked front surface 318a-toward-back surface 318b along a particular direction 338b (FIG. 3A) in a stacked arrangement according to some embodiments. In various embodiments, the second particular portions 309c may be located within catheter shaft 316 itself. In a manner similar to the spatially efficient stacked arrangement adopted, according to some embodiments, by the first particular portions 309a to reduce the overall cross-sectional size of the catheter sheath 312 which the first particular portions 309a are delivered therethrough, stacking of the second particular portions 309c may be employed to create a spatially efficient arrangement that can be advantageously employed to reduce a cross-sectional size of the catheter shaft 316 in which the second particular portions 309c are located in or housed in according to some embodiments. It is noted, however, that, in some cases, a particular arrangement of particular portions of the elongate members 304 (e.g., a stacked arrangement of second particular portions 309c) may have different bending characteristics or degrees of flexibility when required to bend in different directions (e.g., when required to bend in each of the at least two intersecting planes). For example, the stacked arrangement of second particular portions 309c may bend more easily in their stacking direction 338b than in a direction orthogonal to their stacking direction 338b (e.g., in a direction across the widths 323 of the second particular portions 309c). In some cases, each width 323 is larger than the thickness 327 of the particular portion of the elongate member 304 and, thus, bending across the width is restricted or impeded by a greater amount than bending across the thickness (i.e., the elongate members being stiffer across their widths 323 than across their thickness 327). It is noted that different resistances to bending in different directions is not confined to stacked arrangements as other arrangements may also be affected by this condition. For example, an arrangement of various members whose cross-section comprises different dimensions in each of at least two different bending directions may typically experience different bending resistances in each of the at least two different bending directions. By way of another example, an arrangement of various members whose cross-section comprises different distributions of the members in each of at least two different bending directions may typically experience different bending resistances in each of the at least two different bending directions.

In some cases, differential bending characteristics in each of multiple bending directions may hinder positioning of structure 308. In some cases, bending resistance in each of at least one of multiple bending directions may hinder positioning of structure 308. In some cases, a particular arrangement of particular portions of the elongate members 304 is located within shaft member 316. If the particular arrangement of particular portions of the elongate members 304 provides sufficient bending resistance in each of at least one of multiple bending directions, bending of various portions of the shaft member 316 may be impeded or restricted along each of at least one particular direction. It is noted that bending resistance along a particular direction is not solely attributable to stacked arrangements and may also be associated with other types of arrangements of various particular portions of the elongate members 304. For example, a bundled arrangement of particular portions of the elongate members 304 may provide bending resistance along each of at least one particular direction.

Various embodiments of the present invention may be employed to, among other things, address these bending restrictions at least with a helical configuration in some embodiments, or a twisted, non-helical configuration in some embodiments, of the elongate members 304, which facilitate improved bending characteristics thereof. Consequently, improved percutaneous or intravascular navigation of the shaft member 316 and positioning of the structure 308 within a bodily cavity may be achieved.

Figure 3D:
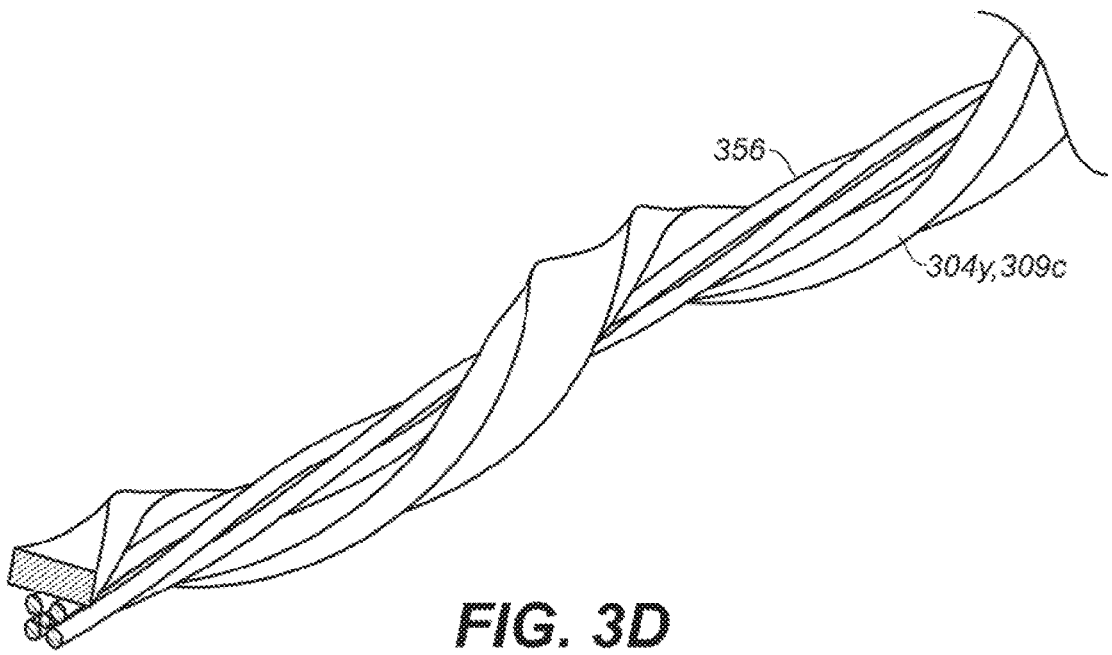
FIG. 3D illustrates, according to some embodiments, a single helical winding configuration of one or more elongate member portions of a medical device system, such as, but not limited to, a medical device system of FIG. 1, 2A, 2B, 3A, 3B, or 3C.
Figure 3E:
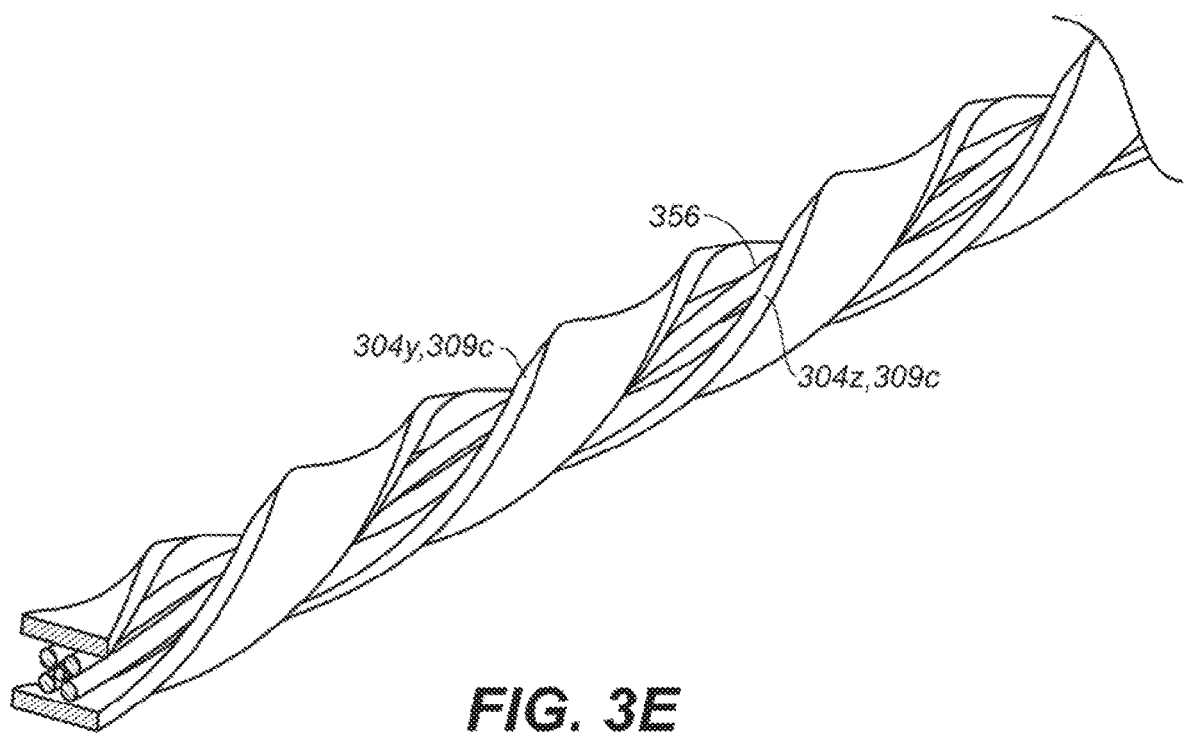
FIG. 3E illustrates, according to some embodiments, a double helical winding configuration of one or more elongate member portions of a medical device system, such as, but not limited to, a medical device system of FIG. 1, 2A, 2B, 3A, 3B, or 3C.
Figure 3F:
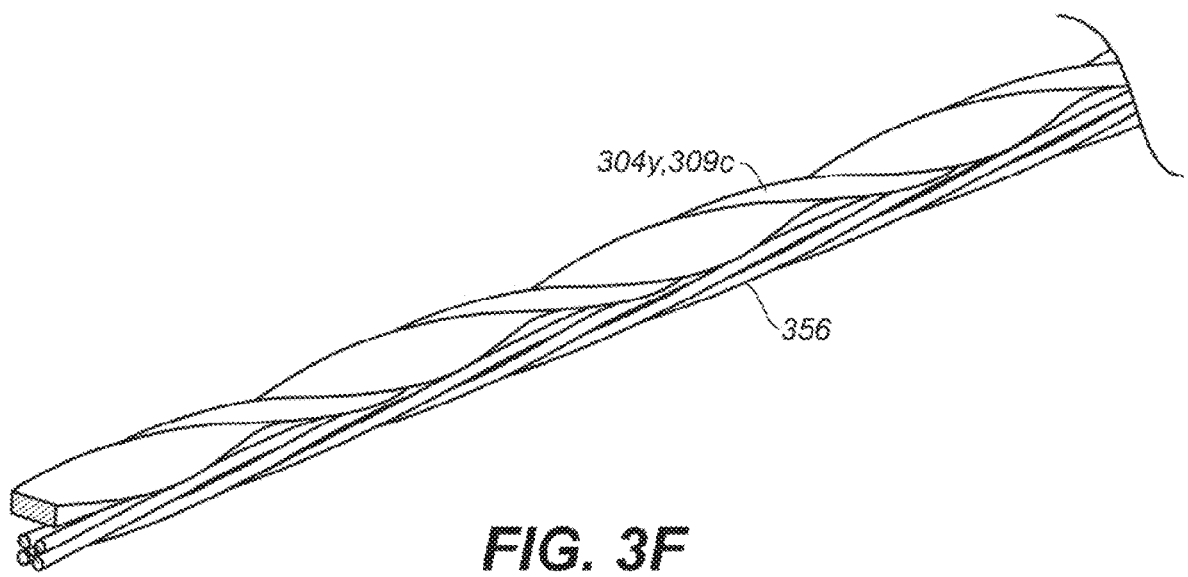
FIG. 3F illustrates, according to some embodiments, a non-helical, twisted configuration of one or more elongate member portions of a medical device system, such as, but not limited to, a medical device system of FIG. 1, 2A, 2B, 3A, 3B, or 3C.
Figure 3G:
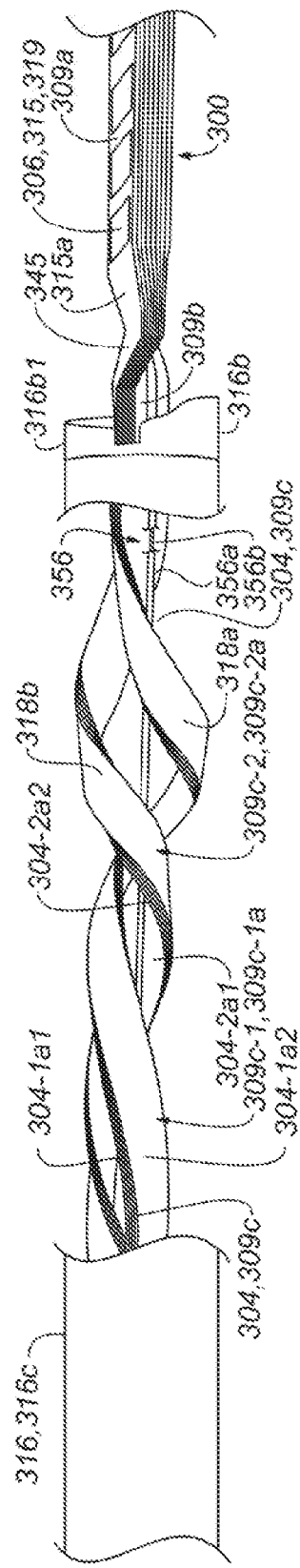
FIG. 3G is a partially sectioned view of a percutaneously or intravascularly deliverable portion of a shaft member and a plurality of helically configured elongate member portions, according to some embodiments, of a medical device system, such as, but not limited to, a medical device system of FIG. 1, 2A, 2B, 3A, 3B, or 3C.
Figure 3H:
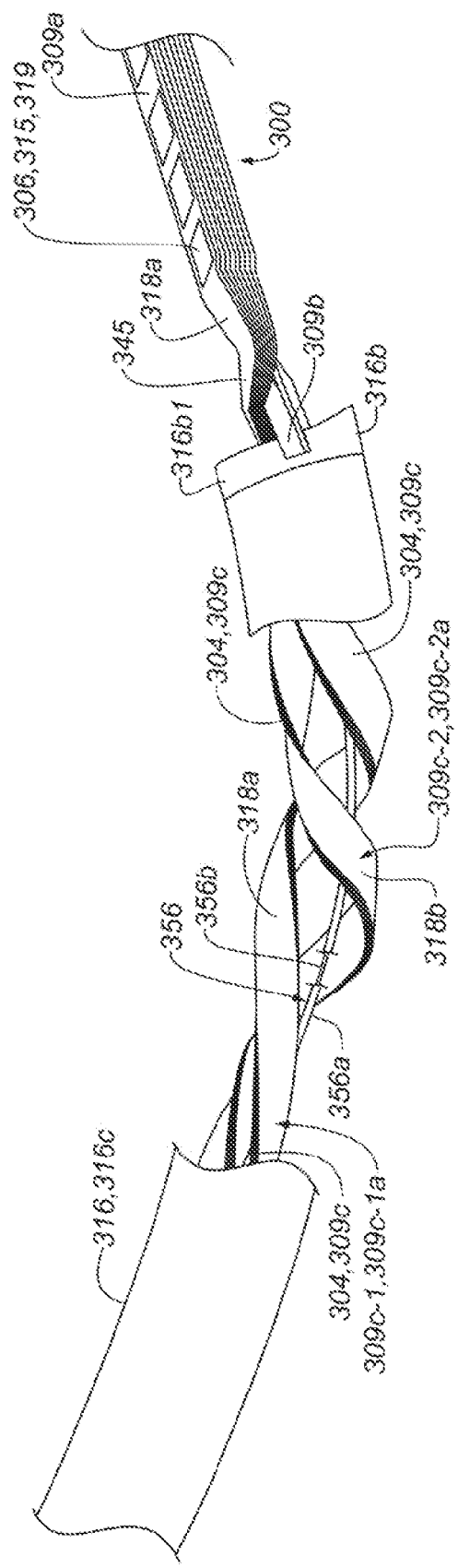
FIG. 3H is a partially sectioned view of a percutaneously or intravascularly deliverable portion of the shaft member and the plurality of helically configured elongate member portions of FIG. 3G, according to some embodiments.

For example, FIGS. 3G and 3H show detailed portions of shaft member 316 and portions of elongate members 304 in a double-helical configuration when structure 308 is in an unexpanded or delivery configuration (e.g., as shown in FIG. 3A), according to some embodiments. For clarity, various portions of the shaft member 316 are not shown in FIGS. 3G and 3H to allow various particular portions (e.g., second particular portions 309c) of the elongate members 304 to be seen. For further clarity, catheter sheath 312 is also not shown in FIGS. 3G and 3H. As can be seen by a comparison of FIGS. 3G and 3H, the double-helical configuration of portions of elongate members 304 within shaft member 316 allow for improved bending characteristics of at least such portions of the elongate members 304, as well as of at least the corresponding portion of shaft member 316.

Turning to FIG. 3G, according to some embodiments, each of the elongate members 304 includes a second portion or second particular portion 309c. Each second particular portion 309c of each elongate member 304 may be arranged in a helical configuration when the structure 308 is in an unexpanded or delivery configuration. According to various embodiments, such a helical configuration allows for uniform or substantially uniform bending characteristics of the shaft member 316 in at least two different bending directions. For example, the helical configuration distributes the second particular portions 309c circumferentially around an axis (e.g., a longitudinal axis of the shaft member 316 or other axis of rotation) in a series of spaced apart coils, each coil axially spaced from an adjacent coil. The presence of these axial spaces allows the second particular portions 309c to bend with substantially the same amount of bending resistance in each of the at least two different bending directions. Accordingly, in various embodiments, such a helical configuration may facilitate reduced differences in bending resistance in each of at least two different bending directions. In this regard, it is noted that the helical configuration of the elongate members 304, e.g., within portions 309c, provides improved bending characteristics, in contrast to the non-helical twisted portion 345, which facilitates changing of the structure 308 between its delivery or unexpanded configuration and its deployed or expanded configuration. Additionally, in some embodiments, each of the helical second particular portions 309c is spaced from a central rotational axis along which they are wound while the non-helical twisted portions 345 are not spaced from their central rotational axis. In some embodiments, the helical configuration includes at least 360 degrees of rotation when the structure 308 is in the unexpanded or delivery configuration. In some embodiments, the helical configuration includes at least 540 degrees of rotation when the structure 308 is in the unexpanded or delivery configuration. In some embodiments, the helical configuration includes at least 720 degrees of rotation when the structure 308 is in the unexpanded or delivery configuration. Higher degrees of rotation may facilitate improved bending characteristics in different directions, e.g., over a longer region or length of the elongate members 304.

Although FIGS. 3G and 3H illustrate a multi-helical configuration according to some embodiments, other helical configurations or non-helical twisted configurations including at least 360 degrees of rotation also improve bending characteristics as compared to non-helical non-twisted or substantially non-twisted configurations. For example, FIG. 3D illustrates a set 304y of at least some of the elongate members 304 arranged in a single helical configuration rotating around a plurality of control elements 356 (only one instance of a control element 356 is called out in FIG. 3D for clarity), according to some embodiments. For another example, FIG. 3E illustrates a first set 304y of at least some of the elongate members 304 and a second set 304z of at least some of the elongate members 304 arranged in a double helical configuration rotating around a plurality of control elements 356 (only one instance of a control element 356 is called out in FIG. 3E for clarity), according to some embodiments. For yet another example, FIG. 3F illustrates a set 304y of at least some of the elongate members 304 arranged in a twisted, non-helical configuration rotating alongside a plurality of control elements 356 (only one instance of a control element 356 is called out in FIG. 3F for clarity), according to some embodiments.

As can be seen by a comparison of the example helical configurations of FIGS. 3D and 3E with the example twisted, non-helical configuration of FIG. 3F, the helical configurations provide an interior channel, where the axis of rotation resides, for the one or more control elements 356 to reside. Accordingly, a set of one or more elongate members 304 in a helical configuration may rotate around the one or more control elements 356. On the other hand, because the twisted, non-helical configuration intersects its axis of rotation, the one or more control elements 356 are located alongside the set 304y of at least some of the elongate members 304 in FIG. 3F, instead of the set 304y of at least some of the elongate members 304 rotating around the one or more control elements 356. While, in some implementations, a helical configuration with at least some of the elongate members 304 rotating or wrapping around one or more control elements 356 (e.g., FIG. 3D, 3E, or 3G and 3H) may provide improved bending characteristics and space utilization efficiency characteristics as compared to a non-helical twisted configuration with at least some of the members 304 rotating side-by-side with one or more control elements 356 (e.g., FIG. 3F), it may be less expensive, in some implementations, to produce a non-helical twisted configuration (e.g., FIG. 3F) as compared to a helical configuration (e.g., FIG. 3D, 3E, or 3G and 3H), while still maintaining improved bending characteristics as compared to a non-helical, non-twisted configuration. Accordingly, depending on need, a helical configuration or a non-helical, twisted configuration may be preferable.

Although FIGS. 3D, 3E, and 3F each illustrate five control elements 356, different numbers of control elements may be implemented in different embodiments. Also, it is noted that the control elements 356 illustrated in FIGS. 3D, 3E, and 3F are themselves arranged in a helical configuration, which may further improve bending characteristics. Further, each of FIGS. 3D, 3E, and 3F illustrate a single, twisting, thick 'block' as a set of elongate members (e.g., 304y, 304z), it is understood that such single, rotating, 'thick block' is intended to illustrate in a simple manner for clarity at least some of the elongate members 304, depending on the embodiment, and the illustrated thickness of such single, 'thick block' is not intended to limit or define the actual thickness of any particular elongate member 304 or stack of elongate members 304. Further, different embodiments utilize different numbers of elongate members. Accordingly, for example, the first set 304y of at least some of the elongate members 304 illustrated in FIG. 3D may or may not have the same number of elongate members 304 as the first set 304y of at least some of the elongate members 304 illustrated in FIG. 3E or FIG. 3F. The same applies to other illustrations in the figures, such as at least the second set 304z of at least some of the elongate members 304 illustrated in FIG. 3E with respect to the first set 304y of at least some of the elongate members 304 illustrated in each of FIGS. 3D, 3E, and 3F. Also, although FIGS. 3D, 3E, and 3F illustrate particular locations of control elements 356, other embodiments have one or more control elements 356 in other locations.

In various embodiments, each of the plurality of the elongate members 304 includes a first portion (e.g., first portion or first particular portion 309a) that extends outwardly from the shaft distal end 316b of the shaft member 316 and further includes a second portion (e.g., second portion or second particular portion 309c) that is located within the elongated portion 316c of the shaft member 316. According to various embodiments, at least one portion (e.g., first particular portion 309a) of each elongate member 304 has located thereon a respective set of one or more of the transducers 306. In some embodiments, at least one portion (e.g., first particular portion 309a) of each elongate member 304 other than the second portion (e.g., second particular portion 309c) of the elongate member 304 has located thereon a respective set of one or more of the transducers 306. According to some embodiments, no transducer or electrode (e.g., a transducer selectively operable to transmit energy) is located on the second portions (e.g., second particular portions 309c) of the elongate members 304. In some embodiments, each second portion (e.g., second particular portion 309c) of each of at least one of the elongate members 304 does not include any transducers or electrodes. In some embodiments, each second portion (e.g., second particular portion 309c) located within the elongated portion 316c of the shaft member 316 includes a helical configuration (e.g., FIG. 3D, 3E, or 3G and 3H) or includes a non-helical twisted configuration (e.g., FIG. 3F). In some embodiments, each second portion located within the elongated portion 316c of the shaft member 316 includes a helical configuration that includes at least 360 degrees of rotation, at least 540 degrees of rotation in some embodiments, or at least 720 degrees of rotation in some embodiments to facilitate enhanced bending characteristics in 360 degrees. In some embodiments, each second portion located within the elongated portion 316c of the shaft member 316 includes a twisted, non-helical configuration that includes at least 360 degrees of rotation, at least 540 degrees of rotation in some embodiments, or at least 720 degrees of rotation in some embodiments to facilitate enhanced bending characteristics in 360 degrees.

In various embodiments, the second particular portions 309c of the elongate members 304 each maintain a helical configuration or a twisted, non-helical configuration during a movement of the structure 308 between the unexpanded or delivery configuration and the expanded or deployed configuration. In various embodiments, the second particular portions 309c of the elongate members 304 each maintain a helical configuration or a twisted, non-helical configuration in each of the unexpanded or delivery configuration and the expanded or deployed configuration. In various embodiments, the second particular portions 309c of the elongate members 304 are arranged in a particular configuration that (a) remains sufficiently small in size, or (b) undergoes no particular change in size sufficient to restrict the second portions 309c from being too large, to be percutaneously or intravascularly deliverable to a bodily cavity when the structure 308 is moved from the unexpanded or delivery configuration to the expanded or deployed configuration. For example, in some embodiments, the act of moving structure 308 from the unexpanded or delivery configuration to the expanded or deployed configuration involves no particular actuation or transmission of force that would increase a size (e.g., a cross-sectional diameter) of a particular configuration (e.g., the helical configuration) of the second particular portions 309c that would restrict the second particular portions 309c from being percutaneously or intravascularly deliverable to a bodily cavity. Even though the second particular portions 309c are located, confined, or encapsulated within a particular structure (e.g., a lumen of elongated potion 316c of shaft member 316) in some embodiments, the second particular portions 309c of the elongate members 304 are arranged in a particular configuration, according to some embodiments, that would remain sufficiently small in size to be percutaneously or intravascularly deliverable to a bodily cavity in absence of the particular structure, when the structure 308 is moved from the unexpanded or delivery configuration to the expanded or deployed configuration.

Returning to a comparison of FIGS. 3G and 3H, such figures show that the helical configuration of the second particular portions 309c, according to some embodiments, facilitates bending of at least the second particular portions 309c especially in each of multiple different directions (e.g., (a) different directions lying on one plane or (b) different directions lying in each of at least two intersecting planes, or both (a) and (b)). This facilitated bending can enhance the ability to maneuver structure 308 into different positions or different orientations. In some embodiments in which the second particular portions 309c are located within the elongated portion 316c of shaft member 316, each of various ones of the second particular portions 309c may employ a helical configuration to enhance an ability of shaft member 316 to bend in each of different directions. As discussed above, a twisted, non-helical configuration of a portion or portions of one or more elongate members within the shaft member 316 provides similar bending enhancements.

In various embodiments, where certain particular portions of the elongate members are arranged in a first particular configuration to provide a particular desired function (e.g., spatial efficiency) with the particular configuration not conducive or best suited for a second particular desired function (e.g., improved bendability), the incorporation of the helical or twisted, non-helical second particular portions may allow the second particular desired function to be achieved at least in part. For example, if the particular portions 309b of the elongate members 304 continued in their non-twisted, non-helical stacked configuration through a particular part of the elongate portion 316c of the shaft member 316, their non-twisted, non-helical stacked configuration may restrict or hinder the bendability of the particular part of the elongated portion 316c of the shaft member 316 in at least one direction. The use the helical or twisted, non-helical second particular portions 309c may be employed to improve the bendability of the particular part of the elongate portion 316c of the shaft member 316 in at least the one direction or in another direction.

In some embodiments, the second particular portions 309c of the elongate members 304 are arranged in a collective arrangement that may be motivated for various particular reasons. For example, in various embodiments, it may be desired that the second particular portions 309c be arranged in a particular arrangement that can accommodate various constraints (e.g., spatial constraints). In some embodiments in which the second particular portions 309c are contained within the elongated portion 316c of shaft member 316, the second particular portions 309c are preferably arranged in an arrangement that can accommodate the spatial confines of the elongated portion 316c. In some embodiments, the second particular portions 309c are arranged in a non-orderly, random, or quasi-random arrangement with no substantial form or structure to the arrangement. In some embodiments, the second particular portions 309c are arranged in an orderly arrangement.

In many cases, an orderly arrangement is typically more spatially efficient than a non-orderly arrangement. A stacked arrangement is an example of an orderly arrangement that is spatially efficient. A nested configuration is also an example of an orderly configuration that is spatially efficient. For example, a particular portion of a first elongate member 304 may be nested with a particular portion of at least a second elongate member 304 at least when the structure is in (a) an unexpanded or delivery configuration, (b) an expanded or deployed configuration or in each of (a) and (b). In some embodiments, the second particular portion 309c of a first elongate member 304 may be nested with the second particular portion 309c of at least a second elongate member 304 at least when the structure is in (a) an unexpanded or delivery configuration, (b) an expanded or deployed configuration, or in each of (a) and (b). In some embodiments, particular portions of the elongate members 304 are arranged such that at least a particular portion of the front surface 318a of a first elongate member 304 follows a contour of at least a particular portion 318b of a second elongate member 304 at least when the structure is in (a) an unexpanded or delivery configuration, (b) an expanded or deployed configuration, or in each of (a) and (b). In some embodiments the particular portion of the front surface 318a of the first elongate member 304 faces (and, in some embodiments contacts) the particular portion 318b of a second elongate member 304 at least when the structure is in (a) an unexpanded or delivery configuration, (b) an expanded or deployed configuration or in each of (a) and (b) and as such may be considered to be facing or contacting portions. In some embodiments, particular portions of the elongate members 304 are arranged such that at least a particular portion of the front surface 318a of a first elongate member 304 follows a contour of at least the particular portion 318b of a second elongate member 304 throughout the helical rotation of the second portion 309c of the second elongate member 304 at least when the structure is in (a) an unexpanded or delivery configuration, (b) an expanded or deployed configuration or in each of (a) and (b).

FIGS. 3G and 3H illustrate a first set 309c-1 of the second particular portions 309c of a first set 309c-1a of the elongate members 304, and a second set 309c-2 of the second particular portions 309c of a second set 309c-2a of the elongate members 304. The first set 309c-1 of the second particular portions 309c may correspond to the portion of the first set 304y of at least some of the elongate members 304 illustrated in FIG. 3E, according to some embodiments, and the second set 309c-2 of the second particular portions 309c may correspond to the portion of the second set 304z of at least some of the elongate members 304 illustrated in FIG. 3E, according to some embodiments. As shown in FIGS. 3G and 3H, the first set 309c-1 of the second particular portions 309c of the first set 309c-1a of the elongate members 304 may be axially or longitudinally (along the longitudinal axis of the shaft member 316) offset from the second set 309c-2 of the second particular portions 309c of the second set 309c-2a of the elongate members 304 according to some embodiments. In some embodiments, the first set 309c-1a of the elongate members 304 includes at least two or at least three elongate members 304. In some embodiments, the second set 309c-2a of the elongate members 304 includes at least two or at least three elongate members 304. In some embodiments, the first set 309c-1a of the elongate members 304 has exactly four elongate members 304, and the second set 309c-2a of the elongate members 304 has exactly four elongate members 304. In this regard, as with the above-discussion regarding FIGS. 3D, 3E, and 3F regarding the possibilities of different numbers of elongate members 304 in different embodiments, the first set 309c-1a of the elongate members 304 may have the same number of elongate members 304 as the second set 309c-2a of the elongate members 304 in some embodiments, but in other embodiments, the first set 309c-1a of the elongate members 304 has a different number of elongate members 304 than the second set 309c-2a of the elongate members 304. The different number may be plus-or-minus one (1), e.g., in the case of an odd number of elongate members 304, such as seven elongate members 304, which may be provided in some embodiments. In some embodiments, the different number is plus-or-minus 20% or 10% to allow for differences, but still ensuring an integer number of elongate members 304 in each set 309c-1a, 309c-2a. In some embodiments, the different number is plus-or-minus 20% or 10% to allow for differences, but still facilitating substantially balanced bending characteristics. In various embodiments, the elongate members 304 of the first set 309c-1a are other than the elongate members of the second set 309c-2.

In some embodiments, e.g., as shown in FIGS. 3G and 3H, the first set 309c-1 of the second particular portions 309c of the first set 309c-1a of the elongate members 304 forms a first collective helical configuration, and the second set 309c-2 of the second particular portions 309c of the second set 309c-2a of the elongate members 304 forms a second collective helical configuration. In this regard, FIGS. 3G and 3H show an example where a particular portion (e.g., second particular portion 309c) of a first elongate member 304-1a1 in the first set 309c-1a is nested with a particular portion (e.g., second particular portion 309c) of at least an adjacent second elongate member 304-1a2 in the first set 309c-1a at least when the structure 308 is in an unexpanded or delivery configuration, according to some embodiments. Since, in some embodiments, the second particular portions 309c maintain their helical configurations when the structure 308 moves from its delivery or unexpanded configuration to its deployed or expanded configuration, the particular portion (e.g., second particular portion 309c) of the first elongate member 304-1a1 in the first set 309c-1a also may be nested with the particular portion (e.g., second particular portion 309c) of at least the adjacent second elongate member 304-1a2 in the first set 309c-1a when the structure 308 is in an expanded or deployed configuration, according to some embodiments. The same unexpanded or delivery configuration and expanded or deployed configuration nesting characteristics apply to adjacent first and second elongate members 304-2a1, 304-2a2, respectively, in the second set 309c-2a of the elongate members 304, according to some embodiments.

In some embodiments, particular portions of the elongate members 304 are arranged such that at least a particular portion of the front surface 318a of a first elongate member 304 (e.g., first elongate member 304-1a1 of first set 309c-1a) follows a contour of at least a particular portion of the back surface 318b of a second elongate member 304 (e.g., second elongate member 304-1a2 of first set 309c-1a) at least (a) when the structure 308 is in an unexpanded or delivery configuration (e.g., as shown in FIGS. 3G and 3H), (b) when the structure 308 is in an expanded or deployed configuration (e.g., due to the retention of the helical configuration of the second particular portions 309c when the structure moves to the expanded or delivery configuration in some embodiments), or both (a) and (b). In some embodiments, the particular portion of the front surface 318a of the first elongate member 304 faces the particular portion of the back surface 318b of the second elongate member 304 at least (a) when the structure 308 is in an unexpanded or delivery configuration, (b) when the structure 308 is in an expanded or deployed configuration, or both (a) and (b). In some embodiments, the particular portion of the front surface 318a of the first elongate member 304 faces (and, in some embodiments contacts) the particular portion of the back surface 318b of the second elongate member 304 at least (a) when the structure 308 is in an unexpanded or delivery configuration, (b) when the structure 308 is in an expanded or deployed configuration, or both (a) and (b) and, as such, the particular portion of the front surface 318a of the first elongate member 304 and the particular portion of the back surface 318b of the second elongate member 304 may be considered facing or contacting portions. In some embodiments, the particular portion of the front surface 318a of the first elongate member 304 and the particular portion of the back surface 318b of the second elongate member 304 are provided by the respective second particular portions 309c of the respective elongate members 304. In some embodiments, the particular portion of the front surface 318a of the first elongate member 304 (e.g., first elongate member 304-1a1 of first set 309c-1a) follows the contour of (and, in some embodiments, contacts) at least the particular portion of the back surface 318b of the second elongate member 304 (e.g., second elongate member 304-1a2 of first set 309c-1a) throughout the helical rotation of the second portion 309c of the second elongate member 304 at least (a) when the structure 308 is in an unexpanded or delivery configuration, (b) when the structure 308 is in an expanded or deployed configuration, or both (a) and (b). In some embodiments, the helical rotation is at least 360 degrees of rotation, in some embodiments, the helical rotation is at least 540 degrees of rotation, and in some embodiments, the helical rotation is at least 720 degrees of rotation. Various embodiments in which the elongate members 304 or portions thereof arranged with contours that follow each other may provide spatially efficient arrangements.

Further describing spatially efficient arrangements, in some embodiments, at least the second particular portions 309c of a first set (e.g., first set 309c-1a) of the plurality of elongate members 304 are arranged front surface 318a-toward-back surface 318b in a stacked arrangement (e.g., a helical stacked arrangement such as that shown in Figured 3G and 3H) at least when the structure 308 is in an unexpanded or a delivery configuration. For example, in each of FIGS. 3G and 3H, the first set 309c-1 of the second particular portions 309c of the first set 309c-1a of elongate members 304 are arranged front surface 318a-toward-back surface 318b in a first stacked arrangement at least when the structure 308 is in an unexpanded or a delivery configuration, according to some embodiments. Since, for example, in some embodiments, the second particular portions 309c maintain their helical configurations within shaft member 316 when the structure 308 moves from its delivery or unexpanded configuration to its deployed or expanded configuration, the first set 309c-1 of the second particular portions 309c of the first set 309c-1a of elongate members 304 are arranged front surface 318a-toward-back surface 318b in a second stacked arrangement at least when the structure 308 is in an expanded or a deployed configuration, according to some embodiments. In some embodiments, the first and second stacked arrangements in this regard are helical stacked arrangements.

The same just stated for the first set 309c-1 of the second particular portions 309c of the first set 309c-1a of elongate members 304 also applies to the second set 309c-2 of the second particular portions 309c of the second set 309c-2a of elongate members 304 in some embodiments. For example, in each of FIGS. 3G and 3H, the second set 309c-2 of the second particular portions 309c of the second set 309c-2a of elongate members 304 are arranged front surface 318a-toward-back surface 318b in a first stacked arrangement at least when the structure 308 is in an unexpanded or a delivery configuration, according to some embodiments. Since, for example, in some embodiments, the second particular portions 309c maintain their helical configurations within shaft member 316 when the structure 308 moves from its delivery or unexpanded configuration to its deployed or expanded configuration, the second set 309c-2 of the second particular portions 309c of the second set 309c-2a of elongate members 304 are arranged front surface 318a-toward-back surface 318b in a second stacked arrangement at least when the structure 308 is in an expanded or a deployed configuration, according to some embodiments. As mentioned above, in some embodiments, the first and second stacked arrangements in this regard are helical stacked arrangements. Also as mentioned above, each of the first set 309c-1a and the second set 309c-2a of elongate members 304 may include at least two or at least three elongate members 304 according to some embodiments.

In some embodiments, the first set 309c-1 of the second particular portions 309c of the first set 309c-1a of elongate members 304 are arranged front surface 318a-toward-back surface 318b in a first stacked arrangement at least (a) when the structure 308 is in an unexpanded or a delivery configuration, (b) when the structure 308 is in an expanded or deployed configuration, or both (a) and (b), according to some embodiments. In some embodiments, the second particular portions 309c of the second set 309c-2a of elongate members 304 are arranged front surface 318a-toward-back surface 318b in a second stacked arrangement at least (a) when the structure 308 is in an unexpanded or a delivery configuration, (b) when the structure 308 is in an expanded or deployed configuration, or both (a) and (b), according to some embodiments. In this regard, the first stacked arrangement may be axially or longitudinally (along the longitudinal axis of the shaft member 316) offset from the second stacked arrangement, as shown, for example in each of Figured 3G and 3H, with the axial or longitudinal offset of the first set 309c-1 of the second particular portions 309c with respect to the second set 309c-2 of the second particular portions 309c. As mentioned above, in some embodiments, the first and second stacked arrangements in this regard are helical stacked arrangements. Also as mentioned above, each of the first set 309c-1a and the second set 309c-2a of elongate members 304 may include at least two or at least three elongate members 304 according to some embodiments.

In some embodiments, e.g., as shown in FIGS. 3G and 3H, while each second particular portion 309c may itself form its own helical configuration, the first set 309c-1 of the second particular portions 309c of the first set 309c-1a of the elongate members 304 may form a first collective helical configuration, and the second set 309c-2 of the second particular portions 309c of the second set 309c-2a of the elongate members 304 may form a second collective helical configuration at least (a) when the structure 308 is in an unexpanded or delivery configuration, (b) when the structure 308 is in an expanded or deployed configuration, or both (a) and (b). In some embodiments, (i) the first collective helical configuration is a first collective helical configuration, e.g., forming a single collective helix, (ii) the second collective helical configuration is a second single collective helical configuration, e.g., forming a single collective helix, or both (i) and (ii). In this regard, the individual helical configurations of the respective individual second particular portions 309c may be combined (e.g., by nesting or contour following described above) to form one or more collective helical configurations. In some embodiments, the first collective helical configuration and the second collective helical configuration together form multiple collective (double in the case of FIGS. 3G and 3H) helical configurations similar to a multi-helix structure such as the double helix structure employed by DNA (Deoxyribonucleic acid). Another example of such a collective multiple helical configuration may be envisioned as including a form similar to a screw type mechanical device (e.g., a screw-type fastener or lead-screw) comprising a multi-start threaded form that includes more than one (commonly two to four) parallel, non-crossing helix according to some embodiments. These examples are non-limiting and the sets may be grouped to form other collective helical configurations. In some embodiments, each collective helical configuration is arranged such that the respective set of second particular portions 309c are combined in one or more arrangements that each have a helical arrangement or configuration. In some embodiments, each collective helical configuration is arranged such that a grouping of the respective set of second particular portions 309c in each of one or more arrangements has a helical configuration. Just as some embodiments have multiple helical configurations (e.g., FIGS. 3E, 3G, and 3H) as compared to embodiments that have a single helical configuration (e.g., FIG. 3D), some embodiments may have multiple twisted, non-helical configurations as compared to embodiments that have a single twisted, non-helical configuration (e.g., FIG. 3F).

According to some embodiments, such as those shown in FIGS. 3G and 3H, the second particular portions 309c in the first set 309c-1a of the elongate members 304 are axially or longitudinally offset (e.g., offset along a longitudinal axis of shaft member 316 or along an axis of a helix associated with the second particular portions 309c in either of the first set 309c-1a or the second set 309c-2a) from the second particular portions 309c in the second set 309c-2a of the elongate members 304 at least when the structure 308 (a) is in an unexpanded or delivery configuration, (b) is an expanded or deployed configuration, or both (a) and (b), according to some embodiments. In some embodiments, a helical configuration of the second particular portion 309c of a first elongate member 304 (e.g., a first elongate member 304-1a1 in the first set 309c-1a of the elongate members 304) is axially or longitudinally offset from a helical configuration of the second particular portion 309c of a second elongate member 304 (e.g., a second elongate member 304-2a2 in the second set 309c-2a of the elongate members 304) at least when the structure 308 (a) is in an unexpanded or delivery configuration, (b) is in an expanded or deployed configuration, or both (a) and (b). In some embodiments, a helically configured second particular portion 309c of a first elongate member 304 (e.g., a first elongate member 304-1a1 in the first set 309c-1a of the elongate members 304) is axially or longitudinally offset from a helically configured second particular portion 309c of a second elongate member 304 (e.g., a second elongate member 304-2a2 in the second set 309c-2a of the elongate members 304) at least when the structure 308 (a) is in an unexpanded or delivery configuration, (b) is in an expanded or deployed configuration, or both (a) and (b).

The use of offset (e.g., axial or longitudinal offset) helically configured second particular portions 309c or offset (e.g., axial offset) groups of helically configured second particular portions 309c (forming collective helical configurations) may be motivated for different reasons. For example, in some embodiments in which the second particular portions 309c are located within the elongated portion 316c of the shaft member 316, axial or longitudinal offset between various ones of the helical second particular portions 309c may be employed to produce an arrangement of reduced dimensions as compared to an arrangement in which the helical second particular portions 309c are all arranged in a single collective helix configuration. While a single collective helical configuration of second particular portions 309c is beneficial and provides improved bending characteristics according to some embodiments of the present invention, multiple collective helical configurations, such as the axially offset collective helical configurations shown in FIGS. 3G and 3H, may also provide additional benefits, such as space efficiency, according to some embodiments. Such an offset arrangement in turn may allow the use of shaft elongated portion 309c with smaller cross-sectional dimensions which may facilitate percutaneous or intravascular delivery thereof. Further, offset helical second particular portions 309c may also more evenly distribute internal stiffness of the shaft member 316 to thereby allow for more evenly distributed bending characteristics of the shaft member 316 and improve delivery performance of the shaft member 316 and positioning of the structure 308 within a bodily cavity. Further still, offset helical second particular portions 309c may also provide more evenly distributed bending characteristics to a greater (e.g., longer) portion of the shaft member 316.

According to some embodiments, such as those shown in FIGS. 3G and 3H, the second particular portions 309c each extend along a same rotational direction (e.g., a same clockwise direction or a same counterclockwise direction depending on viewing direction) when the structure 308 is at least in an unexpanded or delivery configuration, according to some embodiments. In this regard, in some embodiments, the second particular portions 309c of the first set 309c-1a of the elongate members 304 forming a first collective helical configuration extend along a same rotational direction (e.g., a same clockwise direction or a same counterclockwise direction) at least (a) when the structure 308 is in the unexpanded or delivery configuration, (b) when the structure 308 is in the expanded or deployed configuration, or both (a) and (b). Similarly, according to some embodiments, the second particular portions 309c of the second set 309c-2a of the elongate members 304 forming a second collective helical configuration extend along a same rotational direction (e.g., a same clockwise direction or a same counterclockwise direction) at least (a) when the structure 308 is in the unexpanded or delivery configuration, (b) when the structure 308 is in the expanded or deployed configuration, or both (a) and (b). In some embodiments, the second particular portions 309c of the first set 309c-1a of the elongate members 304 forming the first collective helical configuration and the second particular portions 309c of the second set 309c-2a of the elongate members 304 forming the second collective helical configuration extend along a same rotational direction (e.g., a same clockwise direction or a same counterclockwise direction) at least (a) when the structure 308 is in the unexpanded or delivery configuration, (b) when the structure 308 is in the expanded or deployed configuration, or both (a) and (b).

In some embodiments, the second particular portion 309c of a first elongate member 304 (e.g., the first elongate member 304-1a1 in the first set 309c-1a of the elongate members 304) extends along a same rotational direction as the second particular portion 309c of a second elongate member 304 (e.g., the second elongate member 304-2a2 in the second set 309c-2a of the elongate members 304) at least when the structure 308 is in an unexpanded or delivery configuration, the same rotational direction being a same clockwise direction or a same counterclockwise direction. In some embodiments, the second particular portion 309c of a first elongate member 304 extends along a different rotational direction than a rotational direction extended along by the second particular portion 309c of a second elongate member 304 at least when the structure 308 is in an unexpanded or delivery configuration.

Each of various ones of the second particular portions 309c includes a helical configuration that includes at least 360 degrees of rotation in some embodiments, at least 540 degrees of rotation in some embodiments, and at least 720 degrees of rotation in some embodiments. The amount of rotation of the helical configuration of a second particular portion 309c of various ones of the elongate members 304 may be motivated by different reasons. For example, in FIGS. 3G and 3H, each of the second particular portions 309c of the elongate members 304 in each of the first set and second sets 309c-1a, 309c-2a include a helical form that undergoes a particular amount of rotation over a particular length. The helical form imparts enhanced bending flexibility along the particular length of the second particular portion 309c. Therefore, according to some embodiments, the particular length of the second particular portion 309c may be varied based on the amount of rotation or the number of turns that the helical form undergoes. For example, in some embodiments, increased lengths of various ones of the second particular portions 309c having enhanced bending flexibility may be achieved at least in part by employing helical forms with greater amounts of rotation or greater numbers of turns. In some embodiments in which the second particular portions 309c are located within the elongated portion 316c of the shaft member 316, a desired length of enhanced flexibility in the shaft member 316 or an ability of the shaft member 316 to be bent with a particular bending radius may be achieved at least in part by employing various elongate members 304 whose second particular portions 309c have a helical configuration that includes a particular amount of rotation suitable to provide that particular capability.

In some embodiments, one or more control elements (e.g., 356) may be coupled to one or more of the elongate members 304 to control positioning or orientation of one or more of the elongate members 304. For example, a control element may be coupled to at least one elongate member 304 of the plurality of elongate members to at least in part control, for example, a positioning, tensioning or a configuration of at least the at least one elongate member 304 or at least one other elongate member 304. Previously cited U.S. Pat. No. 9,452,016, issued Sep. 27, 2016, includes disclosures regarding one or more control elements at least in part controlling, e.g., positioning, tensioning or a configuration of at least one elongate member, and U.S. Pat. No. 9,452,016, issued Sep. 27, 2016 is hereby incorporated herein by reference in its entirety.

According to some embodiments, such as those shown in FIGS. 3G and 3H, a control element 356 is coupled to each of at least a first particular set of the plurality of elongate members 304 to at least in part control a configuration of at least a second particular set of the plurality of elongate members 304. For example, in some embodiments, the control element 356 may be configured to transmit force provided by an actuator to facilitate, at least in part, a desired configuration in one or more of the elongate members 304. In some embodiments, the control element 356 may be configured to transmit force provided by an actuator to facilitate a movement of the structure 308 at least in part between an unexpanded or delivery configuration and an expanded or deployed configuration. Without limitation, control element 356 may include one or more control lines or cables, one or more control rods, one or more Bowden cables, or one or more other force transmission components. According to some embodiments, such as those shown in FIGS. 3G and 3H, the control element 356 includes a control line 356b located in a lumen of a control sleeve 356a. It is noted that control sleeve 356a is partially sectioned to show control line 356b. Control element 356 may be coupled to various ones of the elongate members 304 at various locations. For example, control element 356 may be coupled to the first particular portion 309a of each of at least some of the elongate members 304 according to some embodiments, although other coupling locations are possible in other embodiments.

According to some embodiments, such as the helical configurations shown in at least FIGS. 3D, 3E, 3G, and 3H, the plurality of elongate members 304 wrap around at least a portion of the control element 356 at least (a) when the structure 308 is in an unexpanded or delivery configuration, (b) when the structure 308 is in an expanded or deployed configuration, or both (a) and (b). In some embodiments, the second particular portions 309c of some or all of the plurality of elongate members 304 wrap around at least a portion of the control element 356 at least (a) when the structure 308 is in an unexpanded or delivery configuration, (b) when the structure 308 is in an expanded or deployed configuration, or both (a) and (b). In various embodiments, wrapping at least a portion of the control element 356 with various particular portions of various ones of the elongate members 304 may provide a spatially efficient arrangement since essentially unoccupied space provided by the wrapping particular portions of the various ones of the elongate members 304 may be effectively employed. According to some embodiments, such as those shown in FIGS. 3D, 3E, 3G, and 3H, the second particular portions 309c of the plurality of elongate members 304 wrap around the control element 356 along a same rotational direction at least (a) when the structure 308 is in an unexpanded or delivery configuration, (b) when the structure 308 is in an expanded or deployed configuration, or both (a) and (b). The same rotational direction may be a same clockwise direction or a same counterclockwise direction. In some embodiments, the second particular portions 309c of at least some of the plurality of elongate members 304 may wrap around the control element 356 along different or opposing rotational directions at least (a) when the structure 308 is in an unexpanded or delivery configuration, (b) when the structure 308 is in an expanded or deployed configuration, or both (a) and (b).

The characteristics of the helical stacking configurations of the second particular portions 309c discussed above with respect to double helical configuration of FIGS. 3G and 3H, including the collective stacking of multiple elongate members 304, the elongate member contour following, and elongate member nesting, etc., also apply to the double helical configuration of FIG. 3E, as well as a single helical configuration, such as that shown in FIG. 3D, and a twisted, non-helical configuration, such as that shown in FIG. 3F. For instance, in a case where the set of elongate members 304y includes multiple elongate members 304 and the set of elongate members 304z includes multiple elongate members 304, such multiple elongate members 304 may form a collective helical or a collective twisted, non-helical configuration, respectively, and one elongate member 304 may follow a contour of or be nested with another elongate member 304 in the respective set, in the manners discussed above with respect to the double helical configuration of FIGS. 3G and 3H. In this regard, in some implementations, at least some double helical configurations (e.g., FIGS. 3E, 3G, and 3H), may provide improved bending characteristics at potentially increased cost as compared to at least some single helical configurations (e.g., FIG. 3D), and, in some implementations, at least some single helical configurations may provide improved bending characteristics at potentially increased cost as compared to at least some twisted, non-helical configurations (e.g., FIG. 3F). However, all of these configurations (double helical, single helical, and twisted, non-helical) tend to provide improved bending characteristics as compared to non-twisted, non-helical configurations. Accordingly, depending on needs, double helical, single helical, or twisted, non-helical configurations may be suitable in different circumstances.

With regard to twisted, non-helical configurations, reference is made to various embodiments based at least on FIG. 3F. In some embodiments, the set 304y of at least some of the elongate members 304 may represent a plurality of elongate members 304 in a collective twisted, non-helical configuration or stack. In this regard, each elongate member 304 includes a second portion 309c, which is located within the elongated portion of the shaft member 316 as previously discussed. Further in this regard, each second portion 309c includes a twisted, non-helical configuration including at least 360 degrees of rotation in some embodiments, at least 540 degrees of rotation in some embodiments, and at least 720 degrees of rotation in some embodiments. Greater degrees of rotation may provide a longitudinally longer region of improved bendability characteristics.

Unlike helical configurations, the twisted, non-helical configuration of FIG. 3F intersects its axis of rotation. Accordingly, in some embodiments, each second portion 309c of each elongate member 304 in the set 304y of at least some of the elongate members 304 intersects an axis of rotation of its twisted, non-helical configuration.

As discussed above, in some embodiments, the second portions 309c of a set (e.g., 304y) of at least two elongate members 304 are arranged in a collective twisted, non-helical configuration (a) when the structure 308 is in the delivery configuration, (b) when the structure is in the deployed configuration, or both (a) and (b) since the configuration of the second portions 309c within the shaft member 316 may be maintained in both the delivery and deployed configurations of the structure 308. As shown in FIG. 3F, the second portions 309c of the set (e.g., 304y) of at least two elongate members 304 may extend along a same rotational direction in the collective twisted, non-helical configuration (a) when the structure 308 is in the delivery configuration, (b) when the structure is in the deployed configuration, or both (a) and (b), where the same rotational direction may be a same clockwise direction or a same counterclockwise direction. In some embodiments, the second portion 309c of each of at least a first elongate member 304 is nested with the second portion 309c of a second elongate member 304 (e.g., in the set 304y of elongate members 304) (a) when the structure is in the delivery configuration, (b) when the structure is in the deployed configuration, or both (a) and (b).

In some embodiments, for each particular elongate member 304, e.g., in the set 304y in FIG. 3F, the first portion 309a of the particular elongate member 304 and the second portion 309c of the particular elongate member 304 are provided by a plurality of portions of the particular elongate member arranged between a proximal portion (e.g., 307a or 307b) of the particular elongate member 304 and a distal end 305 of the particular elongate member 304, the plurality of portions of the particular elongate member 304 collectively providing a front surface 318a (one instance shown in FIG. 3F for a top-most elongate member) of the particular elongate member 304 and a back surface 318b (one instance shown in FIG. 3F for a bottom-most elongate member) of the particular elongate member 304 opposite across a thickness of the particular elongate member from the front surface 318a of the particular elongate member 304. At least a particular portion (e.g., first portion 309a in the non-twisted, non-helical stacked arrangement in, e.g., FIG. 3A or second portion 309c in the twisted, non-helical stack in FIG. 3F) of the front surface 318a of a first elongate member 304 may face at least a particular portion of the back surface 318b of a second elongate member 304 (e.g., an elongate member adjacent in the respective stack) when the structure 308 is in the delivery configuration. In some embodiments, at least the particular portion of the front surface 318a of the first elongate member 304 follows a contour of at least the particular portion of the back surface 318b of the second elongate member 304 at least when the structure 308 is in the delivery configuration. In some embodiments, at least the particular portion of the front surface 318a of the first elongate member 304 follows the contour of at least the particular portion of the back surface 318b of the second elongate member 304 throughout a rotation of the twisted, non-helical configuration of the second portion 309c of the second elongate member.

In some embodiments, at least the second portions 309c of a first set (e.g., 304y) of at least three of the elongate members 304 may be arranged front surface-toward-back surface in a first stacked arrangement when the structure 308 is in the delivery configuration, and at least the second portions 309c of the first set (e.g., 304y) of at least three elongate members 304 may be arranged front surface-toward-back surface in a second stacked arrangement when the structure is in the deployed configuration. For example, the second portions 309c in FIG. 3F may continue to be in a stacked arrangement when the structure 308 transitions from the delivery configuration to the deployed configuration, at least because the second portions 309c reside within the shaft member 316 and the transition of the structure 308 from the delivery configuration to the deployed configuration may leave the stacked arrangement of the second portions 309c relatively unaffected. In some embodiments, the first portions 309a of the first set (e.g., 304y) of at least three elongate members are arranged front surface-toward-back surface in a second stacked arrangement when the structure is in the delivery configuration (e.g., the first portions 309a in FIG. 3A are in a non-helical stacked arrangement that is substantially free from twisting when the structure is in the delivery configuration). In some embodiments, the first portion (e.g., 309a) of each elongate member 304 of a plurality of elongate members 304 is not arranged in a twisted, non-helical configuration including at least 360 degrees of rotation when the structure 308 is in the delivery configuration.

In this regard, in contrast to the helical stacking (e.g., FIGS. 3D, 3E, 3G, and 3H, according to some embodiments) or the twisted, non-helical stacking (e.g., FIG. 3F, according to some embodiments) of the second particular portions 309c, some embodiments provide a non-twisted, non-helical, such as a linear, stacked arrangement of the first particular portions 309a. (The term "non-twisted" in this context is intended to refer to such portions 309a being substantially free of twist.) With reference to the examples of FIGS. 3G and 3H for illustration, the first portions 309a of the first set 309c-1a of the elongate members 304 may be arranged front surface 318a-toward-back surface 318b in a stacked arrangement (e.g., a stacked arrangement of at least two elongate members 304 in some embodiments, or a stacked arrangement of at least three of the elongate members 304 in other embodiments) at least when the structure 308 is in an unexpanded or a delivery configuration (e.g., as shown in FIG. 3A or the right side of each of FIGS. 3G and 3H). In some embodiments, the first portions 309a of the second set 309c-2a of the elongate members 304 may be arranged front surface 318a-toward-back surface 318b in a stacked arrangement (e.g., a stacked arrangement of at least two elongate members 304 in some embodiments, or a stacked arrangement of at least three of the elongate members 304 in other embodiments) at least when the structure 308 is in an unexpanded or a delivery configuration (e.g., also as shown in FIG. 3A or the right side of each of FIGS. 3G and 3H). In some embodiments, both the first portions 309a of the first set 309c-1 and the second set 309c-2a of the elongate members 304 may be arranged front surface 318a-toward-back surface 318b in a combined stacked arrangement (e.g., as shown in the right side of each of FIGS. 3G and 3H). That is, while the second portions 309c of the elongate members 304 may be arranged in a set of one or more helical or twisted, non-helical stacked arrangements (e.g., one helical stacked arrangement in some embodiments of FIG. 3D, two helical stacked arrangements according to some embodiments of each of FIGS. 3E, 3G, and 3H, and one twisted, non-helical stacked arrangement in some embodiments of FIG. 3F, although other numbers of stacked arrangements may be provided), the first portions 309a may be arranged in a set that is made up of the same or fewer stacked arrangements than those comprised by the set of one or more helical stacked arrangements. For example, the second portions 309c in FIGS. 3E, 3G, and 3H may be arranged in two collective helical stacked arrangements, and the first portions 309a may be arranged in a single collective helical stacked arrangement (e.g., as shown on the right-side of FIGS. 3G and 3H. In some embodiments, a helical stacked arrangement or a twisted, non-helical stacked arrangement of the second particular portions 309c may be considered a first stacked arrangement, and the non-twisted, non-helical (e.g., linear) stacked arrangement of the first particular portions 309a may be considered a second stacked arrangement.

In some embodiments, at least some of the elongate members 304 providing first particular portions 309a in a stacked arrangement are the same as at least some of the elongate members 304 providing the second particular portions 309c in a stacked arrangement. In some embodiments, at least some of the elongate members 304 providing first particular portions 309a in a stacked arrangement are other than at least some of the elongate members providing the second particular portions 309c in a stacked arrangement. For example, as shown in FIGS. 3G and 3H, the at least some of the elongate members 304 (e.g., the elongate members 304 of the set 309c-2a) that provide at least some of the first particular portions 309a in a stacked arrangement are other than the elongate members that provide the second particular portions 309c in a stacked arrangement (e.g., the helical stacked arrangement provided the elongate members 304 of the set 309c-1a).

FIGS. 3G and 3H include a collar 316b1 at a transition region between the illustrated double helical configuration of the second portions 309c and the non-twisted, non-helical configuration of the first portions 309a (with the twisted portion 345 between the portions 309c and 309a). The same or a similar collar may be used for single helical configurations (e.g., FIG. 3D) or twisted, non-helical configurations (e.g., FIG. 3F) of the second portions 309c.

Figure 3I:
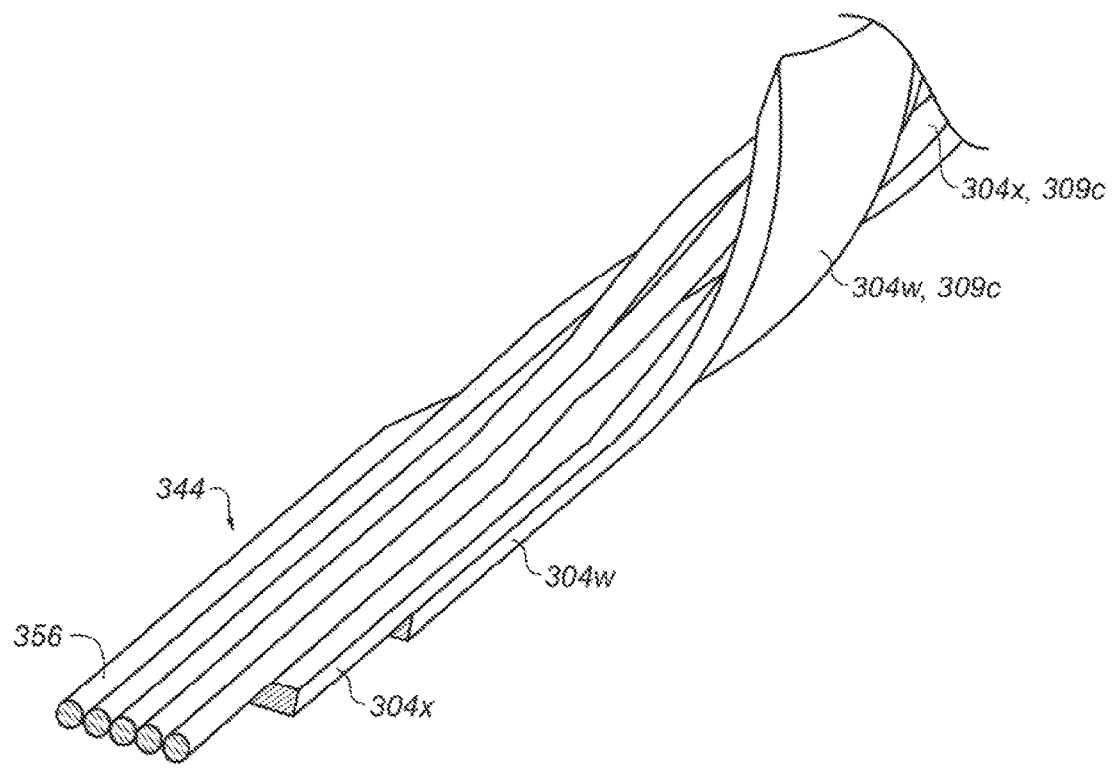
FIG. 3I illustrates, according to some embodiments, a transition between a rotationally offset double helical configuration and a non-twisted, non-helical configuration of elongate member portions of a medical device system, such as, but not limited to, a medical device system of FIG. 1, 2A, 2B, 3A, 3B, or 3C.
Figure 3J:
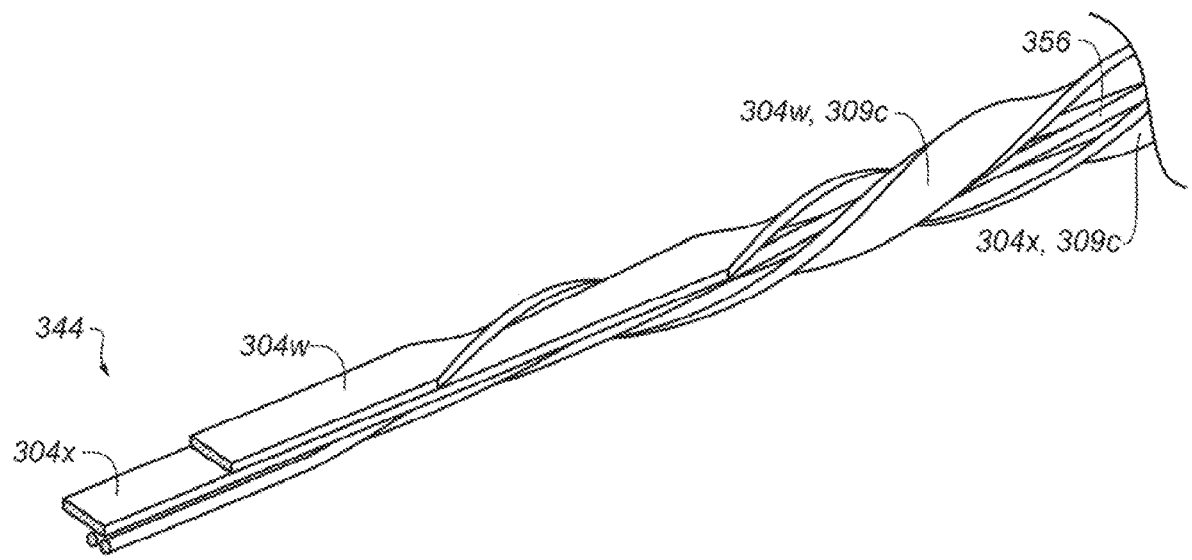
FIG. 3J illustrates, according to some embodiments, a transition between an axially offset double helical configuration and a non-twisted, non-helical configuration of elongate member portions of a medical device system, such as, but not limited to, a medical device system of FIG. 1, 2A, 2B, 3A, 3B, or 3C.

For further detail, FIGS. 3I and 3J illustrate examples of a transition region between double helical configurations of the second portions 309c and non-twisted, non-helical configurations of the first portions 309a, according to some embodiments. In particular, FIGS. 3I and 3J illustrate examples of a transition region between double helical configurations of the second portions 309c and an elongate member portion just proximally before twisted region 345 occurs, according to some embodiments. In this regard, FIG. 3I illustrates a transition from a rotationally offset double helical configuration to a non-twisted, non-helical configuration in a region 344 just proximally before twisted region 345, according to some embodiments. A rotationally offset double helical configuration is differentiated from the axially or longitudinally offset configurations illustrated in, e.g., FIGS. 3G and 3H. On the other hand, FIG. 3J illustrates a transition from an axially or longitudinally offset double helical configuration to a non-twisted, non-helical configuration in a region 344 just proximally before twisted region 345, according to some embodiments. In this regard, the axially or longitudinally offset double helical configuration illustrated in FIG. 3J corresponds to the axially or longitudinally offset double helical configuration illustrated in, e.g., FIGS. 3G and 3H. The non-twisted, non-helical region 344 just proximally before twisted region 345 illustrated in FIGS. 3G and 3H has been exaggerated to enhance the illustration of the unwinding of the respective double helical configurations.

FIGS. 3I and 3J remove the collar 316b1 and the shaft member 316 shown in at least FIGS. 3G and 3H for purposes of clarity. In addition, FIGS. 3I and 3J illustrate only a single elongate member 304w (of elongate members 304) for one helix and a single elongate member 304x (of elongate members 304) for the other helix of the respective double helical configuration for purposes of clarity. Other numbers of elongate members 304 may be provided according to various embodiments. Also, as with FIGS. 3D, 3E, and 3F, only a single control element 356 is called out, and different numbers of control elements 356 besides those illustrated may be provided according to various embodiments.

For additional detail regarding the winding of the axially offset double helical configuration (e.g., FIG. 3J) and the circumferentially offset double helical configuration (e.g., FIG. 3I), reference will now be made to FIGS. 3K and 3L.

Figure 3K:
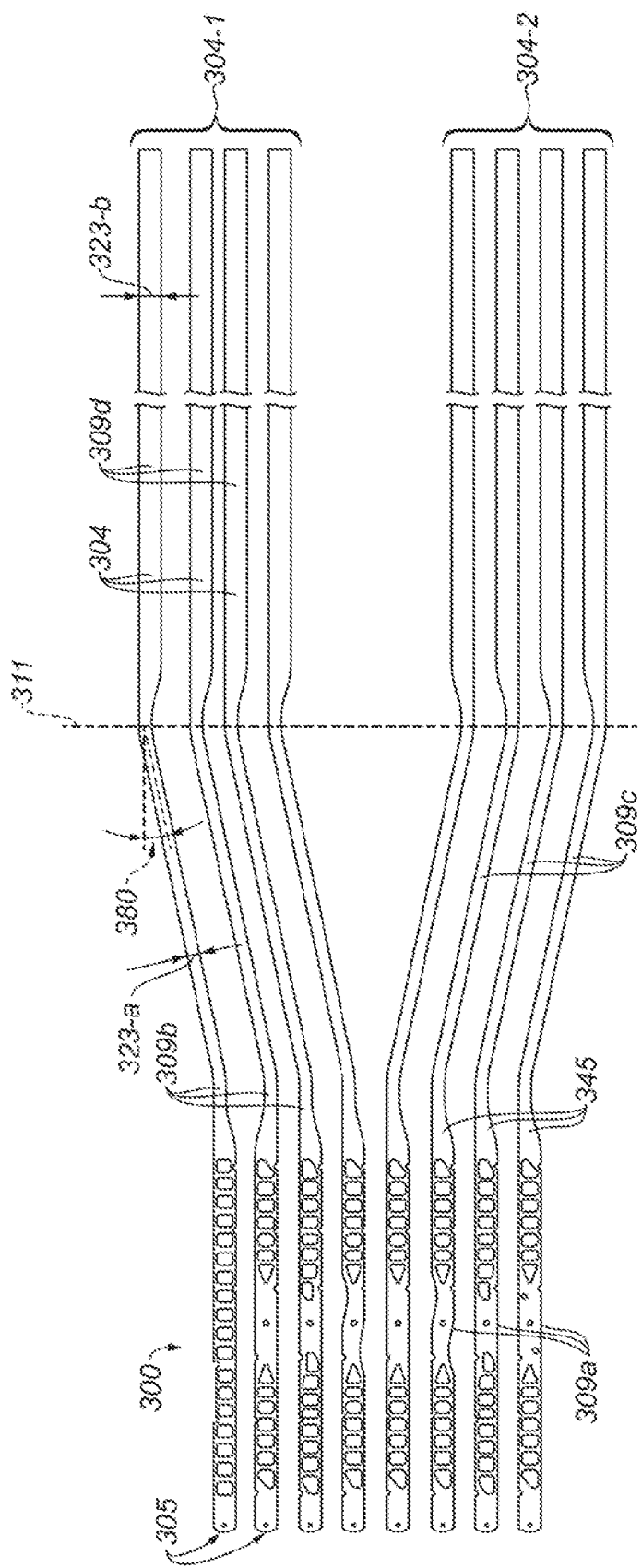
FIG. 3K is a representation of various elongate member portions in a flattened configuration absent a respective helical configuration, according to some embodiments, the respective helical configuration being a circumferentially or rotationally offset double helical configuration, according to some embodiments, such as, but not limited to, the circumferentially or rotationally offset double helical configuration of FIG. 3I.

FIG. 3K shows a plurality of elongate members 304 in a state prior to winding into a circumferentially or rotationally offset double helical configuration (e.g., FIG. 3I), according to some embodiments. Each of the elongate members 304 includes a distal end 305, a proximal end (e.g., 307) and a plurality of particular portions arranged between the distal end 305 and proximal end (e.g., 307). The plurality of particular portions include portions 309a, 309b, 309c, and 345 that are the same or similar to particular portions described earlier and having the same respective part (reference) number. For clarity, the elongate members 304 in FIG. 3K are shown in a "flattened" or an "undistorted" state, according to some embodiments. For example, particular portions 345 are shown in an untwisted state as opposed to the twisted state shown, e.g., in FIGS. 3A and 3B. By way of another example, particular portions 309c are shown without a helical configuration as opposed to the presence of a helical configuration in such portions 309c as described above. It is understood that various particular portions of elongate members 304 in FIG. 3K may, in some embodiments, include, for example, at a later time, or upon subsequent processing, various helical configurations. For example, in FIG. 3K, the various elongate members 304 are shown with a "flattened" or "planar" form that may exist, according to some embodiments, prior to subsequent processing or manipulation that imparts some distortions to the 'flattened or "planar" forms (e.g., distorted forms such as shown at least in FIGS. 3A and 3I).

According to some embodiments, the particular portion 309c of various ones of the elongate members 304 is arranged with a skewed orientation (e.g., a dog-legged) orientation with respect to another particular portion of the respective elongate member 304. The skewed or dog-legged configuration of particular portion 309c in the flattened or undistorted state shown, e.g., in FIG. 3K, may be motivated for different reasons. For example, when the particular portion 309c is subsequently manipulated to have a helical configuration (e.g., as shown in FIG. 3I), a change in angle at the beginning and end of the helical region may be required to transition into and out of (respectively) the helical shape to create a small form factor (e.g., a small overall shape capable of fitting within the confines of the elongated portion 316c of the shaft member 316). Without the change in angle provided by the skewed or dog-legged configuration of the particular portion 309c, particular portion 309c could bend out of plane when bent to comprise a helical configuration and thereby create a bulge that could provide a larger than desired shape or size. In FIG. 3K, the particular portions 309c of a first group 304-1 of the elongate members 304 are skewed with a first particular orientation (e.g., a positive skewed orientation), while the particular portions 309c of a second group 304-2 of the elongate members 304 are skewed with a second particular orientation (e.g., a negative skewed orientation) different than the first particular orientation according to some embodiments. In some embodiments, the change in orientation between the particular portions 309c in the first group 304-1 and the particular portions 309c in the second group 304-2 may be employed to cause, when the particular portions 309c are coiled into a helix, the start 311 of the helix of each particular portion 309c in the first group 304-1 to be rotationally positioned at a different location than the start 311 of the helix of each particular portion 309c in the second group 304-2. For example, in some embodiments, a viewing perspective along the axis of the formed helices would indicate that the start 311 of the helix of each particular portion 309c in the first group 304-1 would start, for example, at the 12 o'clock position while the start 311 of the helix of each particular portion 309c in the second group 304-2 would start at a rotationally offset position, for example, at the 6 o'clock position. According to some embodiments, such as those shown in FIG. 3I, employing different rotational starts as described above may be employed to achieve an axial offset between the helical portion 309c of elongate member 304w, for example, and the helical portion 309c of the second elongate member 304w, for example, to form a multi-helix structure (e.g., a multi-helix structure including a form similar to that of a double helix structure employed by DNA (Deoxyribonucleic acid)). It is noted that start 311 of each of the "flattened" particular portions 309c in FIG. 3K is depicted by a broken line positioned to represent that each of their respective helices start at the same substantially same axial position despite some of them starting at different rotational positions, according to some embodiments.

Figure 3L:
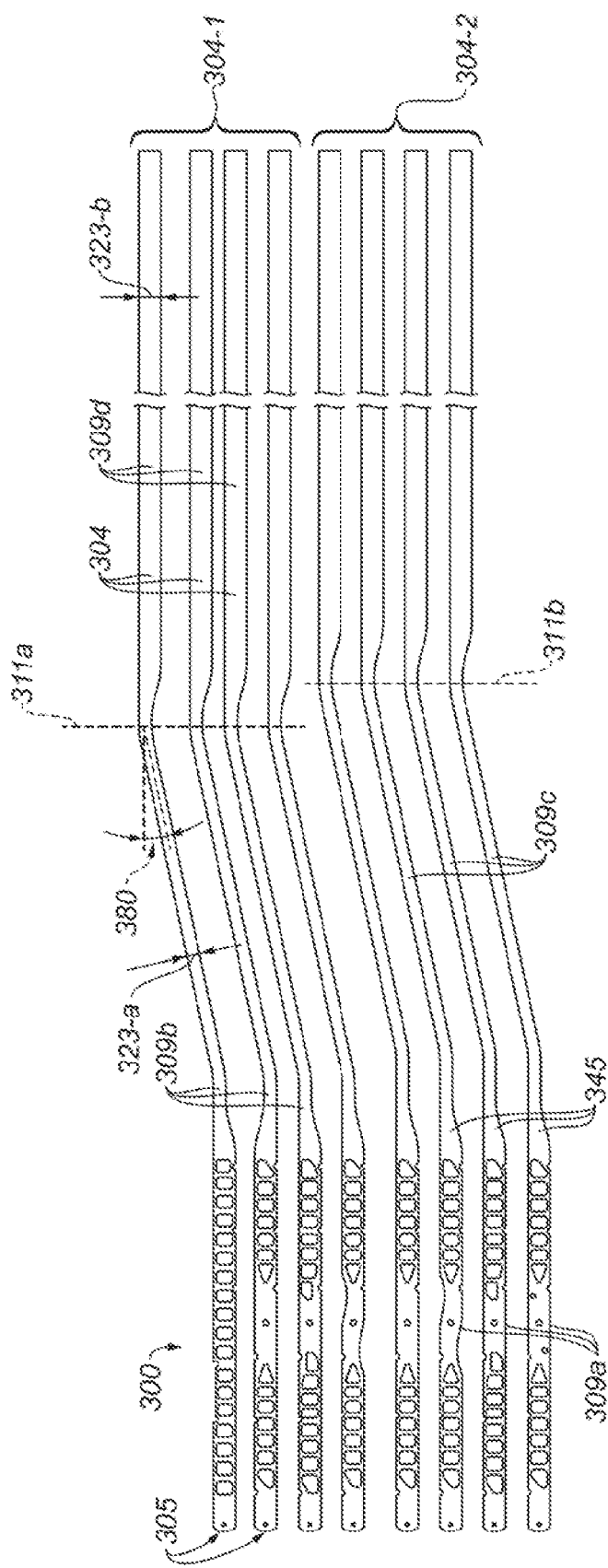
FIG. 3L is a representation of various elongate member portions in a flattened configuration absent a respective helical configuration, according to some embodiments, the respective helical configuration being a longitudinally or an axially offset double helical configuration, according to some embodiments, such as, but not limited to, the longitudinally or axially offset double helical configuration of FIG. 3J.

FIG. 3L shows a plurality of elongate members 304 in a state prior to winding into an axially or longitudinally offset double helical configuration (e.g., FIG. 3J), according to some embodiments. The plurality of elongate members 304 include similar features and are arranged in similar groupings to those shown in FIG. 3K, and the same or similar part numbers employed in FIG. 3K are employed in FIG. 3L for convenience of discussion. Accordingly, each of the elongate members 304 includes a distal end 305, a proximal end (e.g., 307) and a plurality of particular portions arranged between the distal end 305 and proximal end (e.g., 307). The plurality of particular portions include portions 309a, 309b, 309c, and 345 that that are the same or similar to particular portions described earlier and having the same respective part (reference) number. In a manner similar to, or the same as in, FIG. 3K, the elongate members 304 in FIG. 3L are shown in a "flattened" or an "undistorted" state, according to some embodiments. For example, particular portions 345 are shown in an untwisted state as opposed to a twisted state shown in FIG. 3A. By way of another example, particular portions 309c are shown without a helical configuration as opposed to the presence of a helical configuration as shown, for example, in FIGS. 3G, 3H, and 3J. It is understood, that various particular portions of elongate members 304 in FIG. 3L may, in some embodiments, include, for example, at a later time, or upon subsequent processing, various twisted or helical configurations. For example, in FIG. 3L, the various elongate members 304 are shown with a "flattened" or "planar" form that may exist, according to some embodiments, prior to subsequent processing or manipulation that imparts some distortions to the 'flattened' or "planar" forms (e.g., distorted forms such as shown at least in FIGS. 3A, 3G, 3H, and 3J).

According to some embodiments, the particular portion 309c of various ones of the elongate members 304 is arranged with a skewed orientation (e.g., a dog-legged) orientation with respect to other particular portion of the respective elongate member 304. The skewed or dog-legged configuration of particular portion 309c in the flattened or undistorted state shown, e.g., in FIG. 3L, may be motivated for different reasons including the reasons expressed above with respect to FIG. 3K. A comparison of the embodiments of FIGS. 3K and 3L indicates that unlike FIG. 3K in which the particular portions 309c of the first group 304-1 of the elongate members 304 are skewed with a first particular orientation that is different than the orientation of the particular portions 309c of the second group 304-2 of the elongate members 304, in FIG. 3L, both the particular portions 309c of the first group 304-1 of the elongate members 304 and the second group 304-2 of elongate members 304 are skewed with the same orientation (e.g., a positive orientation as discussed in above with respect to FIG. 3K). Additionally in FIG. 3L, an axial or longitudinal offset between particular portions 309c in the first group 304-1 and the particular portions 309c in the second group 304-2 may be employed according to some embodiments to cause, when the particular portions 309c are coiled into a helix, the start 311a of the helix of each particular portion 309c in the first group 304-1 to be axially or longitudinally positioned at a different location than the start 311b of the helix of each particular portion 309c in the second group 304-2.

In some embodiments, differences between the axial starts 311a, 311b of the particular portions 309c in the first group 304-1 and the particular portions 309c in the second group 304-2 may be employed to cause, when the particular portions 309c are coiled into a helix, the start of the helix of each particular portion 309c in the first group 304-1 to be axially or longitudinally positioned at a different location than the start of the helix of each particular portion 309c in the second group 304-2. According to some embodiments, such as those shown in FIGS. 3G, 3H, and 3J, employing different axial or longitudinal starts as described above may be employed to achieve an axial or longitudinal offset between the helical portions 309c in the first set 309c-1 and the helical portions 309c in the second set 309c-2, to form a multi-helix structure (e.g., a multi-helix structure including a form similar to that of a double helix structure employed by DNA (Deoxyribonucleic acid)). It is noted that start 311 of each of the "flattened" particular portions 309c in the second group 304-2 in FIG. 3L is depicted by a broken line positioned to represent that each of their respective helices start at different axial or longitudinal positions, according to some embodiments.

In some embodiments, for each elongate member 304 of at least some of the elongate members of the plurality of elongate members 304, a dimension or size of at least one of the particular portions of the elongate member 304 is different than a corresponding dimension or size of at least one other particular portion of the elongate member 304. For example, in FIGS. 3K and 3L, the width 323-a of the second particular portion 309c of at least one of the elongate members 304 is smaller than the corresponding width of another of the particular portions (for example, the width 323-b of particular portion 309d (e.g., proximal portion 307a or 307b) of the at least one of the elongate members 304). According to some embodiments, varying a size or dimension such as the width 323 among various particular portions of at least one of the elongate members 304 may be motivated by different reasons. For example, at least one elongate member 304 may employ a second particular portion 309c that has a reduced width as compared to the corresponding width of at least some of the other particular portions of the at least one elongate member 304 to allow the second particular portion 309c to more readily assume the helical configuration or to allow the second particular portion to assume a helical configuration of a desired reduced size or of particular size required by some particular spatial constraints (e.g., fitting within the confines of a lumen in shaft member 316). In some embodiments, both the second particular portions 309c and particular portions 309d are subject to the same spatial constraints (for example, both portions be required to extend through one or more lumens in shaft member 316). In various embodiments, the particular second portions 309c are helically configured to provide a particular benefit (e.g., enhanced flexibility of the shaft member 316) while the particular portions 309d are arranged in some other configuration which may not provide this particular benefit or may provide some other benefit. For example, the particular portions 309d may extend through a large or major portion of the shaft member 316 that does not require enhanced flexibility and thus these portions may be arranged in a non-helical configuration and may adopt larger widths. In some embodiments, for example, when at least the particular portions 309d are provided by flexible circuit structures or may extend sufficiently to provide a large or major portion of conductors 317, larger widths 323 for the portions 309d may be desired to provide additional space for electrical traces or conductors of larger width, the larger widths of the traces or conductors advantageously associated with reduced electrical resistance losses over large spans.

In this regard, with respect to FIGS. 3K and 3L, for each particular elongate member 304 of the plurality of elongate members 304: the second portion 309c of the particular elongate member 304 is between a proximal portion (e.g., 309d or 307a or 307b) of the particular elongate member 304 and the first portion e.g., 309a of the particular elongate member along a length of the particular elongate member 304, and the first portion 309a of the particular elongate member 304 is between the second portion 309c of the particular elongate member 304 and a distal end 305 of the particular elongate member 304 along the length of the particular elongate member 304, according to some embodiments. In some embodiments, a first width 323-a of the particular elongate member 304 in the second portion 309c is at least 10% less than a corresponding second width 323-b of the particular elongate member 304 in the proximal portion (e.g., 309d or 307a or 307b) of the particular elongate member 304. In some embodiments, the first width 323-a of the particular elongate member 304 in the second portion 309c is between 20% and 60%, inclusive, less than the corresponding second width 323-b of the particular elongate member 304 in the proximal portion of the particular elongate member 304. In some embodiments, the first width 323-a of each elongate member 304 is 3 mm and the second width 323-b of each elongate member 304 is 4.7 mm.

In some embodiments, wherein, for each particular elongate member 304 of the plurality of elongate members 304: the first portion 309a of the particular elongate member 304 and the second portion 309c of the particular elongate member 304 are provided by a plurality of portions of the particular elongate member 304 arranged between a proximal portion (e.g., 309d or 307a or 307b) of the particular elongate member 304 and a distal end 305 of the particular elongate member 304. The plurality of portions of the particular elongate member 304 may collectively provide a front surface 318a of the particular elongate member 304 and a back surface 318b of the particular elongate member 304 opposite across a thickness of the particular elongate member 304 from the front surface 318a of the particular elongate member 304, and the thickness of the particular elongate member 304 may be perpendicular to a longitudinal axis of the particular elongate member 304. In some embodiments, wherein, for each particular elongate member 304 of the plurality of elongate members 304: a first width 323-a of the particular elongate member 304 in the second portion 309c of the particular elongate member 304 is at least 10% less, or in some embodiments is between 20% and 60%, inclusive, less than a second width 323-b of the particular elongate member 304 in the proximal portion (e.g., 309d or 307a or 307b) of the particular elongate member 304, and each of the first width 323-a and the second width 323-b is perpendicular to the thickness and the longitudinal axis of the particular elongate member 304. In some embodiments, the first widths 323-a of the elongate members 304 are equal or within 5% of a same width. In some embodiments, for each particular elongate member of the plurality of elongate members: the proximal portion (e.g., 309d or 307a or 307b) of the particular elongate member 304 is adjacent the second portion 309c of the particular elongate member 304 along the longitudinal axis of the particular elongate member 304, and, in a state where the longitudinal axis of the particular elongate member 304 resides within a same plane (e.g., as shown in the flattened states of FIGS. 3K and 3L), the longitudinal axis of the particular elongate member 304 bends by a bending angle (one shown in each of FIGS. 3K and 3L with reference numeral 380 pointing to the angle between the two intersecting dotted lines) between the proximal portion (e.g., 309d or 307a or 307b) of the particular elongate member 304 and the second portion 309c of the particular elongate member 304. An absolute value of the bending angle is at least 5 degrees, in some embodiments, and between 10 and 20 degrees, inclusive, in some embodiments. In some embodiments, the bending angle for each elongate member 304 in a first subset (e.g., 304-2) of at least two elongate members 304 of the plurality of elongate members 304 is positive, and the bending angle for each elongate member 304 in a second subset (e.g., 304-1) of at least two elongate members 304 of the plurality of elongate members 304 is negative, the elongate members in the first subset other than the elongate members in the second subset.

While some of the embodiments disclosed above are described with examples of cardiac ablation, the same or similar embodiments may be used for ablating other bodily organs or any lumen or cavity into which the devices of the present invention may be introduced.

Subsets or combinations of various embodiments described above provide further embodiments.

These and other changes may be made to various embodiments in light of the above-detailed description. In general, in the following claims, the terms used should not be construed to limit the invention to the specific embodiments disclosed in the specification and the claims, but should be construed to include other electrode-based device systems including all medical treatment device systems and all medical diagnostic device systems in accordance with the claims. Further, it should be noted that, although several of the above-discussed embodiments are described within the context of an intra-cardiac medical device system, other embodiments apply to other medical and non-medical device systems. Accordingly, the invention is not limited by this disclosure, but instead its scope is to be determined entirely by the claims.

What is claimed is:

1. A medical device system comprising:
a plurality of transducer sets, each transducer set comprising one or more transducers positionable in a bodily cavity;
a plurality of elongate members, at least parts of the elongate members collectively forming a structure on which the plurality of transducer sets are located, each elongate member comprising at least a particular portion on which no transducer selectively operable to transmit energy is located; and
a shaft member physically coupled to the plurality of elongate members, a location at which the shaft member is physically coupled to each elongate member of the plurality of elongate members is fixed with respect to a shaft distal end of the shaft member, the shaft member configured to percutaneously deliver the structure to the bodily cavity at least in response to translation of at least part of the shaft member, and the shaft member comprising a shaft proximal end, the shaft distal end, and an elongated portion extending between the shaft proximal end and the shaft distal end,
wherein the structure is selectively moveable between:
a delivery configuration in which the structure is sized to be percutaneously deliverable to the bodily cavity, each of the plurality of elongate members comprising a helical configuration of the particular portion, the helical configuration including at least 360 degrees of rotation when the structure is in the delivery configuration, and
a deployed configuration in which the structure is sized too large to be percutaneously deliverable to the bodily cavity,
wherein, for each particular elongate member of the plurality of elongate members, the particular elongate member comprises a flexible circuit structure extending between a proximal portion of the particular elongate member and a distal end of the particular elongate member, the flexible circuit structure comprising the particular portion of the particular elongate member, and the flexible circuit structure comprising a conductive layer patterned on an electrically insulative layer, and
wherein the particular portion of each elongate member of the plurality of elongate members is located within the elongated portion of the shaft member.

2. The medical device system of claim 1, wherein each transducer set is located on at least one portion of a respective one of the plurality of elongate members other than the particular portion of the respective one of the plurality of elongate members.

3. The medical device system of claim 2, wherein each particular elongate member of the plurality of elongate members comprises a length between the proximal portion of the particular elongate member and the distal end of the particular elongate member, wherein the plurality of transducer sets are located on distal portions of the plurality of elongate members, the distal portions closer, along the lengths of the elongate members, to the distal ends of the elongate members than the particular portions of the plurality of elongate members when the structure is in the delivery configuration.

4. The medical device system of claim 2, wherein the at least one portions of the plurality of elongate members extend like lines of longitude about the structure when the structure is in the deployed configuration.

5. The medical device system of claim 2, wherein the at least one portion of each elongate member of the plurality of elongate members is not arranged in a helical configuration when the structure is in the delivery configuration.

6. The medical device system of claim 2, wherein the at least one portion of each elongate member of the plurality of elongate members is not arranged in a helical configuration when the structure is in the deployed configuration.

7. The medical device system of claim 1, wherein the particular portions of a set of at least two elongate members of the plurality of elongate members are arranged in a collective helical configuration when the structure is in the delivery configuration.

8. The medical device system of claim 7, wherein the particular portions of the set of at least two elongate members of the plurality of elongate members extend along a same rotational direction in the collective helical configuration when the structure is in the delivery configuration, the same rotational direction being a same clockwise direction or a same counterclockwise direction.

9. The medical device system of claim 1, wherein the particular portions of a set of at least two elongate members of the plurality of elongate members are arranged in a collective helical configuration when the structure is in the deployed configuration.

10. The medical device system of claim 1, wherein the particular portions of the plurality of elongate members are arranged in a particular configuration that remains sufficiently small in size to be percutaneously deliverable to the bodily cavity when the structure is moved from the delivery configuration to the deployed configuration.

11. The medical device system of claim 1, wherein the at least 360 degrees of rotation is at least 540 degrees of rotation.

12. The medical device system of claim 1, wherein the at least 360 degrees of rotation is at least 720 degrees of rotation.

13. The medical device system of claim 1, comprising a control element coupled to at least one elongate member of the plurality of elongate members to at least in part control a configuration of at least the at least one elongate member, wherein the plurality of elongate members wrap around at least a portion of the control element at least when the structure is in the delivery configuration.

14. The medical device system of claim 1, comprising a control element coupled to at least one elongate member of the plurality of elongate members to at least in part control a configuration of at least the at least one elongate member, wherein the particular portions of the plurality of elongate members wrap around at least a portion of the control element at least when the structure is in the delivery configuration.

15. The medical device system of claim 14, wherein the particular portions of the plurality of elongate members wrap around at least the portion of the control element when the structure is in the deployed configuration.

16. The medical device system of claim 14, wherein the particular portions of the plurality of elongate members each wraps around the control element along a same rotational direction at least when the structure is in the delivery configuration, the same rotational direction being a same clockwise direction or a same counterclockwise direction.

17. The medical device system of claim 1, wherein a portion of a first elongate member of the plurality of elongate members is nested with a portion of a second elongate member of the plurality of elongate members at least when the structure is in the delivery configuration.

18. The medical device system of claim 1, wherein the particular portion of each of at least a first elongate member of the plurality of elongate members is nested with the particular portion of a second elongate member of the plurality of elongate members at least when the structure is in the delivery configuration.

19. The medical device system of claim 1,
wherein, for each particular elongate member of the plurality of elongate members, the particular portion of the particular elongate member and the part of the particular elongate member that forms a respective part of the structure are provided by a plurality of portions of the particular elongate member arranged between the proximal portion of the particular elongate member and the distal end of the particular elongate member, the plurality of portions of the particular elongate member collectively providing a front surface of the particular elongate member and a back surface of the particular elongate member opposite across a thickness of the particular elongate member from the front surface of the particular elongate member,
wherein at least a portion of the front surface of each particular elongate member of the plurality of elongate members faces outwardly from an interior of the structure when the structure is in the deployed configuration, and
wherein at least a contacting portion of the front surface of a first elongate member of the plurality of elongate members contacts at least a contacting portion of the back surface of a second elongate member of the plurality of elongate members when the structure is in the delivery configuration.

20. The medical device system of claim 19, wherein at least the contacting portion of the front surface of the first elongate member follows a contour of at least the contacting portion of the back surface of the second elongate member.

21. The medical device system of claim 20, wherein the contacting portion of the front surface of the first elongate member is provided by the particular portion of the first elongate member, and the contacting portion of the back surface of the second elongate member is provided by the particular portion of the second elongate member.

22. The medical device system of claim 21, wherein at least the contacting portion of the front surface of the first elongate member follows the contour of at least the contacting portion of the back surface of the second elongate member throughout the at least 360 degrees of rotation of the helical configuration of the particular portion of the second elongate member.

23. The medical device system of claim 1,
wherein, for each particular elongate member of the plurality of elongate members, the particular portion of the particular elongate member and the part of the particular elongate member that forms a respective part of the structure are provided by a plurality of portions of the particular elongate member arranged between the proximal portion of the particular elongate member and the distal end of the particular elongate member, the plurality of portions of the particular elongate member collectively providing a front surface of the particular elongate member and a back surface of the particular elongate member opposite across a thickness of the particular elongate member from the front surface of the particular elongate member,
wherein at least a portion of the front surface of each elongate member of the plurality of elongate members faces outwardly from an interior of the structure when the structure is in the deployed configuration, and
wherein at least the particular portions of a first set of at least three of the plurality of elongate members are arranged front surface-toward-back surface in a first stacked arrangement when the structure is in the delivery configuration.

24. The medical device system of claim 23, wherein at least the particular portions of the first set of at least three of the plurality of elongate members are arranged front surface-toward-back surface in a second stacked arrangement when the structure is in the deployed configuration.

25. The medical device system of claim 1, wherein the helical configuration of the particular portion of a first elongate member of the plurality of elongate members is axially offset from the helical configuration of the particular portion of at least a second elongate member of the plurality of elongate members when the structure is in the delivery configuration.

26. The medical device system of claim 25, wherein the particular portion of the first elongate member of the plurality of elongate members extends along a same rotational direction as the particular portion of the second elongate member of the plurality of elongate members when the structure is in the delivery configuration, the same rotational direction being a same clockwise direction or a same counterclockwise direction.

27. The medical device system of claim 1, wherein the plurality of transducer sets includes a plurality of electrodes.

28. The medical device system of claim 1, wherein each transducer of each transducer set of the plurality of transducer sets comprises a respective electrode.

29. The medical device system of claim 1, wherein, for each particular elongate member of the plurality of elongate members: the particular portion of the particular elongate member is between, along a length of the particular elongate member, (a) the proximal portion of the particular elongate member and (b) the part of the particular elongate member that forms a respective part of the structure, and the part of the particular elongate member is between the particular portion of the particular elongate member and the distal end of the particular elongate member along the length of the particular elongate member, the particular elongate member configured to be percutaneously advanced distal end of the particular elongate member ahead of at least the proximal portion of the particular elongate member when the structure is in the delivery configuration, and a first width of the particular elongate member in the particular portion at least 10% less than a corresponding second width of the particular elongate member in the proximal portion of the particular elongate member.

30. The medical device system of claim 1, wherein, for each particular elongate member of the plurality of elongate members: the particular portion of the particular elongate member is between, along a length of the particular elongate member, (a) the proximal portion of the particular elongate member and (b) the part of the particular elongate member that forms a respective part of the structure, and the part of the particular elongate member is between the particular portion of the particular elongate member and the distal end of the particular elongate member along the length of the particular elongate member, the particular elongate member configured to be percutaneously advanced distal end of the particular elongate member ahead of at least the proximal portion of the particular elongate member when the structure is in the delivery configuration, and a first width of the particular elongate member in the particular portion is between 20% and 60%, inclusive, less than a corresponding second width of the particular elongate member in the proximal portion of the particular elongate member.

31. The medical device system of claim 1, wherein, for each particular elongate member of the plurality of elongate members: the part of the particular elongate member, which forms a respective part of the structure, and the particular portion of the particular elongate member are provided by a plurality of portions of the particular elongate member arranged between the proximal portion of the particular elongate member and the distal end of the particular elongate member, the plurality of portions of the particular elongate member collectively providing a front surface of the particular elongate member and a back surface of the particular elongate member opposite across a thickness of the particular elongate member from the front surface of the particular elongate member, and the thickness of the particular elongate member perpendicular to a longitudinal axis of the particular elongate member.

32. The medical device system of claim 31, wherein, for each particular elongate member of the plurality of elongate members: a first width of the particular elongate member in the particular portion of the particular elongate member is at least 10% less than a second width of the particular elongate member in the proximal portion of the particular elongate member, and each of the first width and the second width is perpendicular to the thickness and the longitudinal axis of the particular elongate member.

33. The medical device system of claim 31, wherein, for each particular elongate member of the plurality of elongate members: a first width of the particular elongate member in the particular portion of the particular elongate member is between 20% and 60%, inclusive, less than a second width of the particular elongate member in the proximal portion of the particular elongate member, and each of the first width and the second width is perpendicular to the thickness and the longitudinal axis of the particular elongate member.

34. The medical device system of claim 33, wherein the first widths of the particular elongate members of the plurality of elongate members are equal or within 5% of a same width.

35. The medical device system of claim 31, wherein, for each particular elongate member of the plurality of elongate members: the proximal portion of the particular elongate member is adjacent the particular portion of the particular elongate member along the longitudinal axis of the particular elongate member, and, in a state where the longitudinal axis of the particular elongate member resides within a same plane, the longitudinal axis of the particular elongate member bends by a bending angle between the proximal portion of the particular elongate member and the particular portion of the particular elongate member, an absolute value of the bending angle being at least 5 degrees.

36. The medical device system of claim 31, wherein, for each particular elongate member of the plurality of elongate members: the proximal portion of the particular elongate member is adjacent the particular portion of the particular elongate member along the longitudinal axis of the particular elongate member, and, in a state where the longitudinal axis of the particular elongate member resides within a same plane, the longitudinal axis of the particular elongate member bends by a bending angle between the proximal portion of the particular elongate member and the particular portion of the particular elongate member, an absolute value of the bending angle being between 10 and 20 degrees, inclusive.

37. The medical device system of claim 36, wherein the bending angle for each elongate member in a first subset of at least two elongate members of the plurality of elongate members bends is positive, and wherein the bending angle for each elongate member in a second subset of at least two elongate members of the plurality of elongate members bends is negative, the elongate members in the first subset other than the elongate members in the second subset.

* * * * *